(12) United States Patent
Breslin et al.

(10) Patent No.: US 9,487,529 B2
(45) Date of Patent: Nov. 8, 2016

(54) MACROCYCLIC COMPOUNDS AS ALK, FAK AND JAK2 INHIBITORS

(71) Applicant: Cephalon, Inc., Frazer, PA (US)

(72) Inventors: Henry J. Breslin, Lansdale, PA (US); Bruce D. Dorsey, Ambler, PA (US); Gregory R. Ott, Media, PA (US)

(73) Assignee: Cephalon, Inc., Frazer, PA (US)

( * ) Notice: Subject to any disclaimer, the term of this patent is extended or adjusted under 35 U.S.C. 154(b) by 302 days.

(21) Appl. No.: 14/025,986

(22) Filed: Sep. 13, 2013

(65) Prior Publication Data

US 2014/0031351 A1 Jan. 30, 2014

Related U.S. Application Data

(63) Continuation of application No. PCT/US2012/028856, filed on Mar. 13, 2012.

(60) Provisional application No. 61/453,259, filed on Mar. 16, 2011.

(51) Int. Cl.
*C07D 487/08* (2006.01)
*C07D 487/18* (2006.01)

(52) U.S. Cl.
CPC ............ *C07D 487/08* (2013.01); *C07D 487/18* (2013.01)

(58) Field of Classification Search
CPC .......................... C07D 487/08; C07D 487/18
See application file for complete search history.

(56) References Cited

U.S. PATENT DOCUMENTS

2009/0286778 A1 11/2009 Combs et al.

OTHER PUBLICATIONS

Alexander, "Suppressors of Cytokine Signalling (SOCS) in the Immune System," *Nature Rev. Immunology* (2002), vol. 2, pp. 1-7.
Bagi et al., "Dual Focal Adhesion Kinase/Pyk2 Inhibitor Has Positive Effects on Bone Tumors," *Cancer* (2008), vol. 112, pp. 2313-2321.
Baker et al., "Hematopoietic cytokine receptor signaling," *Oncogene* (2007), vol. 26, pp. 6724-6737.
Berge et al., "Pharmaceutical Salts," *J. Pharm. Sci.* (1977), vol. 66, pp. 1-19.
Bromberg et al., "Stat3 as an Oncogene," *Cell* (1999), vol. 98, pp. 295-303.
Chatzizacharias et al., "Clinical significance of FAK expression in human neoplasia," *Histol. Histopathol.* (2008), vol. 23, pp. 629-650.
Chen et al., "Oncogenic mutations of ALK kinase in neuroblastoma," *Nature* (2008), vol. 455, pp. 971-975.
Chiarle et al., "The anaplastic lymphoma kinase in the pathogenesis of cancer," *Nat. Rev. Cancer* (2008), vol. 8, pp. 11-23.

Choi et al., "Identification of Novel Isoforms of the *EML4-ALK* Transforming Gene in Non-Small Cell Lung Cancer," *Cancer Res.* (2008), vol. 68, pp. 4971-4976.
Christensen et al., "Cytoreductive antitumor activity of PF-2341066, a novel inhibitor of anaplastic lymphoma kinase and c-Met, in experimental models of anaplastic large-cell lymphoma," *Mol. Cancer Ther.* (2007), vol. 6, pp. 3314-3322.
Dagvadorj et al., "Autocrine Prolactin Promotes Prostate Cancer Cell Growth via Janus Kinase-2-Signal Transducer and Activator of Transcritption-5a/b Signaling Pathway," *Endocinology* (2007), vol. 148, pp. 3089-3101.
Desai et al., "Clonal Evolution of Resistance to Imatinib in Patients with Metastatic Gastrointestinal Stromal Tumors," *Clin. Cancer Res.* (2007), vol. 13, pp. 5398-5405.
Ding et al., "Constitutively activated STAT3 promotes cell proliferation and survival in the activated B-cell subtype of diffuse large B-cell lymphomas," *Blood* (2008), vol. 111, pp. 1515-1523.
Engelman et al., "Mechanisms of Acquired Resistance to Epidermal Growth Factor Receptor Tyrosine Kinase Inhibitors in Non-Small Cell Lung Cancer," *Clin. Cancer Res.* (2008), vol. 14, pp. 2895-2899.
Engelman et al., "Acquired resistance to tyrosine kinase inhibitors during cancer therapy," *Curr. Opin. Genetics & Develop.* (2008), vol. 18, pp. 73-79.
Espinal, "What is the role of the insulin receptor tyrosine kinase?" *Trends Biochem. Sci.* (1988), vol. 13, pp. 367-368.
Ferrajoli et al., "The JAK-STAT Pathway: A Therapeutic Target in Hematological Malignancies," *Curr. Cancer Drug Targets* (2006), vol. 6, pp. 671-679.
Flex et al., "Somatically acquired *JAK1* mutations in adult acute lymphoblastic leukemia," *J. Exper. Med.* (2008), vol. 205, pp. 751-758.
Galkin et al., "Corrections," *Proc. Nat'l Acad. Sci. USA* (2007), vol. 104, pp. 2024-2025.
Gao et al., "Mutations in the EGFR kinase domain mediate STAT3 activation via IL-6 production in human lung adenocarcinomas," *J. Clin. Invest.* (2007), vol. 117, pp. 3846-3856.
George et al., "Activating mutations in ALK provide a therapeutic target in neuroblastoma," *Nature* (2008), vol. 455, pp. 975-978.
Halder et al., "Therapeutic Efficacy of a Novel Focal Adhesion Kinase Inhibito TAE226 in Ovarian Carcinoma," *Cancer Res.* (2007), vol. 67, pp. 10976-10983.

(Continued)

*Primary Examiner* — Samira Jean-Louis

(57) ABSTRACT

The present invention provides compounds of Formula I

Formula I

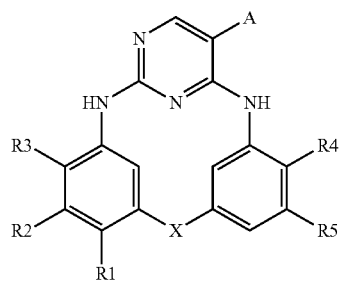

or a pharmaceutically acceptable salt forms thereof, wherein R1, R2, R3, R4, R5, A and X are as defined herein, methods of treatment and uses thereof.

22 Claims, No Drawings

(56) References Cited

OTHER PUBLICATIONS

Halder et al., "Focal Adhesion Kinase Targeting Using In Vivo Short Interfering RNA Delivery in Neutral Liposomes for Ovarian Carcinoma Therapy," *Clin. Cancer Res.* (2006), 12, pp. 4916-4924.
Han et al., "Role of Focal Adhesion Kinase in Human Cancer: A Potential Target for Drug Discovery," *Anti-Cancer Agents in Med. Chem.* (2007), vol. 7, pp. 681-684.
Hanahan et al., "The Hallmarks of Cancer," *Cell* (2000), vol. 100, pp. 57-70.
Hiroyuki, "Non-solid oncogenes in solid tumors: EML4-ALK fusion genes in lung cancer," *Cancer Sci.* (2008), vol. 99, pp. 2349-2355.
Hornakova et al., "Acute Lymphoblastic Leukemia-associated JAK1 Mutants Activate the Janus Kinase/STAT Pathway via Interleukin-9 Receptor α Homodimers," *J. Biological Chem.* (2009), vol. 284, pp. 6773-6781.
Iwahara et al., "Molecular characterization of ALK, a receptor tyrosine kinase expressed specifically in the nervous system," *Oncogene* (1997), vol. 14, pp. 439-449.
Iwamaru et al., "A novel inhibitor of the STAT3 pathway induces apoptosis in malignant glioma cells both in vitro and in vivo," *Oncogene* (2007), vol. 26, pp. 2435-2444.
Janoueix-Lerosey et al., "Somatic and germline activating mutations of the ALK kinase receptor in neuroblastoma," *Nature* (2008), vol. 455, pp. 967-970.
Knoops et al., "JAK kinases overexpression promotes in vitro cell transformation," *Oncogene* (2008), vol. 27, pp. 1511-1519.
Kohno et al., "CD151 Enhances Cell Motility and Metastasis of Cancer Cells in the Presence of Focal Adhesion Kinase," *Int. J. Cancer* (2002), vol. 97, pp. 336-343.
Koivunen et al., "EML4-ALK Fusion Gene and Efficacy of an ALK Kinase Inhibitor in Lung Cancer," *Clin. Cancer Res.* (2008), vol. 14, pp. 4275-4283.
Kornberg, "Focal Adhesion Kinase Expression in Oral Cancers," *Heck & Neck* (1998), vol. 20, pp. 634-639.
Kortylewski et al., "Inhibiting Stat3 signaling in the hematopoietic system elicits multicomponent antitumor immunity," *Nature Med.* (2005), vol. 11, pp. 1314-1321.
Li et al., "Activation of Signal Transducer and Activator of Transcription 5 in Human Prostate Cancer is Associated with High Histological Grade," *Cancer Res.* (2004), vol. 64, pp. 4774-4782.
Liu et al., "BCR-ABL mutants spread resistance to non-mutated cells through a paracrine mechanism," *Leukemia* (2008), vol. 22, pp. 791-799.
McLean et al., "The Role of Focal-Adhesion Kinase in Cancer—A New Therapeutic Opportunity," *Nat. Rev. Cancer* (2005), vol. 5, pp. 505-515.
McDermott et al., "Genomic Alterations of Anaplastic Lymphoma Kinase May Sensitive Tumors to Anaplastic Lymphoma Kinase Inhibitors," *Cancer Res.* (2008), vol. 68, pp. 3389-3395.
Melzner et al., "Biallelic mutation of SOCS-1 impairs JAK2 degradation and sustains phosphor-JAK2 action in the MedB-1 mediastinal lymphoma line," *Blood* (2005), vol. 105, pp. 2535-2542.
Mitra et al., "Focal Adhesion Kinase: in Command and Control of Cell Motility," *Nature Rev. Molecular Cell Biology* (2005), vol. 6, pp. 56-68.
Morris et al., "ALK, the chromosome 2 gene locus altered by the t(2;5) in non-Hodgkin's lymphoma, encodes a novel neural receptor tyrosine kinase that is highly related to leukocyte tyrosine kinase (LTK)," *Oncogene* (1997), vol. 14, pp. 2175-2188.
Morris et al., "Fusion of a Kinase Gene, ALK, to a Nucleolar Protein Gene, NPM, in Non-Hodgkin's Lymphoma," *Science* (1994), vol. 263, pp. 1281-1284.
Mosse et al., "Identification of ALK as a major familial neuroblastoma predisposition gene," *Nature* (2008), vol. 455, pp. 930-936.

Nefedova et al., "Targeting of JAK/STAT Pathway in Antigen Presenting Cells in Cancer," *Curr. Cancer Drug Targets* (2007), vol. 7, pp. 71-77.
Owens et al., "Overexpression of the Focal Adhesion Kinase (p125$^{FAK}$) in Invasive Human Tumors," *Cancer Res.* (1995), vol. 55, pp. 2752-2755.
Palmer et al., "Anaplastic lymphoma kinase: signaling in development and disease," *Biochem. J.* (2009), vol. 420, pp. 345-361.
Parsons et al., "Focal Adhesion Kinase: Targeting Adhesion Signaling Pathways for Therapeutic Intervention," *Clin. Cancer Res.* (2008), vol. 14, pp. 627-632.
Passoni et al., "Mutation-Independent Anaplastic Lymphoma Kinase Overexpression in Poor Prognosis Neuroblastoma Patients," *Cancer Res.* (2009), vol. 69, pp. 7338-7346.
Piva et al., "Ablation of oncogenic ALK is a viable therapeutic approach for anaplastic large-cell lymphomas," *Blood* (2006), vol. 107, pp. 689-697.
Pylayeva et al., "Ras- and PI3K-dependent breast tumorigenesis in mice and humans requires focal adhesion kinase signaling," *J. Clin. Invest.* (2009), vol. 119, pp. 252-266.
Rane et al., "JAKs, STATs and Src kinases in hematopoiesis," *Oncogene* (2002), vol. 21, pp. 3334-3358.
Rikova et al., "Global Survey of Phosphotyrosine Signaling Identifies Oncogenic Kinases in Lung Cancer," *Cell* (2007), vol. 131, pp. 1190-1203.
Roberts et al., "Antitumor Activity and Pharmacology of a Selective Focal Adhesion Kinase Inhibitor, PF-562,271," *Cancer Res.* (2008), vol. 68, pp. 1935-1944.
Saperstein et al., "Design of a Selective Insulin Receptor Tyrosine Kinase Inhibitor and Its Effect on Glucose Uptake and Metabolism in Intact Cells," *Biochemistry* (1989), vol. 28, pp. 5694-5701.
Scheeren et al., "IL-21 is expressed in Hodgkin lymphoma and activates STAT5: evidence that activated STAT5 is required for Hodgkin lymphomagenesis," *Blood* (2008), vol. 111, pp. 4706-4715.
Schindler et al., "JAK-STAT Signaling: From Interferons to Cytokines," *J. Biological Chem.* (2007), vol. 282, pp. 20059-20063.
Schwock et al., "Targeting focal adhesion kinase signaling in tumor growth and metastasis," *Expert Opin. Ther. Targets.* (2010), vol. 14, pp. 77-94.
Shah et al., "Mechanisms of resistance to STI571 in Philadelphia chromosome-associated leukemias," *Oncogene* (2003), vol. 22, pp. 7389-7395.
Shiota et al., "Hyperphosphorylation of a novel 80 kDa protein-tyrosine kinase similar to Ltk in a human Ki-1 lymphoma cell line, AMS3," *Oncogene* (1994), vol. 9, pp. 1567-1574.
Shuai et al., "Regulation of JAK-STAT Signalling in the Immune System," *Nature* (2003), vol. 3, pp. 900-911.
Soda et al., "Identification of the transforming EML4-ALK fusion gene in non-small-cell lung cancer," *Nature* (2007), vol. 448, pp. 561-566.
Soda et al., "A mouse model for EML4-ALK-positive lung cancer," *PNAS* (2008), vol. 105, pp. 19893-19897.
Takeuchi et al., "KIF5B-ALK, a Novel Fusion Oncokinase Identified by an Immunohistochemistry-based Diagnostic System for ALK-positive Lung Cancer," *Clin. Cancer Res.* (2009), vol. 15, pp. 3143-3149.
Tremblay et al., "Focal Adhesion Kinase (pp125$^{FAK}$) Expression, Activation and Association with Paxillin and p50$^{CSK}$ in Human Metastatic Prostate Carcinoma," *Int. J. Cancer* (1996), vol. 68, pp. 164-171.
Van Nimwegen, "Requirement for Focal Adhesion Kinase in the Early Phase of Mammary Adenocarcinoma Lung Metastasis Formation," *Cancer Res.* (2005), vol. 65, pp. 4698-4706.
Webb et al., "Anaplastic lymphoma kinase: role in cancer pathogenesis and small-molecule inhibitor development for therapy," *Expert Rev. Anticancer Ther.* (2009), vol. 9, pp. 331-356.
Weber et al., "SOCS-3 is frequently methylated in head an neck squamous cell carcinoma and its precursor lesions and causes growth inhibition," *Oncogene* (2005), vol. 24, pp. 6699-6708.

(56) References Cited

OTHER PUBLICATIONS

Weniger et al., "Mutations of the tumor suppressor gene *SOCS-1* in classical Hodgkin lymphoma are frequent and associated with nuclear phosphor-STAT5 accumulation," *Oncogene* (2006), vol. 25, pp. 2679-2684.

Yoshikawa et al., "SOCS-1, a negative regulator of the JAK/STAT pathway, is silenced by methylation in human hepatocellular carcinoma and shows growth-suppression activity," *Nature Genetics* (2001), vol. 28, pp. 29-35.

Yu et al., "The STATS of Cancer—New Molecular Targets Come of Age," *Nature Rev. Cancer* (2004), vol. 4, pp. 97-105.

Zhao et al., "Signal transduction by focal adhesion kinase in cancer," *Cancer Metastatasis Rev.* (2009), vol. 28, pp. 35-49.

MACROCYCLIC COMPOUNDS AS ALK, FAK AND JAK2 INHIBITORS

CROSS REFERENCE TO RELATED APPLICATIONS

This application is a continuation application of International Application No. PCT/US2012/028856, filed Mar. 13, 2012, which claims priority to U.S. Provisional Application Ser. No. 61/453,259, filed Mar. 16, 2011. The disclosures of the aforementioned applications are incorporated herein by reference in their entireties for all purposes.

BACKGROUND OF THE INVENTION

Anaplastic lymphoma kinase (ALK) is an orphan receptor tyrosine kinase (RTK) originally identified as part of the nucleophosmin (NPM)-ALK fusion gene in anaplastic large cell lymphoma (ALCL) with a t(2;5) chromosomal translocation (Morris, S. W. et al., Science, 1994, 263, 1281-1284; Shiota, M. et al., Oncogene, 1994, 9, 1567-1574). ALK expression is mainly restricted to the central and peripheral nervous systems, implicating a potential role in the physiological development and function of the nervous system (Iwahara, T. et al., Oncogene, 1997, 14, 439-449; Morris, S. W., et al., Oncogene, 1997, 14, 2175-2188). ALK knockout mice possess a full life span and have no overt abnormalities (Webb, T. R. et al., Expert Rev. Anti-cancer Ther., 2009, 9, 331-356), suggesting ALK inhibition could be well tolerated without severe adverse effects. While the physiological role of ALK receptor has not been well defined, involvement of ALK in the oncogenesis of various human cancers has been well documented and characterized. Besides NPM-ALK, various other ALK fusion genes were subsequently detected in ALCL, inflammatory myofibroblastic tumor (IMT), diffuse large B-cell lymphoma (DLBCL), systemic histiocytosis, and most notably, in non-small cell lung cancer (NSCLC), resulting in the generation of oncogenic ALK fusion proteins with constitutive phosphorylation/activation of ALK, which plays causative role in tumorgenesis by aberrant phosphorylation of intracellular downstream substrates (Webb, T. R. et al., Expert Rev. Anti-cancer Ther., 2009, 9, 331-356; Palmer, R. H. et al., Biochem. J., 2009, 420, 345-361; Chiarle, R. et al., Nature Rev. Cancer, 2008, 8, 11-23; Mano H., Cancer Sci., 2008, 99, 2349-2355). In NSCLC, at least seven isoforms of an oncogenic fusion gene comprised of portions of the echinoderm microtubule-associated protein-like 4 (EML4) gene and ALK gene were identified in about 3-15% patients examined (Soda, M. et al., Nature, 2007, 448, 561-566; Choi Y. L. et al., Cancer Res., 2008, 68, 4971-4976; Takeuchi, K. et al., Clin. Cancer Res., 2009, 15, 3143-3149). Experimental data indicate that inhibition of ALK could markedly impair the growth of ALK-positive lymphoma and lung cancer cells in vitro and in vivo, indicating that ALK-positive ALCL and NSCLC cells displayed "ALK oncogene addiction" (Piva, R. et al., Blood, 2006, 107, 689-697; Wan, W. et al., 2006; Galkin, A. V. et al., Proc. Natl. Acad. Sci. USA, 2007, 104, 270-275; Christensen, J. G. et al., Mol. Cancer. Ther., 2007, 6, 3389-3395; Soda, M. et al., Proc. Natl. Acad. Sci. USA, 2008, 105, 19893-19897; Koivunen, J. P. et al., Clin. Cancer Res., 2008, 14, 4275-4283). Recently, it has also been reported that germline mutations in ALK are the cause of most hereditary neuroblastoma cases, and ALK activation by mutation and/or gene amplification is functionally relevant in high-risk sporadic neuroblastoma (Mosse, Y. P. et al., Nature, 2008, 455, 930-936; Chen, Y. et al., Nature, 2008, 455, 971-974; George, R. E. et al., Nature, 2008, 455, 975-978; Janoueix-Lerosey, I. et al., Nature, 2008, 455, 967-970; McDermott, U. et al., Cancer Res., 2008, 68, 3389-3395; Passoni, L. et al., Cancer Res., 2009, 69, 7338-7346). Attenuation and inhibition of ALK activating mutants or wild type (WT) receptor resulted in profound growth inhibition in human neuroblastoma cell lines (Mosse, Y. P. et al., Nature, 2008, 455, 930-936; Chen, Y. et al., Nature, 2008, 455, 971-974; George, R. E. et al., Nature, 2008, 455, 975-978; Janoueix-Lerosey, I. et al., Nature, 2008, 455, 967-970; McDermott, U. et al., Cancer Res., 2008, 68, 3389-3395; Passoni, L. et al., Cancer Res., 2009, 69, 7338-7346), indicating that the ALK receptor, either the activating mutants or overexpressed WT form, is a critical player in neuroblastoma development. Altogether, these findings indicate that ALK is a major therapeutic target for human cancers and inhibition of ALK with a small molecule ALK inhibitor would offer a potentially more effective and less toxic therapy for patients with ALK-positive tumors than conventional chemotherapy.

ALK belongs to the insulin receptor (IR) RTK superfamily, which includes insulin-like growth factor-1 receptor (IGF-1R), insulin related receptor (IRR) and leukocyte tyrosine kinase (LTK) (Iwahara, T. et al., Oncogene, 1997, 14, 439-449; Morris, S W. et al., Oncogene, 1997, 14, 2175-2188). Of these IR family members, inhibition of IR itself poses a potential liability due to its involvement in glucose uptake and metabolism (Espinal, Trends Biochem Sci, 1988, 13, 367-368; Saperstein, R. et al., Biochemistry, 1989, 28, 5694-5701). Development of ALK inhibitors with selectivity over IR is, therefore, desirable.

Focal adhesion kinase (FAK) is an evolutionarily conserved non-receptor tyrosine kinase localized at focal adhesions, sites of cellular contact with the extracellular matrix that functions as a critical transducer of signaling from integrin receptors and multiple receptor tyrosine kinases (Parsons, J. T. et al., Clin. Cancer Res., 2008, 14, 627-632; Han, E. K. and McGonigal, T., Anticancer Agents Med. Chem. 2007, 7: 681-684; Schwock, J. et al., Expert Opin. Ther. Targets, 2010, 14, 77-94). The integrin-activated FAK forms a binary complex with Src which can phosphorylate other substrates and trigger multiple signaling pathways. Given the central role of FAK in mediating signal transduction with multiple SH2- and SH3-domain effector proteins (Mitra, S. K. et al., Mol. Cell Biol., 2005, 6, 56-68), activated FAK plays a central role in mediating cell adhesion, migration, morphogenesis, proliferation and survival in normal and malignant cells (Mitra, S. K. et al., Mol. Cell Biol., 2005, 6, 56-68; McClean, G. W. et al., Nature Rev. Cancer, 2005, 5, 505-515; Han, E. K. and McGonigal, T., Anticancer Agents Med. Chem. 2007, 7: 681-684; Chatzizacharias, N. A. et al., Histol. Histopathol., 2008, 23, 629-650). Compared to normal quiescent cells, FAK over-expression and activation is a hallmark of multiple solid tumors, particularly those with a propensity for bone metastasis, specifically breast cancer, ovarian cancer, NSCLC, prostate cancer, and head/neck squamous cell carcinoma (HNSCC) (Zhao, J. and Guan J. L., Cancer Metastasis Rev., 2009, 28, 35-49.; Schwock, J. et al., Expert Opin. Ther. Targets, 2010, 14, 77-94). Moreover, FAK over-expression and activation mediate anchorage-independent cell survival and are associated with an enhanced invasive and metastatic phenotype and tumor angiogenesis in these malignancies (Owens, L. V. et al., Cancer Res., 1995, 55, 2752-2755., Kornberg, I. J., et al., Head and Neck, 1998, 20: 634-639; McClean, G. W. et al., Nature Reviews Cancer, 2005, 5, 505-515; Han, E. K. and McGonigal, T. Anticancer Agents Med. Chem. 2007, 7: 681-684; Chatzizacharias, N. A. et al., Histol. Histopathol., 2008, 23, 629-650). Elevated FAK levels in tumors are often caused by amplification of the FAK gene locus i.e. in breast carcinomas, and the critical role of FAK in the metastatic progression of breast cancer has been demonstrated pre-clinically in conditional knock-out studies (van Nimwegen, M. J. et al., Cancer Res., 2005, 65, 4698-4706.; Pylayeva, Y. et al., J. Clin. Invest., 2009, 119, 252-266). FAK activation also protects tumor cells from chemotherapy-induced apoptosis, contributing further to tumor survival and resistance (Han, E. K. and McGonigal, T. Anticancer Agents Med. Chem. 2007, 7, 681-684; Halder, J. et al., Clin. Cancer Res., 2006, 12, 4916-4924). Multiple proof-of-concept studies conducted in various solid tumors using siRNA (Halder, J. et al., Clin. Cancer Res., 2006, 12, 4916-4924), dominant-negative FAK (Kohno, M. et al, Int. J. Cancer. 2002, 97, 336-343) and small molecule FAK inhibitors (Halder, J. et al., Cancer Res., 2007, 67, 10976-10983; Roberts, W. G. et al., Cancer Res., 2008, 68, 1935-1944.; Bagi, C. M. et al., Cancer, 2008, 112, 2313-2321) have provided pre-clinical support for the therapeutic utility of FAK inhibition as an anti-tumor/anti-angiogenic strategy, particularly for androgen-independent prostate cancers, breast cancers, and HNSCC.

The Janus kinase (JAK)/Signal transducers and activators of transcription (STAT) pathway is the major signaling cascade downstream from cytokine receptors and growth factor receptors including growth hormone, prolactin and leptin (Rane, S. G. et al., Oncogene 2002, 21, 3334-3358; Schindler, C. et al., J. Biol. Chem. 2007, 282, 20059-20066; Baker, S. J. et al., Oncogene, 2007, 15, 6724-6737). The signaling cascade consists of the family of non-receptor tyrosine kinases, JAK and transcription factors, STAT. Activated JAK phosphorylate and activate STAT, allowing formation of homo- and heterodimers that translocate to the nucleus to regulate the transcription of STAT-dependent genes. In addition, STAT can be directly phosphorylated by non-receptor tyrosine kinases like Src or Abl. Under normal physiological conditions ligand-dependent activation of JAK/STAT signaling is transient and tightly regulated (Alexander, W. S., Nature Rev. Immunol., 2002, 2, 1-7; Shuai, K. et al., Nature Rev. Immunol., 2003, 3: 900-910). Constitutive activation of JAK and STAT was detected in a wide spectrum of human cancers, both solid and hematopoietic, and often correlated with a more malignant and metastatic phenotype and refractory tumors (Ferrajoli, A. et al., Curr. Cancer Drug Targets, 2006, 6, 671-9; Yu, H. et al., Nature Rev. Cancer, 2004, 4, 97-105). In most tumors JAK2/STAT activation was mediated by a constitutive expression of cytokines (IL-6, IL-4, GM-CSF) and/or by inactivation of endogenous repressors of the JAK/STAT pathway, including members of the suppressor of cytokine signaling (SOCS) family or phosphatase SHP-1 due to promoter methylation or specific deletions (Yoshikava, H. et al., Nature Genetics, 2001, 28, 29-35; Weber, A., at al., Oncogene, 2005, 24, 6699-708; Melzner, I., et al., Oncogene, 2005, 24, 6699-708; Weniger, M. et al., Oncogene, 2006, 25, 2679-84). In some tumors, activating mutations in JAK1 (Flex, E. et al., J. Exp. Med. 2008, 205, 751-758; Hornakova, T. et al., J. Biol. Chem. 2009, 384, 6773-6781), JAK2, JAK3 or JAK2 chimeric molecules were directly implicated in tumorigenesis. In addition, amplification of the JAK2 locus was found in 35% of Hodgkin lymphoma (HL) and 50% of primary mediastinal B-cell lymphoma (PMBL) cases (Melzner, I, et al., Blood, 2005, 105, 2535-2542). The ectopic expression of JAK1, JAK2 and JAK3, as well as STAT3 and STAT5 resulted in oncogenic transformation in recipient cells, demonstrating that the activated JAK2/STAT pathway was sufficient to mediate oncogenesis in various solid and hematological tumors (Bromberg, J. et al., Cell, 1999, 98, 295-303; Knoops, L. et al., Oncogene, 2008, 27, 1511-9; Scheeren, F. A. et al., Blood. 2008, 111, 4706-4715). In multiple studies, inhibition of JAK2/STAT signaling in various tumor cells, including prostate, breast, colon and lung carcinomas, gliomas as well as leukemias and lymphomas resulted in inhibition of growth, induction of apoptosis and suppression of tumor growth in vivo (Yu, H. et al., Nature Rev. Cancer, 2004, 4, 97-105; Li, H. et al., Cancer Res. 2004, 64, 4774-4782; Iwamaru, A. et al., Oncogene, 2007, 26, 2435-2444; Gao, S., et al., J. Clin. Invest., 2007, 117, 3846-3856; Ding, B. et al., Blood, 2008, 111, 1515-1523,). Pre-clinical studies have demonstrated that constitutively activated JAK2/STAT signaling in tumor cells not only promoted uncontrolled cell proliferation and anti-apoptotic signaling, but also mediated tumor immune evasion and angiogenesis (Kortylewski, R., et al., Nat. Med., 2005, 11, 1314-21; Nefedova, Y. et al., Curr. Cancer Drug Targets, 2007, 7, 71-77). Therefore, inhibitors of JAK/STAT signaling would potentially suppress multiple mechanisms underlying tumor formation and progression.

Human cancers are notoriously heterogeneous, even in those well established "oncogene addicted" tumors, since some cancer cells likely contain additional oncogenic event(s) or redundant active signaling pathways which may render the cancer cells less dependent on the primary oncogene for growth and survival (Hanahan, D. and Weinberg, R. A., Cell, 2000, 100, 57-70). Concomitant inhibition of the secondary oncogenic event(s) in those cancer cells would likely lead to increase the efficacy of treatment with a kinase inhibitor, either by combination therapy or developing a small molecule inhibitor against both the primary and secondary targets. For example, FAK was found to be hyperphosphorylated and activated in a majority of human NSCLC cell lines and contributed to promote cancer cell invasion and metastasis (Rikova, K., Cell, 2007, 131, 1190-1203). An ALK inhibitor with concomitant FAK activity may provide additive or synergistic anti-tumor activity against ALK-positive NSCLC, and potentially additional solid and hematological tumors containing functional ALK and FAK. Similarly, JAK2/STAT5 mediated signaling pathway plays an important role in androgen-independent prostate tumorigenesis (Li, H., et al. Cancer Res., 2004, 64, 4774-4782; Dagvadorj, A., et al., Endocrinology, 2007, 148, 3089-3101) and FAK activity was found to be critical for maintaining the invasive and metastatic phenotype of androgen-independent prostate cancer (Owen, L. V. et al, Cancer Res., 1995, 55, 2752-2755; Tremblay, L., et al., Int. J. Cancer, 1996, 68, 164-171). Therefore, there is a compelling rationale for the utility of a dual JAK2/FAK inhibitor to treat this type of cancer.

On the other hand, although kinase inhibitors have been extremely effective in specific patient populations with tumors containing mutated, oncogenic forms of protein tyrosine kinases (PTK), clinical studies thus far have shown that some patients eventually develop resistance to these drugs, either due to the selection of cancer cells with mutations in the targeted PTK or the induction of compensatory oncogenic signaling pathways (Shah, N. P. and Sawyers, C. L., Oncogene, 2003, 22, 7389-7395; Engelman, J. A. and Settleman, J., Curr. Opin. Genet. Develop., 2008, 18, 1-7; Liu, J. et al., Leukemia, 2008, 22, 791-799; Desai, J. et al., Clin. Cancer Res., 2007, 13, 5398-5405; Engelman, J. A. and Janne, P. A., Clin. Cancer Res., 2008, 14, 2895-2899). In that regard, a kinase inhibitor simultaneously inhibiting two or more critical, non-redundant signaling pathways may prevent or decrease the incident of resistant tumors to develop.

A need exists for ALK, FAK and JAK2 inhibitors for use as pharmaceutical agents.

SUMMARY OF THE INVENTION

The present invention provides a compound of Formula I

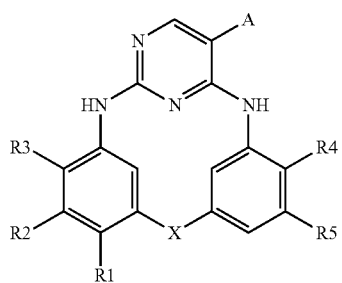

Formula I or a pharmaceutically acceptable salt form thereof, wherein A, R1, R2, R3, R4, R5 and X are as defined herein.

The compound of Formula I has ALK, FAK and/or JAK2 inhibitory activity, and may be used to treat ALK-, FAK or JAK2-mediated disorders or conditions.

The present invention further provides a pharmaceutical composition comprising at least one compound of the present invention together with at least one pharmaceutically acceptable carrier, diluent, or excipient therefor.

In another aspect, the present invention provides a method of treating a subject suffering from an ALK-, FAK or JAK2-mediated disorder or condition comprising: administering to the subject the pharmaceutical composition of the present invention.

The present invention further provides a method of treating a proliferative disorder in a subject, comprising administering to the subject a therapeutically effective amount of a compound of the present invention.

DETAILED DESCRIPTION OF THE INVENTION

I. Definitions

As used herein, the following terms have the meanings ascribed to them unless specified otherwise.

"Alkylamino" or an "alkylamino group" refers to an —NH-alkyl group.

"Alkoxy" or "alkoxy group" refers to an —O-alkyl group.

"Alkyl" or "alkyl group" refers to a branched or unbranched saturated hydrocarbon chain. Examples include, but are not limited to, methyl, ethyl, n-propyl, n-butyl, n-pentyl, n-hexyl, n-heptyl, n-octyl, n-nonyl, n-decyl, isopropyl, tert-butyl, isobutyl, etc. Alkyl groups typically contain 1-10 carbon atoms, such as 1-6 carbon atoms.

The term "$C_{x-y}$" indicates the number of carbon atoms in a group. For example, a "$C_{1-6}$-alkyl" is an alkyl group having from one (1) to six (6) carbon atoms.

The term "cyano" refers to a CN group.

"Carbocyclyl" or "carbocyclyl group" refers to a non-aromatic carbocyclic ring system, which may be saturated or unsaturated, substituted or unsubstituted, and may be monocyclic, bicyclic, or tricyclic, and may be bridged, spiro, and/or fused. Examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane. Preferably, the cycloalkyl group contains from 3 to 10 ring atoms. More preferably, the cycloalkyl group contains from 3 to 7 ring atoms, such as 3 ring atoms, 5 ring atoms, 6 ring atoms, or 7 ring atoms.

"Carbocyclyloxy" or a "carbocyclyloxy" group refers to a carbocyclyl-O— group.

"Aryl" or "aryl group" refers to phenyl and 7-15 membered monoradical bicyclic or tricyclic hydrocarbon ring systems, including bridged, spiro, and/or fused ring systems, in which at least one of the rings is aromatic. Aryl groups can be substituted or unsubstituted. Examples include, but are not limited to, phenyl, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Preferably, the aryl group contains 6 (i.e., phenyl) or 9 to 15 ring atoms. More preferably, the aryl group contains 6 (i.e., phenyl), 9 or 10 ring atoms.

"Heterocyclyl" or "heterocyclyl group" refers to 3-15 membered monocyclic, bicyclic, and tricyclic non-aromatic rings, which may be saturated or unsaturated, can be substituted or unsubstituted, may be bridged, spiro, and/or fused, and which contain, in addition to carbon atom(s), at least one heteroatom, such as nitrogen, oxygen or sulfur. Examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl, tetrahydropyranyl, piperidinyl, tetrahydrothienyl, homopiperidinyl, oxazolidinonyl, dihydropyrazolyl, dihydropyrrolyl, dihydropyrazinyl, dihydropyridinyl, dihydropyrimidinyl, dihydrofuryl, dihydropyranyl, quinuclidinyl, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane and 2,6-diaza-bicyclo[3.2.2]nonane. Preferably, the heterocyclyl group contains from 3 to 10 ring atoms. More preferably, the heterocycyl group contains from 3 to 7 ring atoms. More preferably, the heterocyclyl group contains from 5 to 7 ring atoms, such as 5 ring atoms, 6 ring atoms, or 7 ring atoms. Unless otherwise indicated, the foregoing heterocyclyl groups can be C-attached or N-attached where such is possible and results in the creation of a stable structure. For example, piperidinyl can be piperidin-1-yl (N-attached) or piperidin-4-yl (C-attached). A heterocyclyl group can also include ring systems substituted on ring carbons with one or more —OH functional groups (which may further tautomerize to give a ring C=O group) and/or substituted on a ring sulfur atom by one (1) or two (2) oxygen atoms to give S=O or $SO_2$ groups, respectively.

"Heteroaryl" or "heteroaryl group" refers to (a) 5 and 6 membered monocyclic aromatic rings, which contain, in addition to carbon atom(s), at least one heteroatom, such as nitrogen, oxygen or sulfur, and (b) 7-15 membered bicyclic and tricyclic rings, which contain, in addition to carbon atom(s), at least one heteroatom, such as nitrogen, oxygen or sulfur, and in which at least one of the rings is aromatic. Heteroaryl groups can be substituted or unsubstituted, and may be bridged, spiro, and/or fused. Examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0*2,7*]dodeca-2(7),3,5-trienyl, 12-oxa-10-aza-tricyclo[6.3.1.0*2,7*]dodeca-2(7),3,5-trienyl, 12-aza-tricyclo[7.2.1.0*2,7*]dodeca-2(7),3,5-trienyl, 10-aza-tricyclo[6.3.2.0*2,7*]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Preferably, the heteroaryl group contains 5, 6, or 8-15 ring atoms. More preferably, the heteroaryl group contains 5 to 10 ring atoms, such as 5, 6, 9, or 10 ring atoms. A heteroaryl group can also include ring systems substituted on ring carbons with one or more —OH or C=O functional groups and/or substituted on a ring sulfur atom by one (1) or two (2) oxygen atoms to give S=O or $SO_2$ groups, respectively.

"Hydroxyalkyl" or "hydroxyalky group" refers to an alkyl group containing an —OH group substituent.

"Dihydroxyalkyl" or "dihydroxyalkyl group" refers to an alkyl group containing two —OH group substituents.

"Alkoxyalkyl" or "alkoxyalkyl group" refers to an alkyl group containing an alkoxy group substituent.

"Aminocarbonylalkyl" or "aminocarbonylalkyl group" refers to an $H_2N$—C(O)-alkyl-group.

"N-alkylaminocarbonylalkyl" or "N-alkylaminocarbonylalkyl group" refers to an alkyl-NH—C(O)-alkyl-group.

"N,N-dialkylaminocarbonylalkyl" or "N,N-dialkylaminocarbonylalkyl group" refers to an (alkyl)(alkyl)N—C(O)-alkyl-group. In such a group the alkyl groups substituting the nitrogen may be the same or different.

"Alkylsulfonylalkyl" or "alkylsulfonylalkyl" group refers to an alkyl-$S(O)_2$-alkyl-group.

"Alkylsulfonyl" or "alkylsulfonyl" group refers to an alkyl-$S(O)_2$— group.

"Aminoalkylcarbonyl" or "aminoalkylcarbonyl group" refers to an $H_2N$-alkyl-C(O)— group.

"N-alkylaminoalkylcarbonyl" or "N-alkylaminoalkylcarbonyl group" refers to an alkyl-NH-alkyl-C(O)— group.

"N,N-dialkylaminoalkylcarbonyl" or "N,N-dialkylaminoalkylcarbonyl group" refers to an (alkyl)(alkyl)N-alkyl-C(O)— group. In such a group the alkyl groups substituting the nitrogen may be the same or different.

"Hydroxyl", "hydroxy", "hydroxyl group" or "hydroxyl group" refers to an —OH group.

"Alkoxyalky" or "alkoxyalkyl group" refers to an alkyl group substituted by an alkoxy group.

"Amino" or "amino group" refers to an —$NH_2$ group.

"Alkylamino" or "alkylamino group" refers to an alkyl-N(H)— group.

"Dialkylamino" or "dialkylamino" group refers to an (alkyl)(alkyl)N— group. In such a group the alkyl groups substituting the nitrogen may be the same or different.

"Carboxy", "carboxyl", "carboxy group" or "carboxyl group" refers to a —COOH group.

"Aminocarbonyl" or "aminocarbonyl group" refers to an $H_2N$—C(O)— group.

"N-alkylaminocarbonyl" or "N-alkylaminocarbonyl group" refers to an alkyl-NH—C(O)— group.

"N,N-dialkylaminocarbonyl" or "N,N-dialkylaminocarbonyl" refers to an (alkyl)(alkyl)N—C(O)— group. In such a group, the alkyl group substituents on the nitrogen may be the same or different.

"Aminosulfonyl" or "aminosulfonyl group" refers to an $H_2N$—$S(O)_2$— group.

"N-alkylaminosulfonyl" or "N-alkylaminosulfonyl group" refers to an (alkyl)N(H)—$S(O)_2$— group.

"N,N-dialkylaminosulfonyl" or N,N-dialkylaminosulfonyl group" refers to an (alkyl)(alkyl)N—$S(O)_2$— group. In such a group the alkyl group substituents on the nitrogen may be the same of different.

"N-[(alkyl)sulfonyl]amino" or "N-[(alkyl)sulfonyl]amino group" refers to an (alkyl)$S(O)_2$—NH— group.

"N-[(alkyl)sulfonyl]-N-alkylamino" or "N-[(alkyl)sulfonyl]-N-alkylamino group" refers to an (alkyl)$S(O)_2$—N(alkyl)-group. In such a group the alkyl group substituent on sulfur, and the alkyl group substituent on nitrogen may be the same or different.

"Aminoalkyl" or "aminoalkyl group" refers to an $H_2N$-alkyl-group.

"N-alkylaminoalkyl" or "N-alkylaminoalkyl group" refers to an (alkyl)N(H)-alkyl-group.

"N,N-dialkyl-aminoalkyl" or "N,N-dialkyl-aminoalkyl group" refers to an (alkyl)(alkyl)N-alkyl-group. In such a group the alkyl groups substituting the nitrogen may be the same of different.

"(Alkyl)$_2$phosphinyl" or "(alkyl)$_2$phosphinyl group" refers to a (alkyl)(alkyl)P(O)-group. In such a group, the alkyl substituents on phosphorus may be the same or different.

"Chemically stable" or "stable" refers to a compound that is sufficiently robust to be isolated to a useful degree of purity from a reaction mixture. The present invention is directed only to chemically stable compounds.

"Pharmaceutical composition" refers to a composition suitable for administration in medical or veterinary use.

When lists of alternative substituents include members which, owing to valency requirements, chemical stability, or other reasons, cannot be used to substitute a particular group, the list is intended to be read in context to include those members of the list that are suitable for substituting the particular group.

"Functionalized derivative" refers to a compound that contains at least one additional functional group as compared to a reference compound. An example of a functionalized derivative of benzene is bromobenzene. An example of a functionalized derivative of bromobenzene is 2-bromophenol. Functional groups include, but are not limited to, halogen, nitro, hydroxy, alkoxy, aryloxy, ketone, ester, amide, amino, alkylamino, alkyl, double bond, triple bond, alkoxyalkyl, aminoalkyl, haloalkyl, alkenyl, alkynyl, aryl, heteroaryl, cycloalkyl, heterocycloalkyl, pseudohalogen, alkylthio, sulfonyl, alkylsulfonyl, alkylaminosulfonyl, alkylcarbonyloxy, aminocarbonyloxy, alkylaminocarbonyloxy, alkylcarbonylamino, alkoxycarbonylamino, alkylsulfonylamino, aminocarbonylamino, and alkylaminocarbonylamino functional group, and derivatives of these and other functional groups in which a heteroatom is derivatized with a removable protecting group.

"Pharmaceutically acceptable" refers to physiologically tolerable materials, which do not typically produce an allergic or other untoward reaction, such as gastric upset, dizziness and the like, when administered to a mammal.

"Therapeutically effective amount" refers to an amount of a compound, or a pharmaceutically acceptable salt thereof, sufficient to inhibit, halt, or cause an improvement in a disorder or condition being treated in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

It should be appreciated that determination of proper dosage forms, dosage amounts, and routes of administration is within the level of ordinary skill in the pharmaceutical and medical arts, and is described below.

"Subject" refers to a member of the class Mammalia. Examples of mammals include, without limitation, humans, primates, chimpanzees, rodents, mice, rats, rabbits, horses, livestock, dogs, cats, sheep, and cows.

"Treatment" refers to the acute or prophylactic diminishment or alleviation of at least one symptom or characteristic associated or caused by a disorder being treated. For example, treatment can include diminishment of several symptoms of a disorder or complete eradication of a disorder.

"Administering" refers to the method of contacting a compound with a subject. Modes of "administering" include, but are not limited to, methods that involve contacting the compound intravenously, intraperitoneally, intranasally, transdermally, topically, via implantation, subcutaneously, parentally, intramuscularly, orally, systemically, and via adsorption.

II. Compounds

The present invention provides compounds of Formula I

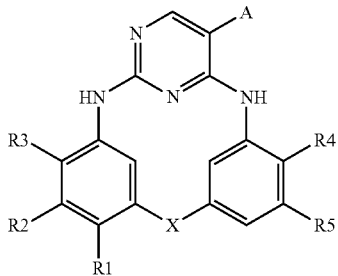

Formula I wherein:

A is H, cyano, F, Cl, Br, $CH_3$ or $CF_3$;

R1 is H, heterocyclyl, heteroaryl, carbocyclyl, aryl, $C_{1-6}$alkyl, $C_{1-6}$alkoxy, carbocyclyloxy, or $C_{1-6}$alkylamino, where, when R1 is a nitrogen containing heterocyclyl, the nitrogen may be substituted with $C_{1-6}$alkyl, hydroxy($C_{2-3}$) alkyl, dihydroxy ($C_3$)alkyl, $C_{1-6}$alkoxy($C_{2-3}$)alkyl, aminocarbonyl($C_{1-3}$)alkyl, N—($C_{1-6}$)alkylaminocarbonyl($C_{1-3}$) alkyl, N,N-di-($C_{1-6}$)alkylaminocarbonyl($C_{1-3}$)alkyl, where the ($C_{1-6}$)alkyl groups of N,N-di-($C_{1-6}$)alkylaminocarbonyl ($C_{1-3}$)alkyl may be the same or different, ($C_{1-6}$alkyl)sulfonyl ($C_{2-3}$)alkyl, ($C_{1-6}$ alkyl)sulfonyl, amino($C_{2-3}$)alkylcarbonyl, N—($C_{1-6}$alkyl)amino($C_{2-3}$)alkylcarbonyl, N,N-(di-$C_{1-6}$alkyl)amino($C_{2-3}$)alkylcarbonyl, where the alkyl groups of N,N-di-($C_{1-6}$alkyl)amino($C_{2-3}$)alkylcarbonyl may be the same or different, heteroaryl or heterocyclyl, and where, when R1 is heterocyclyl, heteroaryl, carbocyclyl, or aryl, such heterocyclyl, heteroaryl, carbocyclyl, or aryl may be unsubstituted, or substituted with one or two substituents independently selected from the group consisting of $C_{1-6}$alkyl, hydroxyl, hydroxy($C_{1-3}$)alkyl, $C_{1-6}$alkoxy, $C_{1-6}$alkoxy($C_{1-3}$)alkyl, aminocarbonyl($C_{1-3}$)alkyl, N—($C_{1-6}$)alkylaminocarbonyl($C_{1-3}$)alkyl, N,N-di-($C_{1-6}$) alkylaminocarbonyl($C_{1-3}$)alkyl, where the ($C_{1-6}$)alkyl groups of N,N-di-($C_{1-6}$)alkylaminocarbonyl($C_{1-3}$)alkyl may be the same or different, ($C_{1-6}$alkyl)sulfonyl($C_{1-3}$)alkyl, amino, ($C_{1-6}$)alkylamino, di-($C_{1-6}$)alkylamino, where the alkyl groups of di-($C_{1-6}$)alkylamino may be the same or different, ($C_{1-6}$)alkylsulfonyl, fluorine, carboxy, amino($C_{1-3}$)alkylcarbonyl, N—($C_{1-6}$alkyl)amino($C_{1-3}$)alkylcarbonyl, N,N-(di-$C_{1-6}$alkyl)amino($C_{1-3}$)alkylcarbonyl, where the alkyl groups of N,N-(di-$C_{1-6}$alkyl)amino($C_{1-3}$) alkylcarbonyl may be the same or different, and heterocyclyl, and where, when R1 is $C_{1-6}$alkyl, $C_{1-6}$alkoxy, or $C_{1-6}$alkylamino, the alkyl groups of such $C_{1-6}$alkyl, $C_{1-6}$alkoxy, or $C_{1-6}$alkylamino may be unsubstituted, or substituted with one, two or three substituents independently selected from the group consisting of heterocyclyl, heteroaryl, hydroxyl, amino, ($C_{1-6}$)alkylamino, di-($C_{1-6}$)alkylamino, where the alkyl groups of di-($C_{1-6}$)alkylamino may be the same or different, carboxy, aminocarbonyl, N—($C_{1-6}$)alkylaminocarbonyl, N,N-di-($C_{1-6}$)alkylaminocarbonyl, where the alkyl groups of N,N-di-($C_{1-6}$)alkylaminocarbonyl may be the same or different, aminosulfonyl, and $C_{1-6}$alkylsulfonyl;

R2 is H, heterocyclyl, heteroaryl, carbocyclyl, aryl, $C_{1-6}$alkyl, $C_{1-6}$alkoxy, or $C_{1-6}$alkylamino, where, when R2 is a nitrogen containing heterocyclyl, the nitrogen may be substituted with H, $C_{1-6}$alkyl, hydroxy($C_{2-3}$)alkyl, dihydroxy ($C_3$)alkyl, $C_{1-6}$alkoxy($C_{2-3}$) alkyl, aminocarbonyl($C_{1-3}$)alkyl, N—($C_{1-6}$)alkylaminocarbonyl($C_{1-3}$)alkyl, N,N-di-($C_{1-6}$)alkylaminocarbonyl($C_{1-3}$) alkyl, where the ($C_{1-6}$)alkyl groups of N,N-di-($C_{1-6}$) alkylaminocarbonyl($C_{1-3}$)alkyl may be the same or different, ($C_{1-6}$alkyl)sulfonyl($C_{2-3}$)alkyl, ($C_{1-6}$ alkyl)sulfonyl, amino ($C_{2-3}$)alkylcarbonyl, N—($C_{1-6}$alkyl)amino($C_{2-3}$)alkylcarbonyl, N,N-(di-$C_{1-6}$alkyl)amino($C_{2-3}$)alkylcarbonyl, where the alkyl groups of N,N-(di-$C_{1-6}$alkyl)amino($C_{2-3}$)alkylcarbonyl may be the same or different, heteroaryl or heterocyclyl, and where, when R2 is heterocyclyl, heteroaryl, carbocyclyl, or aryl, such heterocyclyl, heteroaryl, carbocyclyl, or aryl may be unsubstituted, or substituted with one or two substituents independently selected from the group consisting of $C_{1-6}$alkyl, hydroxyl, hydroxy($C_{1-3}$)alkyl, $C_{1-6}$alkoxy, $C_{1-6}$alkoxy($C_{1-3}$)alkyl, aminocarbonyl($C_{1-3}$)alkyl, N—($C_{1-6}$)alkylaminocarbonyl($C_{1-3}$)alkyl, N,N-di-($C_{1-6}$) alkylaminocarbonyl($C_{1-3}$)alkyl, where the ($C_{1-6}$)alkyl groups of N,N-di-($C_{1-6}$)alkylaminocarbonyl($C_{1-3}$)alkyl may be the same or different, ($C_{1-6}$alkyl)sulfonyl($C_{1-3}$)alkyl, amino, ($C_{1-6}$)alkylamino, di-($C_{1-6}$)alkylamino, where the alkyl groups of di-($C_{1-6}$)alkylamino may be the same or different, ($C_{1-6}$)alkylsulfonyl, fluoro, carboxy, amino($C_{1-3}$) alkylcarbonyl, N—($C_{1-6}$alkyl)amino($C_{1-3}$)alkylcarbonyl, N,N-(di-$C_{1-6}$alkyl)amino($C_{1-3}$)alkylcarbonyl, where the alkyl groups of N,N-(di-$C_{1-6}$alkyl)amino($C_{1-3}$)alkylcarbonyl may be the same or different, and heterocyclyl, and where, when R2 is $C_{1-6}$alkyl, $C_{1-6}$alkoxy, or $C_{1-6}$alkylamino, the alkyl groups of such $C_{1-6}$alkyl, $C_{1-6}$alkoxy, or $C_{1-6}$alkylamino may be unsubstituted, or substituted with one, two or three substituents independently selected from the group consisting of heterocyclyl, heteroaryl, hydroxyl, amino, ($C_{1-6}$)alkylamino, di-($C_{1-6}$)alkylamino, where the alkyl groups of di-($C_{1-6}$)alkylamino may be the same or different, carboxy, aminocarbonyl, N—($C_{1-6}$)alkylaminocarbonyl, N,N-di-($C_{1-6}$)alkylaminocarbonyl, where the alkyl groups of N,N-di-($C_{1-6}$)alkylaminocarbonyl may be the same or different, aminosulfonyl, and $C_{1-6}$alkylsulfonyl; or R1 and R2, together with the phenyl ring to which they are attached, form a five- to eight-membered monocarbocyclic or monoheterocyclic ring, where the ring so formed by R1 and R2, may be unsubstituted, or substituted with one to three substituents independently selected from the group consisting of $C_{1-6}$alkyl, amino($C_{1-3}$)alkyl, N—($C_{1-6}$alkyl)amino($C_{1-3}$)alkyl, N,N-di-($C_{1-6}$alkyl)amino($C_{1-3}$)alkyl, where the alkyl groups of N,N-di-($C_{1-6}$alkyl)amino($C_{1-3}$)alkyl may be the same or different, alkoxy($C_{1-6}$)alkyl, hydroxyl, hydroxy($C_{1-6}$)alkyl, ($C_{1-6}$alkyl)sulfonyl($C_{1-3}$)alkyl, heterocyclyl, amino, ($C_{1-6}$)alkylamino, di-($C_{1-6}$)alkylamino, where the alkyl groups of di-($C_{1-6}$)alkylamino may be the same or different, carboxy, aminocarbonyl, N—($C_{1-6}$)alkylaminocarbonyl, N,N-di-($C_{1-6}$)alkylaminocarbonyl, where the alkyl groups of N,N-di-($C_{1-6}$)alkylaminocarbonyl may be the same or different, aminocarbonyl($C_{1-3}$)alkyl, N—($C_{1-6}$)alkylaminocarbonyl($C_{1-3}$)alkyl, N,N-di-($C_{1-6}$)alkylaminocarbonyl($C_{1-3}$)alkyl, where the ($C_{1-6}$) alkyl groups of N,N-di-($C_{1-6}$)alkylaminocarbonyl($C_{1-3}$) alkyl may be the same or different, and aminosulfonyl;

R3 is H, $C_{1-6}$alkoxy, or Cl;

where at least one of R1 and R3 is other than H;

R4 and R5, independently, are H, $C_{1-6}$alkoxy, aminocarbonyl, N—($C_{1-6}$alkyl)aminocarbonyl, N,N-di-($C_{1-6}$alkyl)aminocarbonyl, where the alkyl groups of N,N-di-($C_{1-6}$alkyl)aminocarbonyl may be the same or different, ($C_{1-6}$alkyl)sulfonyl, aminosulfonyl, N—($C_{1-6}$alkyl)aminosulfonyl, N,N-di-($C_{1-6}$alkyl)aminosulfonyl, where the alkyl groups of N,N-di-($C_{1-6}$alkyl)aminosulfonyl may be the same or different, N—[($C_{1-6}$alkyl)sulfonyl]amino, N—[($C_{1-6}$alkyl)sulfonyl]-N—($C_{1-6}$alkyl)amino, where the alkyl groups of N—[($C_{1-6}$alkyl)sulfonyl]-N—($C_{1-6}$alkyl)amino may be same or different, ($C_{1-6}$alkyl)$_2$phosphinyl, where the alkyl groups of ($C_{1-6}$alkyl)$_2$phosphinyl may be the same or different, or heteroaryl, where, when R4 or R5 is heteroaryl, such heteroaryl may be unsubstituted, or substituted with one or two substituents independently selected from the group consisting of $C_{1-6}$alkyl, hydroxyl, hydroxy($C_{1-3}$)alkyl, $C_{1-6}$alkoxy, $C_{1-6}$alkoxy($C_{1-3}$)alkyl, aminocarbonyl($C_{1-3}$)alkyl, N—($C_{1-6}$)alkylaminocarbonyl($C_{1-3}$)alkyl, N,N-di-($C_{1-6}$)alkylaminocarbonyl($C_{1-3}$)alkyl, where the ($C_{1-6}$)alkyl groups of N,N-di-($C_{1-6}$)alkylaminocarbonyl-($C_{1-3}$)alkyl may be the same or different, ($C_{1-6}$alkyl)sulfonyl ($C_{1-3}$)alkyl, amino, ($C_{1-6}$)alkylamino, di-($C_{1-6}$)alkylamino, where the alkyl groups of di-($C_{1-6}$)alkylamino may be the same or different, ($C_{1-6}$alkyl)sulfonyl, fluorine, carboxy, aminocarbonyl, N—($C_{1-6}$)alkylaminocarbonyl, and N,N-di-($C_{1-6}$)alkylaminocarbonyl, where the alkyl groups of N,N-di-($C_{1-6}$)alkylaminocarbonyl may be the same or different, and where, when R4 or R5 is N—($C_{1-6}$alkyl)aminocarbonyl or $C_{1-6}$alkoxy, the alkyl groups of such N—($C_{1-6}$alkyl)aminocarbonyl or $C_{1-6}$alkoxy may be unsubstituted, or substituted by one, two or three substituents independently selected from the group consisting of heterocyclyl, hydroxyl, amino, ($C_{1-6}$)alkylamino, di-($C_{1-6}$)alkylamino, where the alkyl groups of di-($C_{1-6}$)alkylamino may be the same or different, cyano, carboxy, aminocarbonyl, N—($C_{1-6}$alkyl)aminocarbonyl, N,N-di-($C_{1-6}$alkyl)aminocarbonyl, where the alkyl groups of N,N-di-($C_{1-6}$alkyl) aminocarbonyl may be the same or different, or R4 and R5, together with the phenyl ring to which the are attached, form a five- to eight-membered monoheterocyclic ring, where the ring so-formed by R4 and R5 may be unsubstituted, or substituted with one or two substituents independently selected from the group consisting of $C_{1-6}$alkyl, amino($C_{1-3}$)alkyl, N—($C_{1-6}$alkyl)amino($C_{1-3}$)alkyl, N,N-di-($C_{1-6}$alkyl)amino($C_{1-3}$)alkyl, where the alkyl groups of N,N-di-($C_{1-6}$alkyl)amino($C_{1-3}$)alkyl may be the same or different, alkoxy($C_{1-6}$)alkyl, hydroxyl, hydroxy-($C_{1-6}$)alkyl, ($C_{1-6}$alkyl)sulfonyl, ($C_{1-6}$alkyl)sulfonyl($C_{1-3}$)alkyl, heterocyclyl, amino, ($C_{1-6}$)alkylamino, di-($C_{1-6}$)alkylamino, where the alkyl groups of di-($C_{1-6}$)alkylamino may be the same or different, carboxy, aminocarbonyl, N—($C_{1-6}$alkyl)aminocarbonyl, N,N-di-($C_{1-6}$alkyl)aminocarbonyl, where the alkyl groups of N,N-di-($C_{1-6}$alkyl) aminocarbonyl may be the same or different, aminosulfonyl ($C_{1-3}$)alkyl, N—($C_{1-6}$)alkylaminocarbonyl($C_{1-3}$)alkyl, N,N-di-($C_{1-6}$)alkylaminocarbonyl($C_{1-3}$)alkyl, where the ($C_{1-6}$) alkyl groups of N,N-di-($C_{1-6}$)alkylaminocarbonyl($C_{1-3}$) alkyl may be the same or different, and aminosulfonyl; and —X— is —CH=CH—, —CH$_2$CH$_2$—, —NH—CO—, —CONH— or —(CH(OH))$_2$—; or pharmaceutically acceptable salts thereof.

A preferred embodiment of the present invention provides compounds of Formula I wherein A is Cl, CH$_3$ or CF$_3$. In a more preferred embodiment, A is Cl.

Another preferred embodiment of the present invention provides compounds of Formula I wherein R1 is $C_{1-6}$alkylamino, $C_{1-6}$alkoxy where $C_{1-6}$alkoxy is substituted by heterocyclyl, heterocyclyl, or R1 and R2, together with the phenyl ring to which they are attached, form a five- to eight-membered monocarbocyclic ring. In a more preferred embodiment, R1 is $C_{1-6}$alkoxy where $C_{1-6}$alkoxy is substituted by heterocyclyl, or heterocyclyl. In a most preferred embodiment, R1 is heterocyclyl.

Another preferred embodiment of the present invention provides compounds of Formula I wherein R2 is H, or R1 and R2, together with the phenyl ring to which they are attached, form a five- to eight-membered monocarbocyclic ring. In a more preferred embodiment R2 is H.

Another preferred embodiment of the present invention provides compounds of Formula I wherein R3 is $C_{1-6}$alkoxy or H.

Another preferred embodiment of the present invention provides compounds of Formula I wherein R4 is H, $C_{1-6}$alkoxy, N—($C_{1-6}$alkyl)aminocarbonyl, ($C_{1-6}$alkyl)sulfonyl, N—[($C_{1-6}$alkyl)sulfonyl]-N—($C_{1-6}$alkyl)amino, where the alkyl groups of N—[($C_{1-6}$alkyl)sulfonyl]-N—($C_{1-6}$alkyl)amino may be the same or different, or heteroaryl. In a more preferred embodiment, R4 is H, $C_{1-6}$alkoxy, N—($C_{1-6}$alkyl)aminocarbonyl, ($C_{1-6}$alkyl)sulfonyl, or N—[($C_{1-6}$alkyl)sulfonyl]-N—($C_{1-6}$alkyl)amino, where the alkyl groups of N—[($C_{1-6}$alkyl)sulfonyl]-N—($C_{1-6}$alkyl)amino may be the same or different.

Another preferred embodiment of the present invention provides compounds of Formula I wherein R5 is H, N—($C_{1-6}$alkyl)aminosulfonyl, or N,N-di-($C_{1-6}$alkyl)aminosulfonyl, where the alkyl groups of N,N-di-($C_{1-6}$alkyl) aminosulfonyl may be the same or different.

In another preferred embodiment, —X— is —CH=CH— or —CH$_2$CH$_2$—.

A particularly preferred embodiment of the present invention provides compounds of Formula I wherein:

A is Cl, CH$_3$ or CF$_3$;

R1 is C$_{1-6}$alkylamino, C$_{1-6}$alkoxy where C$_{1-6}$alkoxy is substituted by heterocyclyl, heterocyclyl, or R1 and R2, together with the phenyl ring to which they are attached, form a five- to eight-membered monocarbocyclic ring;

R2 is H, or R1 and R2, together with the phenyl ring to which they are attached, form a five- to eight-membered monocarbocyclic ring;

R3 is C$_{1-6}$alkoxy or H;

R4 is H, C$_{1-6}$alkoxy, N—(C$_{1-6}$alkyl)aminocarbonyl, (C$_{1-6}$alkyl)sulfonyl, N—[(C$_{1-6}$alkyl)sulfonyl]-N—(C$_{1-6}$alkyl)amino, where the alkyl groups of N—[(C$_{1-6}$alkyl)sulfonyl]-N—(C$_{1-6}$alkyl)amino may be the same or different, or heteroaryl;

R5 is H, N—(C$_{1-6}$alkyl)aminosulfonyl, or N,N-di-(C$_{1-6}$alkyl)aminosulfonyl, where the alkyl groups of N,N-di-(C$_{1-6}$alkyl)aminosulfonyl may be the same or different; and X is —CH=CH— or —CH$_2$CH$_2$—.

In other preferred embodiments, the present invention provides any of the compounds as described in the Examples.

The present invention provides pharmaceutically acceptable salts of compounds of Formula I. Pharmaceutically acceptable acid addition salts of the compounds of Formula I include, but are not limited to, salts derived from inorganic acids such as hydrochloric, nitric, phosphoric, sulfuric, hydrobromic, hydriodic, and phosphorus, as well as the salts derived from organic acids, such as aliphatic mono- and dicarboxylic acids, phenyl-substituted alkanoic acids, hydroxy alkanoic acids, alkanedioic acids, aromatic acids, and aliphatic and aromatic sulfonic acids. Such salts thus include, but are not limited to, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, and methanesulfonate. Also contemplated are the salts of amino acids such as arginate, gluconate, galacturonate, and the like; see, for example, Berge et al., "Pharmaceutical Salts," J. of Pharmaceutical Science, 1977; 66:1-19.

The acid addition salts of the basic compounds may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are in general equivalent to their respective free base for purposes of the present invention.

Pharmaceutically acceptable base addition salts of compounds of Formula I are formed with metals or amines, such as alkali and alkaline earth metal hydroxides, or of organic amines. Examples of metals used as cations include, but are not limited to, sodium, potassium, magnesium, and calcium. Examples of suitable amines include, but are not limited to, N,N'-dibenzylethylenediamine, chloroprocaine, choline, diethanolamine, ethylenediamine (ethane-1,2-diamine), N-methylglucamine, and procaine; see, for example, Berge et al., supra., 1977.

The base addition salts of acidic compounds may be prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are in general equivalent to their respective free acid for purposes of the present invention.

Some of the compounds in the present invention may exist as stereoisomers, including enantiomers, diastereomers, and geometric isomers. Geometric isomers include compounds of the present invention that have alkenyl groups, which may exist as entgegen or zusammen conformations, in which case all geometric forms thereof, both entgegen and zusammen, cis and trans, and mixtures thereof, are within the scope of the present invention. Some compounds of the present invention have carbocyclyl groups, which may be substituted at more than one carbon atom, in which case all geometric forms thereof, both cis and trans, and mixtures thereof, are within the scope of the present invention. All of these forms, including (R), (S), epimers, diastereomers, cis, trans, syn, anti, (E), (Z), tautomers, and mixtures thereof, are contemplated in the compounds of the present invention.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention.

III. Pharmaceutical Compositions

The present invention further provides pharmaceutical compositions comprising a compound of the present invention (e.g., a compound of Formula I or a pharmaceutically acceptable salt thereof), together with a pharmaceutically acceptable carrier, diluent, or excipient therefor. The pharmaceutical composition may contain two or more compounds of the present invention (i.e., two or more compounds of the present invention may be used together in the pharmaceutical composition). Preferably, the pharmaceutical composition contains a therapeutically effective amount of at least one compound of the present invention. In another embodiment, these compositions are useful in the treatment of an ALK-, FAK- or JAK2-mediated disorder or condition. The compounds of the invention can also be combined in a pharmaceutical composition that also comprises compounds that are useful for the treatment of cancer or another ALK-, FAK- or JAK2-mediated disorder.

A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Preferably, a compound of the present invention will cause a decrease in symptoms or a disease indicia associated with an ALK-, FAK- or JAK2-mediated disorder as measured quantitatively or qualitatively.

For preparing a pharmaceutical composition from a compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component (i.e., compound of the present invention). In tablets, the active component is mixed with the carrier having the necessary binding properties in suitable proportions and compacted in the shape and size desired.

The powders and tablets contain from 1% to 95% (w/w) of the active compound (i.e., compound of the present invention). In another embodiment, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg, or from 1% to 95% (w/w) of a unit dose, according to the particular application and the potency of the active component. The composition can, if desired, also contain other compatible therapeutic agents.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington: The Science and Practice of Pharmacy,* 20th ed., Gennaro et al. Eds., Lippincott Williams and Wilkins, 2000).

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

The dose administered to a subject, in the context of the present invention, should be sufficient to effect a beneficial therapeutic response in the subject over time. The dose will be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 10 mg/kg for a typical subject. Many different administration methods are known to those of skill in the art.

For administration, compounds of the present invention can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

IV. Methods of Treatment

In another aspect, the present invention provides a method of treating a subject suffering from an ALK-, FAK- or JAK2-mediated disorder or condition comprising: administering to the subject a therapeutically effective amount of a compound of Formula I or a pharmaceutically acceptable salt form thereof. In another aspect, the present invention provides a compound of Formula I or a pharmaceutically acceptable salt form thereof for use in treating a subject suffering from an ALK-, FAK- or JAK2-mediated disorder or condition. Preferably, the compound of Formula I or a pharmaceutically acceptable salt form thereof is administered to the subject in a pharmaceutical composition comprising a pharmaceutically acceptable carrier. In another aspect, the present invention provides a pharmaceutical composition comprising a compound of Formula I or a pharmaceutically acceptable salt form thereof for use in treating a subject suffering from an ALK-, FAK- or JAK2-mediated disorder or condition. In another embodiment, the ALK-, FAK- or JAK2-mediated condition or disorder is cancer. In another embodiment, the ALK-, FAK- or JAK2-mediated condition is selected from anaplastic large cell lymphoma, inflammatory myofibroblastic tumor, glioblastoma, and other solid tumors. In another embodiment, the ALK-, FAK- or JAK2-mediated condition is selected from colon cancer, breast cancer, renal cancer, lung cancer, hemangioma, squamous cell myeloid leukemia, melanoma, glioblastoma, and astrocytoma.

The ALK-, FAK- or JAK2-mediated disorder or condition can be treated prophylactically, acutely, and chronically using compounds of the present invention, depending on the nature of the disorder or condition. Typically, the host or subject in each of these methods is human, although other mammals can also benefit from the administration of a compound of the present invention.

In another embodiment, the present invention provides a method of treating a proliferative disorder in a subject in need thereof, comprising administering to the subject a therapeutically effective amount of a compound of Formula I or a pharmaceutically acceptable salt form thereof. In another aspect, the present invention provides a compound of Formula I or a pharmaceutically acceptable salt form thereof for use in treating a proliferative disorder in a subject in need thereof. Preferably, the compound of Formula I or a pharmaceutically acceptable salt form thereof is administered to the subject in a pharmaceutical composition comprising a pharmaceutically acceptable carrier. In another aspect, the present invention provides a pharmaceutical composition comprising a compound of Formula I or a pharmaceutically acceptable salt form thereof for use in treating a proliferative disorder in a subject. In certain embodiments, the proliferative disorder is ALK-, FAK- or JAK2-mediated. In certain embodiments, the proliferative disorder is cancer. In certain embodiments, the proliferative disorder is selected from anaplastic large cell lymphoma, inflammatory myofibroblastic tumor, glioblastoma, and other solid tumors. In certain embodiments, the prolifereative disorder is selected from colon cancer, breast cancer, renal cancer, lung cancer, hemangioma, squamous cell myeloid leukemia, melanoma, glioblastoma, and astrocytoma.

The proliferative disorder can be treated prophylactically, acutely, and chronically using compounds of the present invention, depending on the nature of the disorder or condition. Typically, the host or subject in each of these methods is human, although other mammals can also benefit from the administration of a compound of the present invention.

In therapeutic applications, the compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. In another embodiment, the compounds of the present invention are delivered orally. The compounds can also be delivered rectally, bucally or by insufflation.

The compounds utilized in the pharmaceutical method of the invention can be administered at the initial dosage of about 0.001 mg/kg to about 100 mg/kg daily. In another embodiment, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

V. Chemistry

Unless otherwise indicated, all reagents and solvents were obtained from commercial sources and used as received. $^1$H NMRs were obtained on a Bruker Avance at 400 MHz in the solvent indicated with tetramethylsilane as an internal standard. Analytical HPLC was run using a Zorbax RX-C8, 5×150 mm column eluting with a mixture of acetonitrile and water containing 0.1% trifluoroacetic acid with a gradient of 10-100%. LCMS results were obtained from a Bruker Esquire 2000 Mass Spec with the Agilent 1100 HPLC equipped with an Agilent Eclipse XDB-C8, 2×30 mm 3.5 micron column. The column was at room temperature, with a run time of five (5) minutes, a flow rate of 1.0 mL/min, and a solvent mixture of 10% (0.1% formic acid/water): 100% (acetonitrile/0.1% formic acid). Automated normal phase column chromatography was performed on a CombiFlash Companion (ISCO, Inc.). Reverse phase preparative HPLC was performed on a Gilson GX-281 equipped with Gilson 333 and 334 pumps using a Phenomenex 00F-4454-00-AX Gemini-NX 5µ C18 column. Melting points were taken on a Mel-Temp apparatus and are uncorrected.

Synthesis

The compounds of the present invention can be prepared in a number of ways well known to one skilled in the art of organic synthesis. The compounds of the present invention can be synthesized using the methods described below as well as using methods known to one skilled in the art of organic chemistry or variations thereon as appreciated by those skilled in the art. The preferred methods include, but are not limited to or by, those described below. Unless otherwise stated, compounds are of commercial origin or readily synthesized by standard methods well known to one skilled in the art of organic synthesis.

The compounds of this invention may be prepared using the reactions and techniques described in this section. The reactions are performed in solvents appropriate to the reagents, and materials employed are suitable for the transformations being effected. Also, in the description of the synthetic methods below, it is to be understood that all proposed reaction conditions, including choice of solvent, reaction atmosphere, reaction temperature, duration of experiment and workup procedures are chosen to be conditions standard for that reaction which should be readily recognized by one skilled in the art of organic synthesis.

It is understood that the examples and embodiments described herein are for illustrative purposes only and that various modifications or changes in light thereof will be suggested to persons skilled in the art and are to be included within the spirit and purview of this application and the scope of the appended claims. Specific chemical transformations are listed in the ensuing schemes and one skilled in the art appreciates that a variety of different reagents may be used in place of those listed. Common replacements for such reagents can be found in, but not limited to, texts such as "Encyclopedia of Reagents for Organic Synthesis" Leo A. Paquette, John Wiley & Son Ltd (1995) or "Comprehensive Organic Transformations: A Guide to Functional Group Preparations" Richard C. Larock. Wiley-VCH and "Strategic Applications of Named Reactions in Organic Synthesis" Kurti and Czako, Elsevier, 2005 and references therein.

Compounds of the present invention, wherein X is —CH=CH— or —CH$_2$CH$_2$— may be prepared according to Scheme I.

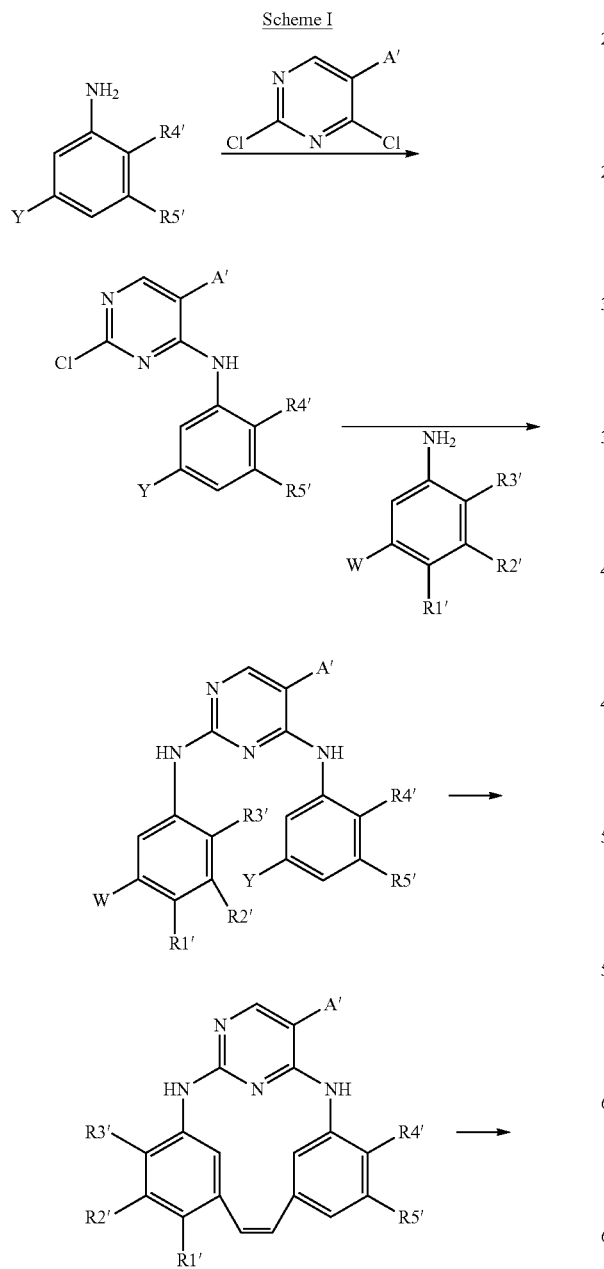

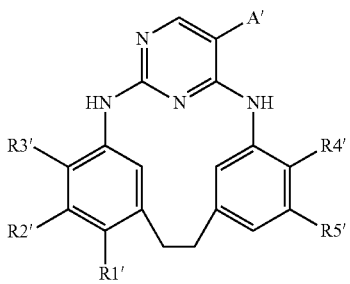

In Scheme I, R1', R2', R3', R4', R5' and A, are R1, R2, R3, R4, R5 and A, respectively, as defined herein, or are synthetic precursor moieties thereto, that may be converted to R1, R2, R3, R4, R5 and A, respectively, by methods known in the art, or as disclosed herein. In Scheme I, one of W or Y is a vinyl group, and the other is bromo.

In Scheme I, an aniline is coupled with a chloropyrimidine, in the presence of base, to form a phenylaminopyrimidine. This, in turn, is coupled with another aniline, in an alcohol, in the presence of an acid catalyst, to form a disubstituted pyrimidine. The olefin-containing macrocycle is formed under Heck reaction conditions, for example in the presence of palladium acetate, tri-o-tolyl phosphine and triethyl amine. The macrocyclic olefin is then reduced to afford the compound of Formula I wherein X is —CH$_2$—CH$_2$—.

EXAMPLES

Example 1

6,13,19-Triaza-4-chloro-7,14$^{1,3}$-dibenzena-1$^{2,4}$-pyrimidinacyclodocosaph-12-one

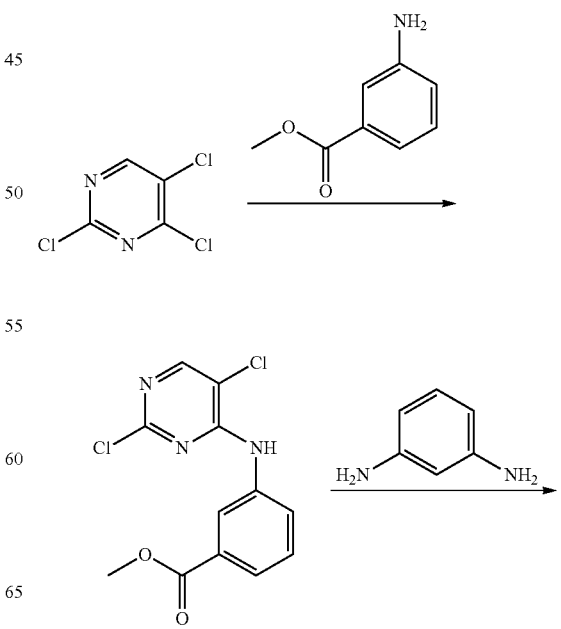

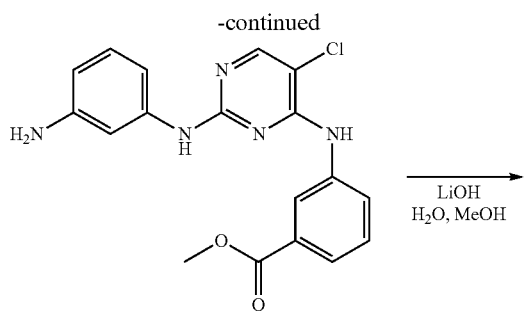

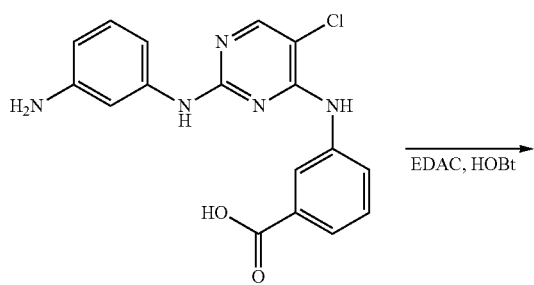

Example 1a 3-(2,5-Dichloro-pyrimidin-4-ylamino)-benzoic acid methyl ester

A mixture of 2,4,5-Trichloro-pyrimidine (840 mg, 4.58 mmol), 3-amino-benzoic acid methyl ester (690 mg, 4.6 mmol), potassium carbonate ($K_2CO_3$) (1.9 g, 14 mmol) in dimethylformamide (DMF) (20 mL) were stirred at 80° C. for 4 hours. After cooling to room temperature, the mixture was treated with water and the resulting solid was filtered and rinsed liberally with water. After air drying there remained 770 mg of crude product 3-(2,5-Dichloro-pyrimidin-4-ylamino)-benzoic acid methyl ester, which was used for the subsequent step without further manipulation.

Example 1b

3-[2-(3-Amino-phenylamino)-5-chloro-pyrimidin-4-ylamino]-benzoic acid methyl ester 3-(2,5-Dichloro-pyrimidin-4-ylamino)-benzoic acid methyl ester (435 mg, 1.46 mmol), m-phenylenediamine (100 mg, 1 mmol), and 4M hydrogen chloride (HCl) in 1,4-dioxane (300 mL) were combined in methanol (10 mL) and warmed to reflux under an inert atmosphere for 5 hours. The resulting solid was filtered off, and the filtrate concentrated under reduced pressure. The residue from the filtrate was dissolved in dimethylsulfoxide (DMSO) and purified via preparative HPLC. The desired fractions were partitioned between saturated aqueous sodium bicarbonate ($NaHCO_3$) and ethyl acetate (EtOAc). The organic phase was dried over $Na_2SO_4$, filtered, and concentrated under reduced pressure to yield 170 mg (40%) of desired 3-[2-(3-Amino-phenylamino)-5-chloro-pyrimidin-4-ylamino]-benzoic acid methyl ester, which was used without further manipulation. LC: 95%; LC/MS: M+H=370.1.

Example 1c

3-[2-(3-Amino-phenylamino)-5-chloro-pyrimidin-4-ylamino]-benzoic acid. Lithium hydroxide (39 mg, 1.6 mmol) in water was added to a mixture of 3-[2-(3-Amino-phenylamino)-5-chloro-pyrimidin-4-ylamino]-benzoic acid methyl ester (120 mg, 0.32 mmol) in methanol (25 mL) and the mixture was warmed at 55° C. for 16 hours. The mixture was concentrated under reduced pressure, then treated with water (2 mL) followed by 1N HCl (1.7 mL). The mixture was concentrated under reduced pressure and the residue was used for the subsequent step without further manipulation. M+H=356.2.

Example 1d 6,13,19-Triaza-4-chloro-7,14$^{1,3}$-dibenzena-1$^{2,4}$-pyrimidinacyclodocosaph-12-one. At room temperature N-(3-Dimethylaminopropyl)-N' ethylcarbodiimide hydrochloride (130 mg, 0.67 mmol) was added to a mixture of 3-[2-(3-Amino-phenylamino)-5-chloro-pyrimidin-4-ylamino]-benzoic acid (110 mg, 0.322 mmol) and hydroxybenzotriazole (65 mg, 0.48 mmol) in DMF (5 mL). After 16 hours the reaction mixture was concentrated under reduced pressure and the residue purified by Gilson reverse phase HPLC. Solid precipitated from the purified fractions and was filtered to yield 19 mg of 6,13,19-Triaza-4-chloro-7,14$^{1,3}$-dibenzena-1$^{2,4}$-pyrimidinacyclodocosaph-12-one as a white solid. The filtrate was lyophilized to yield a second 42 mg portion of 6,13,19-Triaza-4-chloro-7,14$^{1,3}$-dibenzena-1$^{2,4}$-pyrimidinacyclodocosaph-12-one. LC: 100%; LC/MS: M+H=338.17; 1H NMR (DMSO-d6) δ 9.82 (s, 1H, exchangeable), 9.28 (s, 1H, exchangeable), 9.25 (s, 1H, exchangeable), 8.07 (s, 1H), 7.96 (S, 1H), 7.76 (s, 1H), 7.25-7.21 (m, 1H), 7.09-7.00 (m, 3H), 6.73-6.71 (d, 1H), 6.68-6.66 (d, 1H).

Example 2

(14Z)-6-Chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene

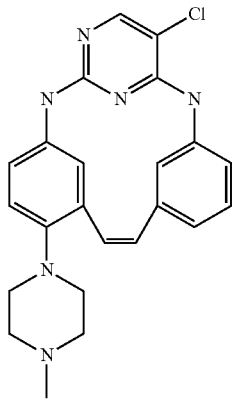 [SMILES: CN1CCN(c2ccc3cc2CCc2cccc(c2)Nc2nc(ncc2Cl)N3)CC1]

Example 2a

N(2)-[3-Bromo-4-(4-methyl-piperain-1-yl)-phenyl]-5-chloro-N(4)-(3-vinyl-phenyl)-pyrimidine-2,4-diamine N(2)-[3-Bromo-4-(4-methyl-piperain-1-yl)-phenyl]-5-chloro-N(4)-(3-vinyl-phenyl)-pyrimidine-2,4-diamine was prepared in a similar manner as N(2)-[3-Bromo-4-(4-methyl-piperazin-1-yl)-phenyl]-5-chloro-N(4)-(2-methoxy-5-vinyl-phenyl)-pyrimidine-2,4-diamine (prepared according to Example 13d) after substituting (2,5-Dichloro-pyrimidin-4-yl)-3-vinyl-phenyl)-amine for (2,5-dichloro-pyrimidin-4-yl)-(2-methoxy-5-vinyl-phenyl)-amine and after substituting 1-methoxy-2-propanol as the preferred solvent. Also the reaction was warmed to 110° C. and the workup varied in that the resulting reaction solution was concentrated under reduced pressure and the residue was partitioned between CHCl$_3$ and saturated aqueous NaHCO$_3$. The organic phase was dried over Na$_2$SO$_4$, filtered, and concentrated under reduced pressure. The residue was triturated with CH$_3$CN, filtered, and rinsed with a small amount of CH$_3$CN. The desired product N(2)-[3-Bromo-4-(4-methyl-piperain-1-yl)-phenyl]-5-chloro-N(4)-(3-vinyl-phenyl)-pyrimidine-2,4-diamine was isolated in 62% as a tan solid, mp 149-153° C. LC: 93%; LC/MS: M+H=501.0; $^1$H NMR (DMSO-d6) δ 9.35 (s, 1H), 8.85 (s, 1H), 8.16 (s, 1H), 7.83 (s, 1H), 7.70 (s, 1H), 7.61-7.58 (m, 2H), 7.37-7.33 (t, 1H), 7.28-7.26 (d, 1H), 6.97-6.95 (d, 1H), 6.75-6.68 (m, 1H), 5.81-5.77 (d, 1H), 5.27-5.24 (d, 1H), 2.87 (s, 4H), 2.46 (s, 4H), 2.23 (s, 3H).

Example 2b (14Z)-6-Chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene (14Z)-6-Chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene was prepared in a similar manner as Methyl (14Z)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene-10-carboxylate (prepared as in Example 16c) after substituting N(2)-[3-Bromo-4-(4-methyl-piperain-1-yl)-phenyl]-5-chloro-N(4)-(3-vinyl-phenyl)-pyrimidine-2,4-diamine for 4-Bromo-2-(5-chloro-2-[4-(4-methyl-piperazin-1-yl)-3-vinyl-phenylamino]-pyrimidin-4-ylamino)-benzoic acid methyl ester. The desired product (14Z)-6-Chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene was isolated in 75% yield as an off white solid. LC: 92%, LC/MS: M+H=419.1.

A 25 mg sample of the 92% pure material was further purified via preparative HPLC to return 17 mg of (14Z)-6-Chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene as a TFA salt white lyophylate, which was the sample used for biological testing. LC: 100%; LC/MS: M+H=419.1; $^1$H NMR (DMSO-d6) δ 9.58 (bs, 1H), 9.29 (s, 1H), 9.12 (s, 1H), 8.61 (s, 1H), 8.45-8.44 (d, 1H), 8.12 (s, 1H), 7.29-7.25 (t, 1H), 7.20-7.18 (d, 1H), 7.02-6.97 (m, 3H), 6.83-6.80 (d, 1H), 6.75-6.72 (d, 1H), 3.74 (bs, H$_2$O), 3.54-3.51 (d, 2H), 3.29-3.22 (m, 4H), 2.93-2.89 (m, 5H).

Example 3

6-Chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

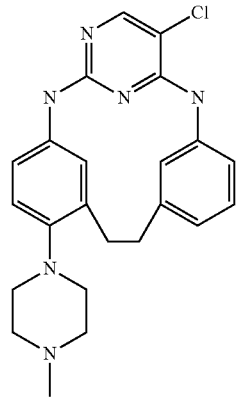

6-Chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene (prepared according to Example 5) after substituting (14Z)-6-Chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene. The desired product 6-Chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene was isolated in 63% yield as a TFA salt, white lyophylate. LC: 99%, M+H=421.0; $^1$H NMR (DMSO-d6) δ 9.7 (bs, 1H), 9.40 (s, 1H), 9.27 (s, 1H), 8.14 (s, 1H), 8.03-8.02 (d, 1H), 7.82 (s, 1H), 7.26-7.22 (t, 1H), 7.07-7.05 (d, 1H), 7.02-7.01 (d, 1H), 7.00 (s, 1H), 6.93-6.90 (m, 1H), 3.52-3.49 (d, 2H), 3.26-3.2 (m, 2H), 3.09-3.05 (d, 2H), 2.99-2.90 (m, 9H).

Example 4

(14Z)-6-Chloro-10-(2-methanesulfonyl-methyl-amino)-17-(4-methylpiperazin-1-yl)-19-methoxy-2, 4,8,22-tetraazatetracyclo[14.3.1.1$^{3,7}$.1$^{9,13}$]docosa-1 (20),3(22),4,6,9(21),10,12,14,16,18-decaene

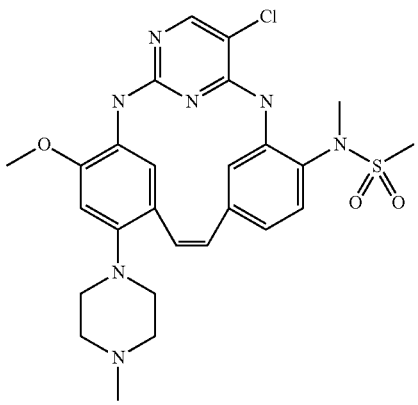

Example 4a

N-(4-Bromo-2-nitro-phenyl)-methanesulfonamide

Potassium nitrate (0.34 g, 3.36 mmol) was added neat to a 0° C. solution of N-(4-bromo-phenyl)-methanesulfonamide (0.75 g, 3.0 mmol) in acetonitrile (CH$_3$CN) (20 mL) and trifluoroacetic anhydride (2.6 mL). After 2 hours the 0° C. reaction mixture was slowly treated with saturated aqueous NaHCO$_3$ until the reaction mixture was basic. The resulting solid was filtered and rinsed liberally with ice cold water. After air drying there remained 0.75 g (85%) of desired N-(4-Bromo-2-nitro-phenyl)-methanesulfonamide as a yellow solid, which was used for the subsequent step without further manipulation. LC: 98%, $^1$H NMR (DMSO-d6) δ 9.88 (s, 1H), 8.23 (s, 1H), 7.95-7.93 (d, 1H), 7.59-7.57 (d, 1H), 3.152 (s, 3H).

Example 4b

N-(4-Bromo-2-nitro-phenyl)-N-methyl-methanesulfonamide

Methyl iodide (430 µL, 6.9 mmol) was added to a mixture of N-(4-Bromo-2-nitro-phenyl)-methanesulfonamide (0.68 g, 2.3 mmol) and K$_2$CO$_3$ (1.3 g, 9.2 mmol) in DMF (10 mL). After 16 hours the reaction mixture was treated with water (20 mL). The resulting solid was filtered, rinsed liberally with water, and air dried to yield 0.68 g (96%) of desired N-(4-Bromo-2-nitro-phenyl)-N-methyl-methanesulfonamide as a white solid, which was used for the subsequent step without further manipulation. LC: 100%, $^1$H NMR (DMSO-d6) δ 8.23 (s, 1H), 8.02-8.00 (d, 1H), 7.80-7.77 (d, 1H), 3.26 (s, 3H), 3.06 (s, 3H).

Example 4c

N-Methyl-N-(2-nitro-4-vinyl-phenyl)-methanesulfonamide

N-Methyl-N-(2-nitro-4-vinyl-phenyl)-methanesulfonamide was prepared in a similar manner as 2-Methoxy-5-vinyl-phenylamine (prepared according to Example 13d) after substituting N-(4-Bromo-2-nitro-phenyl)-N-methyl-methanesulfonamide for 5-bromo-2-methoxy-phenylamine. The workup was varied in that after concentration of the reaction mixture, the residue was partitioned between EtOAc (2×) and water. The combined organic phases were dried over magnesium sulfate (MgSO$_4$), filtered, and the crude product in the filtrate was adsorbed directly onto silica gel under reduced pressure. The residue was purified via normal phase chromatography (EtOAc/Hexane eluent) to give desired N-Methyl-N-(2-nitro-4-vinyl-phenyl)-methanesulfonamide in 69% yield. LC: 98%; LC/MS: M+23=279.0.

Example 4d

N-(2-Amino-4-vinyl-phenyl)-N-methyl-methanesulfonamide

N-(2-Amino-4-vinyl-phenyl)-N-methyl-methanesulfonamide was prepared in a similar manner as 4-(4-Methyl-piperazin-1-yl)-3-vinyl-phenylamine (prepared according to Example 9e) after substituting N-Methyl-N-(2-nitro-4-vinyl-phenyl)-methanesulfonamide for 1-Methyl-4-(4-nitro-2-vinyl-phenyl)-piperazine. The workup was similar, except EtOAc was used for extractions rather than chloroform (CHCl$_3$). Compound N-(2-Amino-4-vinyl-phenyl)-N-methyl-methanesulfonamide was recovered in 99% yield as a brown oil and used directly after workup for subsequent steps without further manipulation. LC: 97%; LC/MS: M+23=249.0; $^1$H NMR (CDCl$_3$-d3) δ 7.11-7.09 (d, 1H), 6.85-6.83 (m, 2H), 6.66-6.59 (m, 1H), 5.74-5.70 (d, 1H), 5.29-5.27 (d, 1H), 4.24 (bs, 2H), 3.25 (s, 3H), 2.98 (s, 3H).

Example 4e

1-Bromo-2-fluoro-4-methoxy-5-nitro-benzene (10c) and 1-Bromo-4-fluoro-2-methoxy-5-nitro-benzene 1-Bromo-2,4-difluoro-5-nitro-benzene (960 mg, 4.0 mmol) was dissolved in MeOH (20 mL) was cooled to 0° C. and treated with 0.5M Sodium Methoxide in MeOH solution (8.1 mL, 4 mmol). After 2 hours the reaction solution was concentrated under reduced pressure and the residue was partitioned between EtOAc and water. The organic phase was dried over sodium sulfate (Na$_2$SO$_4$), filtered, and concentrated under reduced pressure to give 833 mg (83%) of yellowish oil. 1H NMR spectral analysis supported that the product was a mixture of 1-Bromo-2-fluoro-4-methoxy-5-nitro-benzene and 1-Bromo-4-fluoro-2-methoxy-5-nitro-benzene (~1:2 ratio). The assignments of the respective regioisomers were determined based on further analysis of a purified 1-Bromo-2-fluoro-4-methoxy-5-nitro-benzene analog, generated from the subsequent steps to this reaction. $^1$H NMR (DMSO-d6) δ 8.41-8.39 (d, 0.63H), 8.36-8.34 (d, 0.26H), 7.57-7.54 (d, 0.30H), 7.45-7.42 (d, 0.70H), 4.01 (s, 2.2H), 3.95 (s, 0.9H).

Example 4f

1-(2-Bromo-5-methoxy-4-nitro-phenyl)-4-methyl-piperazine

The 833 mg mixture of 1-Bromo-2-fluoro-4-methoxy-5-nitro-benzene and 1-Bromo-4-fluoro-2-methoxy-5-nitro-benzene was treated at room temperature with 1-methyl-piperazine (10 mL, 100 mmol). After 3 hours the mixture was diluted with water and then extracted with EtOAc. The organic phase was dried over MgSO$_4$, filtered, and concentrated under reduced pressure to yield 1.13 g of oil. This material was purified via preparative HPLC to separate 1-(2-Bromo-5-methoxy-4-nitro-phenyl)-4-methyl-piperazine from its respective regioisomer. The purified fractions of 1-(2-Bromo-5-methoxy-4-nitro-phenyl)-4-methyl-piperazine from the HPLC were partitioned between EtOAc and saturated aqueous NaHCO$_3$. The organic phase was dried over Na$_2$SO$_4$, filtered, and concentrated under reduced pressure to give 0.26 g (24%) of desired 1-(2-Bromo-5-methoxy-4-nitro-phenyl)-4-methyl-piperazine as an oil, which crystallized upon sitting. Free basing of the purified regioisomer 1-(4-Bromo-5-methoxy-2-nitro-phenyl)-4-methyl-piperazine, resulted in a return of 0.56 g (51%) of this side product. Preliminary analysis of 1-(2-Bromo-5-methoxy-4-nitro-phenyl)-4-methyl-piperazine: LC: 100%, LC/MS: M+H=330.0.

Example 4g

5-Bromo-2-methoxy-4-(4-methyl-piperazin-1-yl)-phenylamine

5-Bromo-2-methoxy-4-(4-methyl-piperazin-1-yl)-phenylamine was prepared in a similar manner as 3-Bromo-4-(2-pyrrolidin-1-yl-ethoxy)-phenylamine (prepared according to Example 22b) after substituting 1-(2-Bromo-5-methoxy-4-nitro-phenyl)-4-methyl-piperazine for 1-[3-(2-bromo-4-nitro-phenoxy)-propyl]-pyrrolidine. After workup a mass return of 100% was returned, but $^1$H NMR and LC/MS confirmed the crude to be 80% 5-Bromo-2-methoxy-4-(4-methyl-piperazin-1-yl)-phenylamine, with a 20% impurity of the des-Br analog of 5-Bromo-2-methoxy-4-(4-methyl-piperazin-1-yl)-phenylamine This crude material was used for subsequent reactions without further manipulation. It was also found that 5-Bromo-2-methoxy-4-(4-methyl-piperazin-1-yl)-phenylamine could be prepared pure in 96% yield cleanly by following a procedure similar to 4-(4-Methyl-piperazin-1-yl)-3-vinyl-phenylamine (prepared according to Example 9e) after substituting 1-(2-Bromo-5-methoxy-4-nitro-phenyl)-4-methyl-piperazine for 1-Methyl-4-(4-nitro-2-vinyl-phenyl)-piperazine. LC/MS: M+H=302.0; $^1$H NMR (CDCl$_3$-d3) δ 6.93 (s, 1H), 6.62 (s, 1H), 3.85 (s, 3H), 3.66 (s, 2H), 2.99 (bs, 4H), 2.61-2.59 (bm, 4H), 2.38 (s, 3H).

Example 4h

N-[2-(2,5-Dichloro-pyrimidin-4-ylamino)-4-vinyl-phenyl]-N-methyl-methanesulfonamide N-[2-(2,5-Dichloro-pyrimidin-4-ylamino)-4-vinyl-phenyl]-N-methyl-methanesulfonamide was prepared in a similar manner as 4-Bromo-2-(2,5-dichloro-pyrimidin-4-ylamino)-benzoic acid methyl ester (prepared according to Example 16a) after substituting N-(2-Amino-4-vinyl-phenyl)-N-methyl-methanesulfonamide for 2-Amino-4-bromo-benzoic acid methyl ester. The workup varied in that after concentration of the reaction mixture the residue was partitioned between EtOAc and water. The organic phase was dried over Na$_2$SO$_4$, filtered, and the crude product in the filtrate was adsorbed directly onto silica gel. The crude material was purified via normal phase chromatography (EtOAc/hexane eluent) to give desired N-[2-(2,5-Dichloro-pyrimidin-4-ylamino)-4-vinyl-phenyl]-N-methyl-methanesulfonamide in 50% yield as a yellow solid. LC: 93%; LC/MS: M+H=373.2; $^1$H NMR (DMSO-d6) δ 9.04 (s, 1H, exchangeable), 8.45 (s, 1H), 7.93 (s, 1H), 7.64-7.62 (d, 1H), 7.47-7.45 (d, 1H), 6.82-6.75 (m, 1H), 5.91-5.87 (d, 1H), 5.40-5.37 (d, 1H), 3.17 (s, 3H), 3.04 (s, 3H).

Example 4i

N-(2-{2-[5-Bromo-2-methoxy-4-(4-methyl-piperazin-1-yl)-phenylamino]-5-chloro-pyrimidin-4-ylamino}-4-vinyl-phenyl)-N-methyl-methanesulfonamide N-[2-(2,5-Dichloro-pyrimidin-4-ylamino)-4-vinyl-phenyl]-N-methyl-methanesulfonamide (192 mg, 0.52 mmol), and 5-Bromo-2-methoxy-4-(4-methyl-piperazin-1-yl)-phenylamine (170 mg, 0.57 mmol), along with methanesulfonic acid (43.4 μL, 0.67 mmol) were combined in 2-methoxyethanol (3 mL) and warmed to 105° C. for 4 hours. The resulting solution was concentrated under reduced pressure, dissolved in dimethyl sulfoxide (DMSO) and purified via preparative HPLC. The purest fractions of desired N-(2-{2-[5-Bromo-2-methoxy-4-(4-methyl-piperazin-1-yl)-phenylamino]-5-chloro-pyrimidin-4-ylamino}-4-vinyl-phenyl)-N-methyl-methanesulfonamide were combined and partitioned between EtOAc (2×) and saturated aqueous NaHCO$_3$. The combined organic phases were dried over Na$_2$SO$_4$, filtered, and concentrated under reduced pressure. The 270 mg of yellow residue was triturated with ice cold CH$_3$CN, filtered, and rinsed with a small amount of ice cold CH$_3$CN to yield 110 mg (34%) of desired N-(2-{2-[5-Bromo-2-methoxy-4-(4-methyl-piperazin-1-yl)-phenylamino]-5-chloro-pyrimidin-4-ylamino}-4-vinyl-phenyl)-N-methyl-methanesulfonamide as an off white solid, which was used without further manipulation for its subsequent cyclization to (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene. LC: 98%; LC/MS: M+H=638.01. $^1$H NMR (DMSO-d6) δ 8.41 (s, 1H, exchangeable), 8.23 (s, 1H, exchangeable), 8.21 (s, 1H), 8.18 (s, 1H), 7.82 (s, 1H), 7.58-7.56 (d, 1H, J=8.25 Hz), 7.36-7.34 (d, 1H, J=8.04 Hz), 6.81 (s, 1H), 6.61-6.54 (m, 1H), 5.77-5.72 (d, 1H, J=17.69 Hz), 5.27-5.25 (d, 1H, J=10.77 Hz), 3.79 (s, 3H), 3.18 (s, 3H), 3.10 (s, 3H), 2.98 (s, 4H), 2.5 (s, 4H+DMSO), 2.24 (s, 3H).

Example 4j

(14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene Palladium(II) acetate (Pd(OAc)$_2$) (6.5 mg, 0.03 mmol) was dissolved in CH$_3$CN (3 mL), then tri-o-tolylphosphine (55 mg, 0.18 mmol) was added and the mixture was stirred at room temperature for 15 minutes under argon (Ar). N-(2-{2-[5-Bromo-2-methoxy-4-(4-methyl-piperazin-1-yl)- phenylamino]-5-chloro-pyrimidin-4-ylamino}-4-vinyl-phenyl)-N-methyl-methanesulfonamide (90 mg, 0.14 mmol) and Et₃N (300 μL, 2 mmol) were added to the resulting reaction mixture. The mixture was treated under microwave irradiation at 120° C. for 15 minutes. After cooling the resulting solution was filtered through a Phenomenex Strat-X-C cation catch and release resin, which was then rinsed twice with CH₃CN followed by methanol (MeOH). The resin cartridge was transferred to a new filter flask, and the resin was rinsed twice with 2M ammonia (NH₃) in MeOH. The latter methanol solution was concentrated under reduced pressure to give a yellow residue. This material was treated with CH₃CN (2 mL) to yield a yellow solid, which was filtered and rinsed with a small amount of ice cold CH₃CN to give 57 mg (72%) of desired (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene as a yellow solid, mp 278-280° C. LC: 97%; LC/MS: M+H=556.1; ¹H NMR (DMSO-d6) δ 8.90 (s, 1H), 8.37 (s, 1H), 8.21 (s, 1H), 8.18 (s, 1H; exchangeable), 8.02 (s, 1H; exchangeable), 7.57-7.55 (d, 1H, J=8.25 Hz), 7.15-7.13 (d, 1H, J=8.08 Hz), 6.78-6.75 (d, 1H, J=13.0 Hz), 6.99 (s, 1H), 6.58-6.55 (d, 1H, J=13.1 Hz), 3.85 (s, 3H), 3.21 (s, 3H), 3.08 (s, 3H), 2.92 (bm, 4H), 2.5 (4H+DMSO), 2.25 (s, 3H).

Example 5

6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

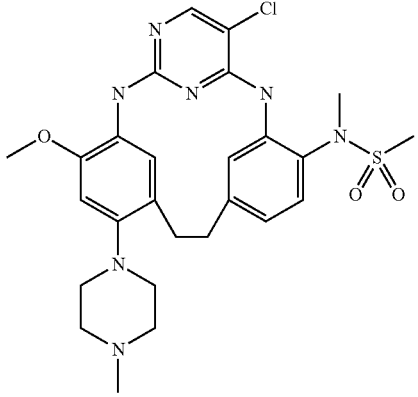

At rt dipotassium azodicarboxylate (640 mg, 3.3 mmol) was added to a solution of (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene (42 mg, 0.076 mmol) in pyridine (7 mL). The resulting mixture was treated with acetic acid (0.53 mL, 9.24 mmol) and immediately warmed to 35° C. After 24 hours the reaction mixture was treated with an additional portion of dipotassium azodicarboxylate (270 mg, 1.4 mmol) and warming continued at 35° C. for two days. The mixture was then combined with water and after fizzing had ceased the aqueous solution was partitioned between saturated aqueous NaHCO₃ and EtOAc. The organic phase was dried over Na₂SO₄, filtered, and concentrated under reduced pressure. The residue was purified via preparative HPLC. The desired product 6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene was isolated in 74% yield as a TFA salt, white lyophylate. LC: 99%; LC/MS: M+H=558.0; ¹H NMR (DMSO-d6) δ 9.83 (bs, 1H, exchangeable), 8.32 (s, 1H, exchangeable), 8.25 (s, 1H, exchangeable), 8.19 (s, 1H), 8.04 (s, 1H), 7.85 (s, 1H), 7.51-7.49 (d, 1H, J=8.21 Hz), 7.11-7.09 (d, 1H, J=8.20 Hz), 6.72 (s, 1H), 3.81 (s, 3H), 3.54-3.51 (d, 2H), 3.28-3.21 (m, 2H), 3.18-3.14 (m, 5H), 3.04-2.92 (m, 8H).

Example 6

6-Chloro-10-(propane-2-sulfonyl)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

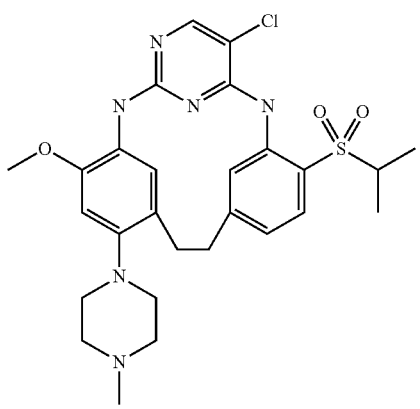 [SMILES: COc1cc(N2CCN(C)CC2)c2cc1Nc1ncc(Cl)c(n1)Nc1cc(ccc1S(=O)(=O)C(C)C)CC2]

Example 6a

4-Bromo-1-isopropylsulfanyl-2-nitro-benzene

2-Propanethiol (0.76 mL, 8 mmol) was added to a rt solution of 4-bromo-1-fluoro-2-nitro-benzene (1.10 g, 5.0 mmol) in ethanol (EtOH) (5 mL) and the resulting solution was warmed at 50° C. for 4 days. After cooling to rt the solution was treated with water (15 mL). The resulting yellow solid was filtered and rinsed liberally with water. After air drying there remained 1.35 g (98%) of desired 4-Bromo-1-isopropylsulfanyl-2-nitro-benzene as a yellow solid. This material was used for the subsequent step without further manipulation. LC: 96%; ¹H NMR (DMSO-d6) δ 8.30-8.29 (d, 1H), 7.90-7.87 (m, 1H), 7.67-7.64 (d, 1H), 3.76-3.73 (m, 1H), 1.30-1.28 (d, 6H).

Example 6b

4-Bromo-2-nitro-1-(propane-2-sulfonyl)-benzene

M-Chloroperbenzoic acid (1.18 g, 6.84 mmol) was added neat to a 0° C. solution of 4-Bromo-1-isopropylsulfanyl-2-nitro-benzene (0.55 g, 2.0 mmol) in methylene chloride (CH₂Cl₂) (15 mL). The reaction was warmed to room temperature (rt) and stirred for 16 hours. The reaction solution was concentrated under reduced pressure and the residual white solid was treated with saturated aqueous NaHCO$_3$ (40 mL). After stirring for 10 minutes, the mixture was filtered and the resulting solid was washed liberally with water. After air drying there remained 0.56 g (91%) of desired 4-Bromo-2-nitro-1-(propane-2-sulfonyl)-benzene as a white solid. This material was used for the subsequent step towards without further manipulation. LC: 95%; $^1$H NMR (DMSO-d6) δ 8.49-8.48 (d, 1H), 8.19-8.16 (m, 1H), 7.97-7.95 (d, 1H), 3.77-3.73 (m, 1H), 1.27-1.26 (d, 6H).

Example 6c

5-Bromo-2(propane-2-sulfonyl)-phenylamine

Iron (710 mg, 13 mmol) was added at rt to a stirring solution of 4-Bromo-2-nitro-1-(propane-2-sulfonyl)-benzene (539 mg, 1.75 mmol) in tetrahydrofuran (THF) (10 mL) and acetic acid (14 mL). The mixture was warmed to 35° C. and stirred 2 hours. The mixture was then cooled to rt, filtered, and the resulting solution was concentrated under reduced pressure. The residue was partitioned between CHCl$_3$ (2×) and saturated aqueous NaHCO$_3$. The combined organic phases were dried over Na$_2$SO$_4$, filtered, and concentrated under reduced pressure to yield 334 mg (69%) of 5-Bromo-2(propane-2-sulfonyl)-phenylamine as a clear oil, which crystallized to a white solid upon sitting. This material was used for its subsequent step without further manipulation. LC: 97%; LC/MS: M+H=279.8.

Example 6d

2-Nitro-1-(propane-2-sulfonyl)-4-vinyl-benzene

2-Nitro-1-(propane-2-sulfonyl)-4-vinyl-benzene was prepared in a similar manner as 2-Methoxy-5-vinyl-phenylamine (prepared according to Example 13b) after substituting 4-Bromo-2-nitro-1-(propane-2-sulfonyl)-benzene for 5-bromo-2-methoxy-phenylamine. The workup varied in that after concentration of the reaction mixture, the residue was partitioned between EtOAc (2×) and water. The combined organic phases were dried over MgSO$_4$, filtered, and the filtrate was adsorbed directly onto silica gel under reduced pressure. The residue was purified via normal phase chromatography (EtOAc/Hexane eluent) to give desired 2-Nitro-1-(propane-2-sulfonyl)-4-vinyl-benzene in 55% yield. LC: 99%; $^1$H NMR (DMSO-d6) δ 8.26 (s, 1H), 8.02-7.98 (m, 2H), 6.95-6.87 (m, 1H), 6.27-6.23 (d, 1H), 5.67-5.64 (d, 1H), 3.78-3.70 (m, 1H), 1.28-1.26 (d, 6H).

Example 6e 2-(Propane-2-sulfonyl)-5-vinyl-phenylamine

Iron (391 mg, 7 mmol) was added at rt to a stirring solution of 2-Nitro-1-(propane-2-sulfonyl)-4-vinyl-benzene (255 mg, 1 mmol) in THF (5 mL) and acetic acid (10 mL). The mixture was warmed to 35° C. and stirred 16 hours. The mixture was then cooled to rt, filtered, and the resulting solution was concentrated under reduced pressure. The residue was partitioned between EtOAc (2×) and saturated aqueous NaHCO$_3$. The combined organic phases were dried over Na$_2$SO$_4$, filtered, and concentrated under reduced pressure to yield 225 mg (99%) of 2-(Propane-2-sulfonyl)-5-vinyl-phenylamine as a clear oil. This material was used for subsequent steps without further manipulation. LC/MS: M+H=226.0; $^1$H NMR (CDCl$_3$-d3) δ 7.62-7.60 (d, 1H), 6.89-6.87 (d, 1H), 6.72 (s, 1H), 6.68-6.61 (m, 1H), 5.86-5.82 (d, 1H), 5.42-5.39 (d, 1H), 5.08 (bs, 2H), 3.37-3.30 (m, 1H), 1.34-1.32 (d, 6H).

Example 6f (2,5-Dichloro-pyrimidin-4-yl)-[2-(propane-2-sulfonyl)-5-vinyl-phenyl]-amine 2-(Propane-2-sulfonyl)-5-vinyl-phenylamine (989 mg, 4.4 mmol), 2,4,5-trichloro-pyrimidine (7.02 mL, 61.2 mmol) and ethyldiisopropylamine (EtN(i-Pr)$_2$) (1.2 mL, 7.2 mmol) were warmed to 115° C. for 16 hours. The reaction mixture was concentrated under reduced pressure and the residue was partitioned between CHCl$_3$ (2×) and water. The organic phase was dried over Na$_2$SO$_4$, filtered, and the crude product in the filtrate was adsorbed directly onto silica gel. The crude material was purified via normal phase chromatography (EtOAc/hexane eluent) to give desired (2,5-Dichloro-pyrimidin-4-yl)-[2-(propane-2-sulfonyl)-5-vinyl-phenyl]-amine in 51% yield as a yellow solid. LC: 100%; LC/MS: M+H=372.1; $^1$H NMR (DMSO-d6) δ 9.79 (s, 1H), 8.55-8.32 (d, 1H), 7.85-7.83 (bs, 1H), 6.89-6.82 (m, 1H), 6.07-6.03 (d, 1H), 5.57-5.54 (d, 1H), 3.52 (bm, 1H), 1.17-1.15 (d, 6H).

Example 6g

N(2)-[5-Bromo-2-methoxy-4-(4-methyl-piperazin-1-yl)-phenyl]-5-chloro-N(4)-[2-(propane-2-sulfonyl)-5-vinyl-phenyl]-pyrimidine-2,4-diamine (2,5-Dichloro-pyrimidin-4-yl)-[2-(propane-2-sulfonyl)-5-vinyl-phenyl]-amine (200 mg, 0.54 mmol), and 5-Bromo-2-methoxy-4-(4-methyl-piperazin-1-yl)-phenylamine (177 mg, 0.59 mmol), along with methanesulfonic acid (45.3 µL, 0.70 mmol) were combined in 2-methoxy-ethanol (3 mL) and warmed to 105° C. for 3 hours. The resulting solution was concentrated under reduced pressure, dissolved in DMSO and purified via preparative HPLC. The purest fractions of desired N(2)-[5-Bromo-2-methoxy-4-(4-methyl-piperazin-1-yl)-phenyl]-5-chloro-N(4)-[2-(propane-2-sulfonyl)-5-vinyl-phenyl]-pyrimidine-2,4-diamine were combined and partitioned between EtOAc (2×) and saturated aqueous NaHCO$_3$. The combined organic phases were dried over Na$_2$SO$_4$, filtered, and concentrated under reduced pressure. The 215 mg of yellow residue was triturated with ice cold CH$_3$CN, filtered, and rinsed with a small amount of ice cold CH$_3$CN to yield 70 mg (20%) of desired N(2)-[5-Bromo-2-methoxy-4-(4-methyl-piperazin-1-yl)-phenyl]-5-chloro-N(4)-[2-(propane-2-sulfonyl)-5-vinyl-phenyl]-pyrimidine-2,4-diamine as an off white solid, which was used without further manipulation for its subsequent cyclization to (14Z)-6-Chloro-10-(propane-2-sulfonyl)-17-(4-methyl-piperazin-1-yl)-19-methoxy-2,4,8,22-tetraazatetracyclo [14.3.1.1$^{3,7}$.1$^{9,13}$]docosa-1(20),3(22),4,6,9(21),10,12,14,16,18-decaene. LC: 99%; LC/MS: M+H=637.1; $^1$H NMR (DMSO-d6) δ 9.48 (s, 1H, exchangeable), 8.53 (s, 1H), 8.46 (s, 1H, exchangeable), 8.32 (s, 1H), 7.78-7.76 (m, 2H), 7.49-7.47 (d, 1H, J=7.64 Hz), 6.80 (s, 1H), 6.67-6.57 (m, 1H), 5.87-5.83 (d, 1H, J=17.72 Hz), 5.40-5.37 (d, 1H, J=10.85 Hz), 3.78 (s, 3H), 3.46-3.41 (m, 1H), 2.97 (s, 4H), 2.5 (s, 4H+DMSO), 2.24 (s, 3H), 1.18-1.16 (d, 6H, J=6.68 Hz).

Example 6h (14Z)-6-Chloro-10-(propane-2-sulfonyl)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene Pd(OAc)$_2$ (6.5 mg, 0.03 mmol) was dissolved in CH$_3$CN (3 mL), then tri-o-tolylphosphine (55 mg, 0.18 mmol) was added and the mixture was stirred at rt for 15 minutes under Ar. N(2)-[5-Bromo-2-methoxy-4-(4-methyl-piperazin-1-yl)-phenyl]-5-chloro-N(4)-[2-(propane-2-sulfonyl)-5-vinyl-phenyl]-pyrimidine-2,4-diamine (60 mg, 0.094 mmol) and Et$_3$N (92 µL, 0.66 mmol) were added to the resulting reaction mixture. The mixture was treated under microwave irradiation at 120° C. for 15 minutes. After cooling the resulting solution was filtered through a Phenomenex Strat-X-C cation catch and release resin, which was then rinsed twice with CH$_3$CN followed by MeOH. The resin cartridge was transferred to a new filter flask, and the resin was rinsed twice with 2M NH$_3$ in MeOH. The latter methanol solution was concentrated under reduced pressure to give a yellow residue. This material was treated with CH$_3$CN (2 mL) to yield a yellow solid, which was filtered and rinsed with a small amount of ice cold CH$_3$CN to give 33 mg (63%) of desired (14Z)-6-Chloro-10-(propane-2-sulfonyl)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene as a yellow solid. LC: 97%; LC/MS: M+H=555.1; $^1$H NMR (DMSO-d6) δ 9.49 (s, 1H, exchangeable), 9.27 (s, 1H), 8.42 (s, 1H), 8.25 (s, 1H), 8.16 (s, 1H, exchangeable), 7.74-7.72 (d, 1H, J=8.21 Hz), 7.28-7.26 (d, 1H, 8.00 Hz), 6.92-6.89 (d, 1H, J=13.08 Hz), 6.72 (s, 1H), 6.62-6.58 (d, 1H, J=13.20 Hz), 3.87 (s, 3H), 3.40-3.37 (m, 1H), 2.92 (s, 4H), 2.54 (s, 4H), 2.25 (s, 3H), 1.17-1.15 (d, 6H, J=6.76 Hz).

Example 6i

6-Chloro-10-(propane-2-sulfonyl)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

6-Chloro-10-(propane-2-sulfonyl)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene (prepared according to Example 5) after substituting (14Z)-6-Chloro-10-(propane-2-sulfonyl)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene. The desired product 6-Chloro-10-(propane-2-sulfonyl)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene was isolated in 53% yield as a TFA salt white lyophylate. LC: 99%; LC/MS: M+H=557.10; $^1$H NMR (DMSO-d6) δ 9.71 (bs, 1H, exchangeable), 9.30 (s, 1H, exchangeable), 8.38 (bs, 2H, 1 exchangeable), 7.86 (s, 1H), 7.70-7.68 (d, 1H, J=8.17 Hz), 7.22-7.20 (d, 1H, J=8.16 Hz), 6.73 (s, 1H), 3.81 (s, 3H), 3.54-3.51 (d, 2H), 3.40-3.33 (m, 1H), 3.29-3.21 (m, 2H), 3.19-3.15 (d, 2H), 3.05-2.91 (m, 9H), 1.13-1.11 (d, 6H, J=6.77 Hz).

Example 7

(14Z)-6-Chloro-10-(2-methanesulfonyl-methyl-amino)-17-(1-methyl-piperidin-4-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene

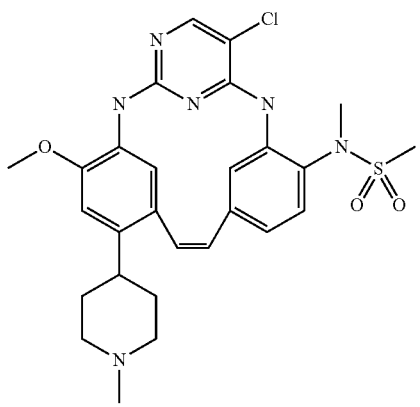

Example 7a 4-(2-Bromo-5-methoxy-phenyl)-piperidine 4-(2-Bromo-5-methoxy-phenyl)-piperidine-1-carboxylic acid tert-butyl ester (1.85 g, 5 mmol) in CH$_2$Cl$_2$ (6 mL) was treated with trifluoroacetic acid (TFA) (2.5 mL, 32 mmol) at 0° C. After 1 hour the mixture was warmed to rt and stirred an additional 4 hours. The mixture was then concentrated under reduced pressure and the resulting residue partitioned between CHCl$_3$ (2×) and saturated aqueous NaHCO$_3$. The combined organic phases were dried over Na$_2$SO$_4$, filtered, and concentrated under reduced pressure to yield desired 4-(2-Bromo-5-methoxy-phenyl)-piperidine in 100% yield as a tan oil, which was used for the subsequent reaction without further manipulation. LC: 95%.

Example 7b 4-(2-Bromo-5-methoxy-phenyl)-1-methyl-piperidine

A rt solution of 4-(2-Bromo-5-methoxy-phenyl)-piperidine (220 mg, 0.80 mmol) in methanol (2 mL) and CH$_2$Cl$_2$ (3 mL) was treated with 40% formaldehyde in water (0.13 mL, 1.6 mmol), then acetic acid (54.6 uL, 0.96 mmol), followed by sodium triacetoxyborohydride (305 mg, 1.44 mmol). After 5 hours the mixture was treated with saturated aqueous NaHCO$_3$. After fizzing ceased, the reaction was diluted with additional CH$_2$Cl$_2$ and the layers separated. The organic phase was dried over Na$_2$SO$_4$, filtered, and concentrated under reduced pressure to give desired 4-(2-Bromo-5-methoxy-phenyl)-1-methyl-piperidine as a clear oil in 98% yield. LC: 95%; LC/MS: M+H=286.0.

Example 7c 4-(2-Bromo-5-methoxy-phenyl)-1-methyl-piperidine nitrate

A solution of (2-Bromo-5-methoxy-phenyl)-1-methyl-piperidine (970 mg, 3.4 mmol) in ether (Et$_2$O) (2 mL) was added to a premixed solution of fuming nitric acid (HNO$_3$) (169 μL) in EtOH (2 mL). The resulting solution was cooled in an ice bath. After a short time solid precipitated, which was filtered and rinsed with Et$_2$O yielding 4-(2-Bromo-5-methoxy-phenyl)-1-methyl-piperidine nitrate as a white solid in 81% yield, mp 135-137° C. LC: 96%; LC/MS: M+H=286.0, $^1$H NMR (DMSO-d6) δ 9.24 (bs, 1H), 7.55-7.53 (d, 1H), 6.85-6.83 (d, 1H), 5.78 (s, 1H), 3.77 (s, 3H), 3.53-3.50 (d, 2H), 3.18-3.07 (m, 3H), 2.82 (s, 3H), 2.00-1.97 (d, 2H), 1.85-1.76 (m, 2H).

Example 7d 4-(2-Bromo-5-methoxy-4-nitro-phenyl)-1-methyl-piperidine

A solution of 4-(2-Bromo-5-methoxy-phenyl)-1-methyl-piperidine nitrate (710 mg, mmol) in water (2 mL) was added over 15 seconds to a 0° C. concentrated sulfuric acid (5 mL). After 10 minutes the reaction mixture was diluted with ice (25 g), then while keeping cool basified with 45% potassium hydroxide (KOH). The salts which precipitated were filtered off and rinsed liberally with EtOAc. The biphasic filtrate layers were separated, and the organic phase was dried over Na$_2$SO$_4$, filtered, and concentrated under reduced pressure to yield 670 mg of crude material. This material was purified via preparative HPLC and the purest fractions of desired product were combined and partitioned between EtOAc and saturated aqueous NaHCO$_3$. The organic phase was dried over Na$_2$SO$_4$, filtered, and concentrated under reduced pressure to yield 320 mg (48%) of desired 4-(2-Bromo-5-methoxy-4-nitro-phenyl)-1-methyl-piperidine as a clear oil. LC: 93%; LC/MS: 329.1; $^1$H NMR (CDCl$_3$-d3) δ 8.08 (s, 1H), 7.00 (s, 1H), 3.93 (s, 3H), 3.03-2.97 (m, 3H), 2.36 (s, 3H), 2.16-2.11 (m, 2H), 1.91-1.88 (d, 2H), 1.79-1.70 (m, 2H).

Example 7e

5-Bromo-2-methoxy-4-(1-methyl-piperidin-4-yl)-phenylamine

Iron (78 mg, 1.4 mmol) was added to a solution of 4-(2-Bromo-5-methoxy-4-nitro-phenyl)-1-methyl-piperidine (52 mg, 0.16 mmol) in THF (1 mL) and acetic acid (AcOH) (1 mL), and the resulting mixture was warmed to 35° C. for 5 hours, then at rt for 2 days. The resulting solids were filtered off, rinsed with THF, and the filtrate was concentrated under reduced pressure. The residue was partitioned between EtOAc (2×) and saturated aqueous NaHCO$_3$. The combined organic phases were dried over Na$_2$SO$_4$, filtered, and concentrated under reduced pressure to yield 25 mg (53%) of desired 5-Bromo-2-methoxy-4-(1-methyl-piperidin-4-yl)-phenylamine as a yellow oil. LC/MS: M+H=299.0; $^1$H NMR (CDCl$_3$-d3) δ 6.86 (s, 1H), 6.69 (s, 1H), 3.80 (s, 3H), 3.73 (bs, 2H), 2.98-2.95 (d, 2H), 2.89-2.83 (m, 1H), 2.33 (s, 3H), 2.12-2.06 (m, 2H), 1.84-1.81 (d, 2H), 1.75-1.66 (m, 2H).

Example 7f

N-(2-{2-[5-Bromo-2-methoxy-4-(1-methyl-piperidin-4-yl)-phenylamino]-5-chloro-pyrimidin-4-ylamino}-4-vinyl-phenyl)-N-methyl-methanesulfonamide N-(2-{2-[5-Bromo-2-methoxy-4-(1-methyl-piperidin-4-yl)-phenylamino]-5-chloro-pyrimidin-4-ylamino}-4-vinyl-phenyl)-N-methyl-methanesulfonamide was prepared in a similar manner as N-(2-{2-[5-Bromo-2-methoxy-4-(4-methyl-piperazin-1-yl)-phenylamino]-5-chloro-pyrimidin-4-ylamino}-4-vinyl-phenyl)-N-methyl-methanesulfonamide (prepared according to Example 4i) after substituting 5-Bromo-2-methoxy-4-(1-methyl-piperidin-4-yl)-phenylamine for 5-Bromo-2-methoxy-4-(4-methyl-piperazin-1-yl)-phenylamine yielding N-(2-{2-[5-Bromo-2-methoxy-4-(1-methyl-piperidin-4-yl)-phenylamino]-5-chloro-pyrimidin-4-ylamino}-4-vinyl-phenyl)-N-methyl-methanesulfonamide as a white solid in 52%, mp 196-198° C. LC: 98%; LC/MS: M+H=637.0.

Example 7g (14Z)-6-Chloro-10-(2-methanesulfonyl-methyl-amino)-17-(1-methyl-piperidin-4-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene (14Z)-6-Chloro-10-(2-methanesulfonyl-methyl-amino)-17-(1-methyl-piperidin-4-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene was prepared in a similar manner as (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene (prepared according to Example 4j) after substituting N-(2-{2-[5-Bromo-2-methoxy-4-(1-methyl-piperidin-4-yl)-phenylamino]-5-chloro-pyrimidin-4-ylamino}-4-vinyl-phenyl)-N-methyl-methanesulfonamide for N-(2-{2-[5-Bromo-2-methoxy-4-(4-methyl-piperazin-1-yl)-phenylamino]-5-chloro-pyrimidin-4-ylamino}-4-vinyl-phenyl)-N-methyl-methanesulfonamide yielding (14Z)-6-Chloro-10-(2-methanesulfonyl-methyl-amino)-17-(1-methyl-piperidin-4-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene as a light tan solid in 62%, mp 244-246° C. LC: 95%; LC/MS: M+H=555.1; $^1$H NMR (DMSO-d6) δ 8.7 (s, 1H), 8.23 (s, 1H, exchangeable), 8.18 (s, 1H, exchangeable), 8.16 (s, 1H), 7.98 (s, 1H), 7.52-7.50 (d, 1H, J=7.18 Hz), 7.09-7.07

(d, 1H, J=8.52 Hz), 6.91-6.88 (d, 1H, J=13.16 Hz), 6.83 (s, 1H), 6.73-6.70 (d, 1H, J=12.24 Hz), 3.81 (s, 3H), 3.18 (s, 3H), 3.06 (s, 3H), 2.88-2.85 (d, 2H), 2.73 (m, 1H), 2.20 (s, 3H), 2.01-1.95 (m, 2H), 1.71-1.63 (m, 4H).

Example 8

6-Chloro-10-(2-methanesulfonyl-methyl-amino)-17-(1-methyl-piperidin-4-yl)-19-methoxy-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

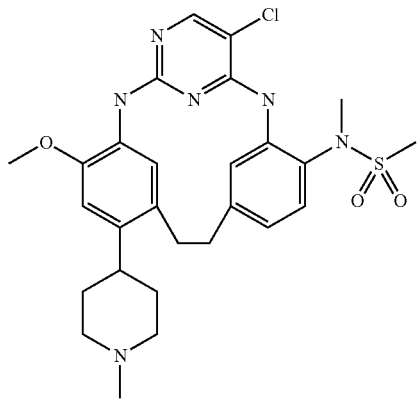

6-Chloro-10-(2-methanesulfonyl-methyl-amino)-17-(1-methyl-piperidin-4-yl)-19-methoxy-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene (prepared according to Example 5) after substituting (14Z)-6-Chloro-10-(2-methanesulfonyl-methyl-amino)-17-(1-methyl-piperidin-4-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene yielding 6-Chloro-10-(2-methanesulfonyl-methyl-amino)-17-(1-methyl-piperidin-4-yl)-19-methoxy-2,4,8,22-tetraazatetracyclo[14.3.1.1$^{3,7}$.1$^{9,13}$]docosa-1(20),3(22),4,6,9(21),10,12,16,18-nonaene as a TFA salt lyophylate in 60% yield. LC: 99%; LC/MS: M+H=557.1; $^1$H NMR (DMSO-d6) δ 9.31 (bs, 1H, exchangeable), 8.26 (s, 1H, exchangeable), 8.22 (s, 1H, exchangeable), 8.17 (s, 1H), 8.12 (s, 1H), 7.71 (s, 1H), 7.48-7.46 (d, 1H, J=8.44 Hz), 7.09-7.07 (d, 1H, J=8.16 Hz), 6.69 (s, 1H), 3.84 (s, 3H), 3.7-3.5 (bm, 2H+H$_2$O), 3.17 (s, 3H), 3.09-2.94 (bm, 10H), 2.84 (s, 3H), 1.91 (bm, 4H).

Example 9

(14Z)-6-Chloro-10-(2-methanesulfonyl-methyl-amino)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene Trifluoroacetate (1:1)

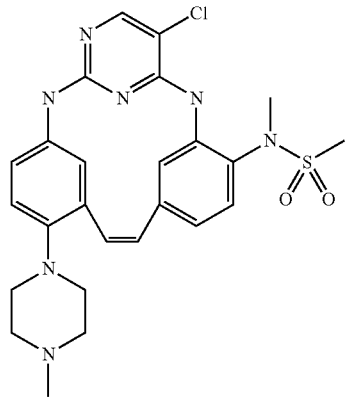 [SMILES: CN1CCN(c2ccc3cc2CCc2ccc(N(C)S(C)(=O)=O)c(c2)Nc2nc(ncc2Cl)N3)CC1]

Example 9a

N-(2-Amino-4-bromo-phenyl)-N-methyl-methanesulfonamide

Iron (810 mg, 14 mmol) was added to a solution of N-(4-Bromo-2-nitro-phenyl)-N-methyl-methanesulfonamide (618 mg, 2.0 mmol) in THF (10 mL) and AcOH (16 mL), and the resulting mixture was warmed to 35° C. for 5 hours. The resulting solids were filtered off, rinsed with THF, and the filtrate was concentrated under reduced pressure. The residue was partitioned between EtOAc (2×) and saturated aqueous NaHCO$_3$. The combined organic phases were dried over Na$_2$SO$_4$, filtered, and concentrated under reduced pressure to yield 550 mg (98%) of desired N-(2-Amino-4-bromo-phenyl)-N-methyl-methanesulfonamide as a clear oil, and used directly for subsequent steps without further manipulation. LC: 93%; $^1$H NMR (DMSO-d6) δ 7.14-7.12 (d, 1H), 6.92 (s, 1H), 6.69-6.67 (d, 1H), 5.43 (s, 2H), 3.05 (s, 6H).

Example 9b

N-[4-Bromo-2-(2,5-dichloro-pyrimidin-4-ylamino)-phenyl]-N-methyl-methanesulfonamide (5g)

N-(2-Amino-4-bromo-phenyl)-N-methyl-methanesulfonamide (550 mg, 2.0 mmol) and 2,4,5-trichloropyrimidine (678 μL, 5.9 mmol) were combined with EtN(i-Pr)$_2$ (940 μL, 5.4 mmol) in N-Methylpyrrolidinone (5 mL) and warmed to 100° C. for 2 days. The resulting mixture was concentrated under high vacuum and the residue treated with 1:1 H$_2$O:CH$_3$CN (8 mL). The resulting solid was filtered and rinsed with ice cold 1:1 H$_2$O:CH$_3$CN (2 mL), then with MeOH, yielding 587 mg (70%) of desired N-[4-Bromo-2-(2,5-dichloro-pyrimidin-4-ylamino)-phenyl]-N-methyl-methanesulfonamide as a tannish solid, which was used for subsequent steps without further manipulation. LC: 95%; LC/MS: M+H=426.9.

Example 9c

1-(2-Bromo-4-nitro-phenyl)-4-methyl-piperazine 1-(2-Bromo-4-nitro-phenyl)-4-methyl-piperazine was prepared in a similar manner as 1-[3-(2-bromo-4-nitrophenoxy)-propyl]-pyrrolidine (prepared according to Example 22a) after substituting 1-methyl-piperazine for N-β-hydroxyethylpyrrolidine. In addition, no $K_2CO_3$ was used, and the reaction was run at 90° C. rather than 100° C. The desired product 1-(2-Bromo-4-nitro-phenyl)-4-methyl-piperazine was isolated in 97% as a yellow solid. LC: 98%; $^1$HNMR (DMSO-d6) δ 8.38-8.37 (d, 1H), 8.21-8.18 (m, 1H), 7.29-7.27 (d, 1H), 3.18-3.16 (bm, 4H), 2.50 (s, 4H+DMSO), 2.25 (s, 3H).

Example 9d

1-Methyl-4-(4-nitro-2-vinyl-phenyl)-piperazine

To a room temperature mixture of 1-(2-Bromo-4-nitrophenyl)-4-methyl-piperazine (300 mg, 1.0 mmol), $K_2CO_3$ (663 mg, 4.8 mmol), and tetrakis(triphenylphosphine)palladium(0) (Pd(PPh$_3$)$_4$) (200 mg, 0.2 mmol) in 1,2-dimethoxy-ethane (6 mL) and water (1 mL) was added vinylboronic acid dibutyl ester (0.52 mL, 2.4 mmol). The mixture was then warmed to 90° C. for 5 h. The resulting mixture was concentrated under reduced pressure, and the residue was partitioned between aqueous 1N HCl and EtOAc. The aqueous phase was basified with 8N KOH while cooling. The resulting solid was filtered off, rinsed with ice cold water, and air dried yielding 1-Methyl-4-(4-nitro-2-vinyl-phenyl)-piperazine in 70% yield as a yellow solid. LC: 98%; LC/MS M+H=248.1, $^1$H NMR (DMSO-d6) δ 8.24-8.23 (d, 1H), 8.12-8.09 (m, 1H), 7.18-7.16 (d, 1H), 6.82-6.75 (m, 1H), 5.97-5.93 (d, 1H), 5.46-5.43 (d, 1H), 3.08-3.06 (m, 4H), 2.50 (s, 4H+DMSO), 2.25 (s, 3H).

Example 9e

4-(4-Methyl-piperazin-1-yl)-3-vinyl-phenylamine

Iron (2.93 g, 52 mmol) was added at rt to a stirring solution of 1-Methyl-4-(4-nitro-2-vinyl-phenyl)-piperazine (1.95 g, 7.9 mmol) in THF (30 mL) and acetic acid (60 mL). The mixture was warmed to 35° C. and stirred 16 hours. The mixture was then cooled to rt, filtered, and the resulting solution was concentrated under reduced pressure. The residue was partitioned between CHCl$_3$ (2×) and saturated aqueous NaHCO$_3$. The combined organic phases were dried over Na$_2$SO$_4$, filtered, and concentrated under reduced pressure to yield 1.71 g (100%) of 4-(4-Methyl-piperazin-1-yl)-3-vinyl-phenylamine as a yellow tinted oil, which crystallized upon sitting. This material was used for its subsequent step without further manipulation. LC/MS: M+H=218.1.

Example 9f

N-(4-Bromo-2-{5-chloro-2-[4-(4-methyl-piperazin-1-yl)-3-vinyl-phenylamino]-pyrimidin-4-ylamino}-phenyl)-N-methyl-methanesulfonamide N-[4-Bromo-2-(2,5-dichloro-pyrimidin-4-ylamino)-phenyl]-N-methyl-methanesulfonamide (213 mg, 0.50 mmol), and 4-(4-Methyl-piperazin-1-yl)-3-vinyl-phenylamine (109 mg, 0.50 mmol), along with methanesulfonic acid (46 μL, 0.71 mmol) were combined in 2-methoxy-ethanol (6 mL) and warmed to 110° C. for 4 hours. The resulting solution was concentrated under reduced pressure and the residue partitioned between EtOAc (2×) and saturated aqueous NaHCO$_3$. The combined organic phases were dried over Na$_2$SO$_4$, filtered, and concentrated under reduced pressure. The remaining brown oil was dissolved in CH$_3$CN (3 mL). The solid which crystallized was filtered and rinsed with a small amount of ice cold CH$_3$CN to yield 118 mg (39%) of desired N-(4-Bromo-2-{5-chloro-2-[4-(4-methyl-piperazin-1-yl)-3-vinyl-phenylamino]-pyrimidin-4-ylamino}-phenyl)-N-methyl-methanesulfonamide as an off white solid, which was used without further manipulation for its subsequent cyclization in the next step. LC: 90%; LC/MS: M+H=608.1.

Example 9g

(14Z)-6-Chloro-10-(2-methanesulfonyl-methyl-amino)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene Trifluoroacetate (1:1)

Pd(OAc)$_2$ (24 mg, 0.10 mmol), tri-o-tolylphosphine (140 mg, 0.45 mmol), and N-(4-Bromo-2-{5-chloro-2-[4-(4-methyl-piperazin-1-yl)-3-vinyl-phenylamino]-pyrimidin-4-ylamino}-phenyl)-N-methyl-methanesulfonamide (80 mg, 0.13 mmol) were combined with CH$_3$CN (2 mL) and triethylamine (Et$_3$N) (120 μL, 0.9 mmol). The mixture was treated under microwave irradiation at 120° C. for 45 minutes. By LC analysis, the reaction had not proceeded to completion, so the reaction mixture was filtered and the solution recharged with second portions of Pd(OAc)$_2$ (35 mg, 0.16 mmol), tri-o-tolylphosphine (170 mg, 0.56 mmol), and Et$_3$N (160 μL, 1.1 mmol). The mixture was again treated under microwave irradiation at 120° C. for 120 minutes. After cooling, the resulting mixture was filtered and the filtrate was concentrated under reduced pressure. The concentrated residue was partitioned between 1N HCl (1.4 mL) and EtOAc (2×). The aqueous phase was purified directly via preparative HPLC and the purest fractions combined and lyophilized to yield desired (14Z)-6-Chloro-10-(2-methanesulfonyl-methyl-amino)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene as its TFA salt in 37% yield. This material was carried on for subsequent conversion without further manipulation. LC: 100%; LC/MS: M+H=526.1; $^1$H NMR (DMSO-d6) δ 9.80 (bs, 1H), 9.42 (s, 1H), 8.89 (s, 1H), 8.42 (s, 1H), 8.23 (s, 1H), 8.20 (s, 1H), 7.58-7.56 (d, 1H), 7.20-7.18 (d, 1H), 7.07-7.01 (m, 2H), 6.88-6.84 (d, 1H), 6.74-6.71 (d, 1H), 3.53-3.51 (d, 2H), 3.35-3.21 (m, 7H), 3.09 (s, 3H), 2.97-2.91 (m, 2H), 2.89 (s, 3H).

Example 10

6-Chloro-10-(2-methanesulfonyl-methyl-amino)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

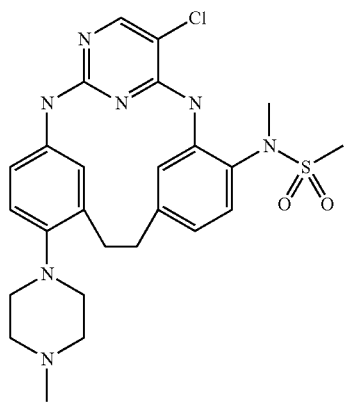

6-Chloro-10-(2-methanesulfonyl-methyl-amino)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene (prepared according to Example 5) after substituting (14Z)-6-Chloro-10-(2-methanesulfonyl-methyl-amino)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene. The desired product 6-Chloro-10-(2-methanesulfonyl-methyl-amino)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene was isolated in 72% yield as a white lyophylate. LC: 100% pure; LC/MS: M+H=528.1; $^1$H NMR (DMSO-d6) δ 9.58 (bs, 1H), 9.38 (s, 1H), 8.21 (s, 1H), 8.18 (s, 1H), 8.10 (s, 1H), 8.02 (s, 1H), 7.53-7.51 (d, 1H, J=8.09 Hz), 7.14-7.12 (d, 1H, J=8.12 Hz), 7.06-7.04 (d, 1H, J=8.43 Hz), 6.96-6.94 (d, 1H, J=8.48 Hz), 3.53-3.50 (d, 2H), 3.25-3.22 (m, 2H), 3.19 (s, 3H), 3.11-2.91 (m, 14H).

Example 11

(14Z)-6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene Trifluoroacetate (1:1)

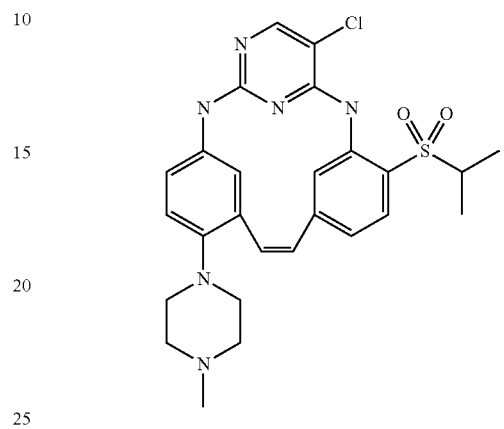

Example 11a

5-Bromo-2(propane-2-sulfonyl)-phenylamine

Iron (710 mg, 13 mmol) was added at rt to a stirring solution of 4-Bromo-2-nitro-1-(propane-2-sulfonyl)-benzene (539 mg, 1.75 mmol) in THF (10 mL) and acetic acid (14 mL). The mixture was warmed to 35° C. and stirred 2 hours. The mixture was then cooled to rt, filtered, and the resulting solution was concentrated under reduced pressure. The residue was partitioned between CHCl$_3$ (2×) and saturated aqueous NaHCO$_3$. The combined organic phases were dried over Na$_2$SO$_4$, filtered, and concentrated under reduced pressure to yield 334 mg (69%) of 5-Bromo-2(propane-2-sulfonyl)-phenylamine as a clear oil, which crystallized to a white solid upon sitting. This material was used for its subsequent step without further manipulation. LC: 97%; LC/MS: M+H=279.8.

Example 11b

[5-Bromo-2-(propane-2-sulfonyl)-phenyl]-(2,5-dichloro-pyrimidin-4-yl)-amine

A mixture of 5-Bromo-2(propane-2-sulfonyl)-phenylamine (310 mg, 1.11 mmol) and 2,4,5-trichloropyrimidine (153 μL, 1.34 mmol) in DMF (2 mL) at 0° C. was treated with neat sodium hydride (NaH) (89 mg, 2.2 mmol; 60% oil dispersion) over 30 seconds. After an hour at 0° C., additional 2,4,5-trichloropyrimidine (150 μL, 1.30 mmol) was added followed by neat NaH (160 mg, 4 mmol; 60% oil dispersion). After another hour the mixture was treated with saturated aqueous NH$_4$Cl, then diluted with water. The resulting brownish solid was filtered and washed liberally with water. The solid was then rinsed with ice cold CH$_3$CN (3 mL). The resulting 415 mg (88%) of tannish solid [5-Bromo-2-(propane-2-sulfonyl)-phenyl]-(2,5-dichloro-pyrimidin-4-yl)-amine was used for subsequent steps without further manipulation. LC: 100%; LC/MS: M+H=425.9.

Example 11c

N(4)-[5-Bromo-2-(propane-2-sulfonyl)-phenyl]-5-chloro-N(2)-[4-(4-methyl-piperazin-1-yl)-3-vinyl-phenyl]-pyrimidine-2,4-diamine

[5-Bromo-2-(propane-2-sulfonyl)-phenyl]-(2,5-dichloro-pyrimidin-4-yl)-amine (150 mg, 0.35 mmol), and 4-(4-Methyl-piperazin-1-yl)-3-vinyl-phenylamine (77 mg, 0.35 mmol), along with methanesulfonic acid (33 µL, 0.50 mmol) were combined in 2-methoxy-ethanol (4 mL) and warmed to 110° C. for 3 hours. The resulting solution was concentrated under reduced pressure and the residue partitioned between $CHCl_3$ (2×) and saturated aqueous $NaHCO_3$. The combined organic phases were dried over $Na_2SO_4$, filtered, and concentrated under reduced pressure. The 270 mg of remaining brown oil was dissolved in $CH_3CN$ (3 mL). The solid which crystallized was filtered and rinsed with a small amount of ice cold $CH_3CN$ to yield 90 mg (40%) of desired N(4)-[5-Bromo-2-(propane-2-sulfonyl)-phenyl]-5-chloro-N(2)-[4-(4-methyl-piperazin-1-yl)-3-vinyl-phenyl]-pyrimidine-2,4-diamine as a light brown solid, which was used without further manipulation for its subsequent cyclization to (14Z)-6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene. LC: 92%; LC/MS: M+H=607.0.

Example 11d (14Z)-6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene Trifluoroacetate (1:1)

$Pd(OAc)_2$ (48 mg, 0.21 mmol), tri-o-tolylphosphine (275 mg, 0.90 mmol), and N(4)-[5-Bromo-2-(propane-2-sulfonyl)-phenyl]-5-chloro-N(2)-[4-(4-methyl-piperazin-1-yl)-3-vinyl-phenyl]-pyrimidine-2,4-diamine (160 mg, 0.26 mmol) were combined with $CH_3CN$ (4 mL) and $Et_3N$ (250 µL, 1.8 mmol). The mixture was treated under microwave irradiation at 120° C. for 120 minutes. After cooling, the resulting mixture was filtered and the filtrate was concentrated under reduced pressure. The concentrated residue was partitioned between 1N HCl and EtOAc (2×). The aqueous phase was cooled and neutralized with KOH solution until approximately pH 7, and then diluted with saturated aqueous $NaHCO_3$. The resulting basic solution was extracted with $CHCl_3$ (2×). The combined $CHCl_3$ extracts were dried over $Na_2SO_4$, filtered, and concentrated under reduced pressure. The residue was purified via preparative HPLC and the purest fractions combined and lyophilized to yield desired (14Z)-6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene as its TFA salt in 32% yield. This material was carried on for subsequent conversion to 6-Chloro-10-(propane-2-sulfonyl)-17-(4-methyl-piperazin-1-yl)-2,4,8,22-tetraazatetracyclo[14.3.1.1$^{3,7}$.1$^{9,13}$]docosa-1(20),3(22),4,6,9(21),10,12,16,18-nonaene without further manipulation. LC: 100%; LC/MS: M+H=525.1; $^1$H NMR (DMSO-d6) δ 9.65 (bs, 1H), 9.55 (s, 1H), 9.48 (s, 1H), 9.26-9.25 (d, 1H), 8.46-8.45 (d, 1H), 8.28 (s, 1H), 7.77-7.75 (d, 1H), 7.33-7.31 (m, 1H), 7.12-7.05 (m, 2H), 7.02-6.98 (d, 1H), 6.77-6.74 (d, 1H), 4.1 (bs, H$_2$O), 3.54-3.51 (d, 2H), 3.42-3.38 (m, 1H), 3.30-3.22 (m, 4H), 2.96-2.89 (m, 5H), 1.17-1.15 (d, 6H).

Example 12

6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene

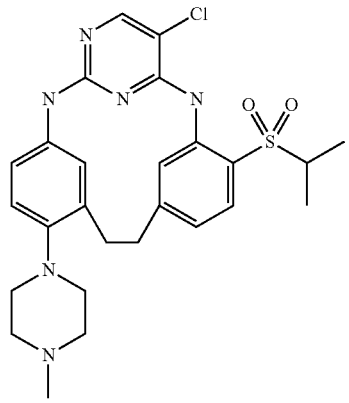 [SMILES: CC(C)S(=O)(=O)c1ccc2cc1Nc1nc(ncc1Cl)Nc1ccc(N3CCN(C)CC3)c(c1)CC2]

6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene (prepared according to Example 5) after substituting (14Z)-6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene. The workup varied in that after the extractive workup the resulting crude material was not purified via preparative HPLC, but rather via crystallization from $CH_3CN$. The desired product 6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene was isolated in 50% yield as a yellow tinted solid, mp>250° C. LC: 98% pure; LC/MS: M+H=527.2; $^1$H NMR (DMSO-d6) δ 9.47 (s, 1H), 9.27 (s, 1H), 8.36-8.35 (d, 1H), 8.25 (s, 1H), 7.99-7.97 (d, 1H), 7.71-7.69 (d, 1H), 7.28-7.26 (m, 1H), 7.04-7.02 (d, 1H), 6.95-6.92 (m, 1H), 3.31 (bs, 1H+H$_2$O), 3.04-2.98 (m, 4H), 2.81-2.79 (m, 4H), 2.5 (bs, 4H+DMSO), 2.25 (s, 3H), 1.14-1.12 (d, 6H).

Example 13

(14Z)-6-Chloro-10-methoxy-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene

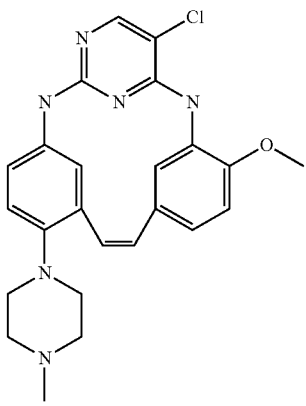 [SMILES: COc1ccc2cc1Nc1nc(ncc1Cl)Nc1ccc(N3CCN(C)CC3)c(c1)/C=C\2]

Example 13a

3-Bromo-4-(4-methyl-piperazin-1-yl)-phenylamine

3-Bromo-4-(4-methyl-piperazin-1-yl)-phenylamine was prepared in a similar manner as 3-Bromo-4-(2-pyrrolidin-1-yl-ethoxy)-phenylamine (prepared according to Example 22b) after substituting 1-(2-Bromo-4-nitro-phenyl)-4-methyl-piperazine for 1-[3-(2-bromo-4-nitro-phenoxy)-propyl]-pyrrolidine. The crude material was triturated with water to give 3-Bromo-4-(4-methyl-piperazin-1-yl)-phenylamine as a light brown solid in 93% yield, which was used without further manipulation. $^1$H NMR (DMSO-d6) δ 6.90-6.88 (d, 1H), 6.82-6.81 (d, 1H), 6.54-6.51 (m, 1H), 5.03 (s, 2H), 2.79-2.77 (m, 4H), 2.43 (bm, 2H), 2.21 (s, 3H).

Example 13b

2-Methoxy-5-vinyl-phenylamine

To a room temperature mixture of 5-bromo-2-methoxyphenylamine (610 mg, 3.0 mmol), K$_2$CO$_3$ (1.73 g, 12.5 mmol), and Pd(PPh$_3$)$_4$ (600 mg, 0.5 mmol) in 1,2-dimethoxyethane (18 mL) and water (3 mL) was added vinylboronic acid dibutyl ester (2.37 mL, 10.8 mmol). The mixture was then warmed to 90° C. for 16 h. The resulting mixture was concentrated under reduced pressure, and the residue was acidified with aqueous 1N HCl. Attempted extraction with Et$_2$O or EtOAc yielded a solid between the biphasic mix, which was filtered off. The aqueous phase of the filtrate was neutralized while cooling with 30% NaOH, and the resulting mixture was washed with EtOAc (2×). The latter EtOAc extracts were combined, dried over Na$_2$SO$_4$, filtered, and concentrated under reduced pressure to yield 320 mg (71%) of 2-Methoxy-5-vinyl-phenylamine as an oil, which was used for subsequent steps without further manipulation. $^1$H NMR (DMSO-d6) δ 6.79-6.78 (d, 1H), 6.77-6.75 (d, 1H), 6.64-6.61 (m, 1H), 6.58-6.50 (m, 1H), 5.53-5.49 (d, 1H), 5.05-5.02 (d, 1H), 4.91 (bs, 2H), 3.75 (s, 3H).

Example 13c (2,5-Dichloro-pyrimidin-4-yl)-(2-methoxy-5-vinyl-phenyl)-amine

2-Methoxy-5-vinyl-phenylamine (970 mg, 6.5 mmol), 2,4,5-trichloro-pyrimidine (1.2 g, 6.5 mmol) and EtN(i-Pr)$_2$ (1.2 mL, 7.2 mmol) were combined in DMF (9 mL) at rt and stirred for 72 hours. The reaction mixture was then diluted with ice cold water (100 mL). The resulting solid was filtered and rinsed liberally with water. The solid was further purified by trituration with methanol (2×) to yield desired (2,5-Dichloro-pyrimidin-4-yl)-(2-methoxy-5-vinyl-phenyl)-amine in 66% yield as an off white solid, LC: 97%; LC/MS: M+H=296.1; $^1$H NMR (DMSO-d6) δ 9.04 (s, 1H), 8.36 (s, 1H), 7.70 (s, 1H), 7.36-7.35 (d, 1H), 7.13-7.11 (d, 1H), 6.73-6.66 (m, 1H), 5.72-5.68 (d, 1H), 5.19-5.17 (d, 1H), 3.82 (s, 3H).

Example 13d

N(2)-[3-Bromo-4-(4-methyl-piperazin-1-yl)-phenyl]-5-chloro-N(4)-(2-methoxy-5-vinyl-phenyl)-pyrimidine-2,4-diamine N(2)-[3-Bromo-4-(4-methyl-piperazin-1-yl)-phenyl]-5-chloro-N(4)-(2-methoxy-5-vinyl-phenyl)-pyrimidine-2,4-diamine was prepared in a similar manner as N(4)-[5-Bromo-2-(propane-2-sulfonyl)-phenyl]-5-chloro-N(2)-[4-(4-methyl-piperazin-1-yl)-3-vinyl-phenyl]-pyrimidine-2,4-diamine (prepared according to Example 11c) after substituting 3-Bromo-4-(4-methyl-piperazin-1-yl)-phenylamine for 4-(4-Methyl-piperazin-1-yl)-3-vinyl-phenylamine, substituting (2,5-dichloro-pyrimidin-4-yl)-(2-methoxy-5-vinyl-phenyl)-amine for [5-Bromo-2-(propane-2-sulfonyl)-phenyl]-(2,5-dichloro-pyrimidin-4-yl)-amine, and after altering the solvent system from 2-methoxyethanol to a 1:1 mixture of tert-butyl alcohol:1,2-dimethoxyethane (120 mL of solvent for a mmol reaction). The reaction mixture was warmed for 6 days at 85° C. After concentrating the reaction mixture, the crude mix was purified straightaway via preparative HPLC. The purest fractions were then partitioned between EtOAc and saturated aqueous NaHCO$_3$. The organic phase was dried over Na$_2$SO$_4$, filtered, and concentrated under reduced pressure to give desired N(2)-[3-Bromo-4-(4-methyl-piperazin-1-yl)-phenyl]-5-chloro-N(4)-(2-methoxy-5-vinyl-phenyl)-pyrimidine-2,4-diamine in 20% yield. This material was used without further manipulation for subsequent macro-cyclization. LC: 93%; LC/MS: M+H=531.0.

Example 13e (14Z)-6-Chloro-10-methoxy-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene (14Z)-6-Chloro-10-methoxy-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene was prepared in a similar manner as (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene (prepared according to Example 4j) after substituting N(2)-[3-Bromo-4-(4-methyl-piperazin-1-yl)-phenyl]-5-chloro-N (4)-(2-methoxy-5-vinyl-phenyl)-pyrimidine-2,4-diamine for N-[2-(2,5-Dichloro-pyrimidin-4-ylamino)-4-vinyl-phenyl]-N-methyl-methanesulfonamide. The workup also varied in that desired product (14Z)-6-Chloro-10-methoxy-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene precipitated directly out of the reaction mixture. The desired product was filtered, rinsed with a small amount of ice cold CH$_3$CN, and after air drying was isolated in 94% yield as an off white solid, LC: 94%, M+H=449.1.

A small sample of the 94% pure material was further purified via preparative HPLC to return pure (14Z)-6-Chloro-10-methoxy-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene as a TFA salt white lyophylate. LC: 99%; LC/MS: M+H=449.1; $^1$H NMR (DMSO-d6) δ 9.6 (bs, 1H), 9.38 (s, 1H), 9.04-9.03 (d, 1H), 8.41-8.40 (d, 1H), 8.19 (d, 1H), 7.84 (s, 1H), 7.11-7.01 (m, 4H), 6.68-6.60 (m, 2H), 3.90 (s, 3H), 3.5-3.2 (bm, 6H+H$_2$O), 2.96-2.89 (m, 5H).

Example 14

6-Chloro-10-methoxy-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

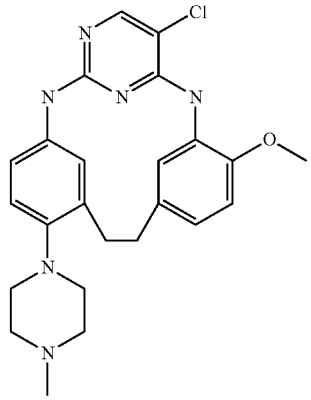 [SMILES: COc1ccc2cc1Nc1nc(ncc1Cl)Nc1ccc(N3CCN(C)CC3)c(c1)CC2]

6-Chloro-10-methoxy-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene (prepared according to Example 5) after substituting (14Z)-6-Chloro-10-methoxy-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene. The desired product 6-Chloro-10-methoxy-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene was isolated in 41% yield as a TFA salt, white lyophylate. LC: 99%; LC/MS: M+H=451.2; $^1$H NMR (DMSO-d6) δ 9.6 (bs, 1H), 9.38 (s, 1H), 8.15 (s, 1H), 8.04 (bs, 1H), 7.95 (bs, 1H), 7.92-7.91 (d, 1H), 7.06-7.03 (d, 1H), 6.98-6.92 (m, 3H), 3.83 (s, 3H), 3.61 (bs, H$_2$O), 3.53-3.50 (d, 2H), 3.25-3.22 (m, 2H), 3.10-3.07 (d, 2H), 2.99-2.96 (d, 2H), 2.92-2.87 (m, 7H).

Example 15

6-Chloro-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

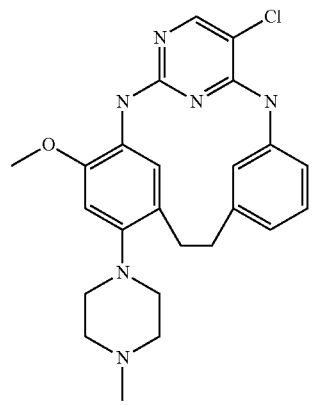 [SMILES: COc1cc(N2CCN(C)CC2)c2cc1Nc1ncc(Cl)c(n1)Nc1cccc(c1)CC2]

Example 15a (2,5-Dichloro-pyrimidin-4-yl)-3-vinyl-phenyl)-amine

3-Vinyl-phenylamine (840 mg, 7.1 mmol), 2,4,5-trichloro-pyrimidine (1.3 g, 7.1 mmol) and EtN(i-Pr)$_2$ (1.23 mL, 7.1 mmol) were combined in DMF (10 mL) at rt and stirred for 16 hours. The reaction mixture was then diluted with ice cold water. The resulting white solid was filtered and rinsed liberally with water. After air drying there remained 1.64 g (87%) of (2,5-Dichloro-pyrimidin-4-yl)-3-vinyl-phenyl)-amine as a white solid. LC: 97%; LC/MS: M+H=266.0.

Example 15b

N(2)-[5-Bromo-2-methoxy-4-(4-methyl-piperazin-1-yl)-phenyl]-5-chloro-N(4)-(3-vinyl-phenyl)-pyrimidine-2,4-diamine N(2)-[5-Bromo-2-methoxy-4-(4-methyl-piperazin-1-yl)-phenyl]-5-chloro-N(4)-(3-vinyl-phenyl)-pyrimidine-2,4-diamine was prepared in a similar manner as N-(2-{2-[5-Bromo-2-methoxy-4-(4-methyl-piperazin-1-yl)-phenylamino]-5-chloro-pyrimidin-4-ylamino}-4-vinyl-phenyl)-N-methyl-methanesulfonamide (prepared according to Example 4i) after substituting (2,5-Dichloro-pyrimidin-4-yl)-3-vinyl-phenyl)-amine for N-[2-(2,5-Dichloro-pyrimidin-4-ylamino)-4-vinyl-phenyl]-N-methyl-methanesulfonamide, and heating the reaction for 8 hours rather than 4 hours to give desired N(2)-[5-Bromo-2-methoxy-4-(4-methyl-piperazin-1-yl)-phenyl]-5-chloro-N(4)-(3-vinyl-phenyl)-pyrimidine-2,4-diamine as an oil in 10% yield. The majority of N(2)-[5-Bromo-2-methoxy-4-(4-methyl-piperazin-1-yl)-phenyl]-5-chloro-N(4)-(3-vinylphenyl)-pyrimidine-2,4-diamine was used without further manipulation for its subsequent macro-cyclization. A small sample of N(2)-[5-Bromo-2-methoxy-4-(4-methyl-piperazin-1-yl)-phenyl]-5-chloro-N(4)-(3-vinyl-phenyl)-pyrimidine-2,4-diamine was crystallized from CH$_3$CN to yield it as a white solid, mp 126-129° C. LC/MS: M+H=451.1.

Example 15c (14Z)-6-Chloro-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene (14Z)-6-Chloro-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene was prepared in a similar manner as (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene (prepared according to Example 4j) after substituting N(2)-[5-Bromo-2-methoxy-4-(4-methyl-piperazin-1-yl)-phenyl]-5-chloro-N(4)-(3-vinyl-phenyl)-pyrimidine-2,4-diamine for N-[2-(2,5-Dichloro-pyrimidin-4-ylamino)-4-vinyl-phenyl]-N-methyl-methanesulfonamide. The workup varied slightly in that the reaction mixture was concentrated under reduced pressure. The residue was partitioned between 1N HCl and EtOAc (2×). The aqueous phase was neutralized, and extracted with CHCl$_3$ (3×). The CHCl$_3$ extracts were combined, dried over Na$_2$SO$_4$, filtered, and concentrated under reduced pressure to give crude (14Z)-6-Chloro-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene in 51% yield, which was carried on for subsequent reduction towards 6-Chloro-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene without further manipulation. LC/MS: M+H=449.0.

Example 15d

6-Chloro-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

6-Chloro-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene (prepared according to Example 5) after substituting (14Z)-6-Chloro-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene. The desired product 6-Chloro-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene was isolated in 40% yield as a TFA salt, white lyophylate. LC: 99%; LC/MS: M+H=451.1; $^1$H NMR (DMSO-d6) δ 9.7 (bs, 1H), 9.36 (s, 1H), 8.14 (s, 1H), 8.12 (s, 1H), 7.90 (s, 1H), 7.76 (s, 1H), 7.25-7.21 (t, 1H), 7.05-7.03 (d, 1H), 7.00-6.98 (d, 1H), 6.69 (s, 1H), 3.81 (s, 3H), 3.70 (bs, water), 3.53 (d, 2H), 3.27-3.24 (m, 2H), 3.14-3.11 (d, 2H), 3.01-2.98 (d, 2H), 2.94 (s, 3H), 2.92-2.91 (d, 4H).

Example 16

(14Z)-6-Chloro-10-(N-methylcarboxamido)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene

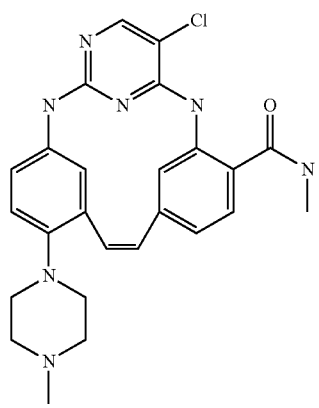 [SMILES: CNC(=O)c1ccc2cc1Nc1nc(ncc1Cl)Nc1ccc(N3CCN(C)CC3)c(c1)/C=C\2]

Example 16a

4-Bromo-2-(2,5-dichloro-pyrimidin-4-ylamino)-benzoic acid methyl ester

2-Amino-4-bromo-benzoic acid methyl ester (1.2 g, 5.0 mmol) was combined with 2,4,5-trichloro-pyrimidine (5.33 mL, 46.5 mmol) and EtN(i-Pr)$_2$ (0.95 mL, 5.5 mmol), and the mixture was warmed to 120° C. After 16 hours the excess 2,4,5-trichloro-pyrimidine was removed under high vacuum, and the residue was then treated with 1:1 MeOH:water. The resulting solid was filtered, retriturated with 1:1 MeOH:water, refiltered, and the resulting solid triturated in MeOH at 50° C. After filtering, the solid was rinsed liberally with MeOH. After air drying 4-Bromo-2-(2,5-dichloro-pyrimidin-4-ylamino)-benzoic acid methyl ester was recovered in 52% yield as a brown solid and was carried on for subsequent steps without further manipulation. LC/MS: M+H=377.9.

Example 16b

4-Bromo-2-(5-chloro-2-[4-(4-methyl-piperazin-1-yl)-3-vinyl-phenylamino]-pyrimidin-4-ylamino)-benzoic acid methyl ester 4-Bromo-2-(5-chloro-2-[4-(4-methyl-piperazin-1-yl)-3-vinyl-phenylamino]-pyrimidin-4-ylamino)-benzoic acid methyl ester was prepared in a similar manner as N-(4-Bromo-2-{5-chloro-2-[4-(4-methyl-piperazin-1-yl)-3-vinyl-phenylamino]-pyrimidin-4-ylamino}-phenyl)-N-methyl-methanesulfonamide (prepared according to Example 9f) after substituting 4-Bromo-2-(2,5-dichloro-pyrimidin-4-ylamino)-benzoic acid methyl ester for N-[4-Bromo-2-(2,5-dichloro-pyrimidin-4-ylamino)-phenyl]-N-methyl-methanesulfonamide. The desired product 4-Bromo-2-(5-chloro-2-[4-(4-methyl-piperazin-1-yl)-3-vinyl-phenylamino]-pyrimidin-4-ylamino)-benzoic acid methyl ester was isolated in 52% as a tan solid, LC: 98%; LC/MS: M+H=559.0

Example 16c

Methyl (14Z)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene-10-carboxylate Methyl (14Z)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene-10-carboxylate was prepared in a similar manner as (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene (prepared according to Example 4j) after substituting 4-Bromo-2-(5-chloro-2-[4-(4-methyl-piperazin-1-yl)-3-vinyl-phenylamino]-pyrimidin-4-ylamino)-benzoic acid methyl ester for N-[2-(2,5-Dichloro-pyrimidin-4-ylamino)-4-vinyl-phenyl]-N-methyl-methanesulfonamide. The desired product Methyl (14Z)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene-10-carboxylate was filtered directly from the reaction mixture, rinsed with CH$_3$CN and isolated in 54% yield as a bronze solid. LC: 100%; LC/MS: M+H=477.1; $^1$H NMR (DMSO-d6) δ 10.72 (s, 1H), 9.59 (s, 1H), 9.42 (s, 1H), 8.39 (s, 1H), 8.23 (s, 1H), 7.97-7.95 (d, 1H), 7.13-7.06 (m, 2H), 7.01-6.99 (d, 1H), 6.94-6.90 (d, 1H), 6.68-6.65 (d, 1H), 3.91 (s, 3H), 2.86 (s, 4H), 2.50 (s, 4H+DMSO), 2.25 (s, 3H).

Example 16d (14Z)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene-10-carboxylic acid A solution of LiOH (11 mg, 0.46 mmol) in water (0.6 mL) was added to a solution of Methyl (14Z)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene-10-carboxylate (29 mg, 0.06 mmol) in MeOH (6 mL), and the resulting mixture was warmed to 65° C. for 16 hours. After cooling to 0° C., the mixture was treated with 1N HCl (0.46 mL, 0.46 mmol), then concentrated under reduced pressure and used directly for the subsequent reaction towards (14Z)-6-Chloro-10-(N-methylcarboxamido)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene without further manipulation. LC: 100%, LC/MS: M+H=463.1.

Example 16e (14Z)-6-Chloro-10-(N-methylcarboxamido)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene N-(3-Dimethylaminopropyl)-N' ethylcarbodiimide hydrochloride (150 mg, 0.8 mmol) was added to a rt mixture of (14Z)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene-10-carboxylic acid (28 mg, 0.06 mmol), 1-hydroxybenzotriazole (11 mg, 0.084 mmol), methylammonium chloride (100 mg, 1 mmol), and triethylamine (100 µL, 0.7 mmol). After 7 days the reaction mixture was partitioned between EtOAc (2×) and saturated aqueous NaHCO$_3$. The organic phases were combined, dried over Na$_2$SO$_4$, filtered, and concentrated under reduced pressure to yield 28 mg (98%) of (14Z)-6-Chloro-10-(N-methylcarboxamido)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene, which was used for subsequent step without further manipulation. LC: 98%; LC/MS: M+H 476.2. A small sample of the 98% pure material was further purified via preparative HPLC to return pure (14Z)-6-Chloro-10-(N-methylcarboxamido)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene as a TFA salt white lyophylate. LC: 100%; LC/MS: M+H=476.1; $^1$H NMR (DMSO-d6) δ 11.55 (s, 1H), 9.55 (bs, 1H), 9.40 (s, 1H), 9.39 (s, 1H), 8.76-8.74 (m, 1H), 8.46-8.45 (d, 1H), 8.19 (s, 1H), 7.77-7.75 (d, 1H), 7.13-7.04 (m, 3H), 6.91-6.87 (d, 1H), 6.70-6.66 (d, 1H), 3.5 (d, 2H), 3.35-3.2 (bm, 4H+H$_2$O), 2.95-2.89 (m, 5H), 2.81-2.80 (d, 3H).

Example 17

6-Chloro-10-(N-methylcarboxamido)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

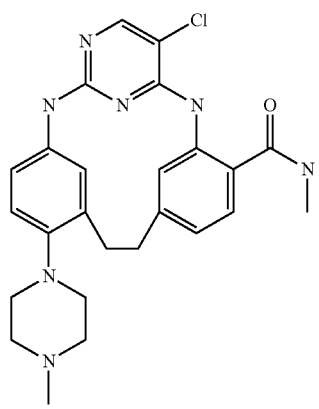 [SMILES: CNC(=O)c1ccc2cc1Nc1nc(ncc1Cl)Nc1ccc(N3CCN(C)CC3)c(c1)CC2]

6-Chloro-10-(N-methylcarboxamido)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene (prepared according to Example 5) after substituting (14Z)-6-Chloro-10-(N-methylcarboxamido)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10, 12,14,16,18-decaene. The desired product 6-Chloro-10-(N-methylcarboxamido)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-nonaene was isolated in 20% yield as a TFA salt, white lyophylate. LC: 100%; LC/MS: M+H=478.2; $^{1}$H NMR (DMSO-d6) δ 11.2 (s, 1H), 9.61 (bs, 1H), 9.38 (s, 1H), 8.66-8.65 (m, 1H), 8.40 (s, 1H), 8.18 (s, 1H), 8.08 (s, 1H), 7.70-7.67 (d, 1H), 7.08-6.96 (m, 3H), 3.53 (d, 2H), 3.26-3.23 (m, 2H), 3.12-3.09 (d, 2H), 3.0-2.93 (m, 6H), 2.91 (d, 3H), 2.79 (d, 3H).

Example 18

(14Z)-6-Chloro-10-(methanesulfonyl)-17-(4-methyl-piperazin-1-yl)-2,4,8,22-tetraazatetracyclo[14.3.1.1$^{3,7}$.1$^{9,13}$]docosa-1(20),3(22),4,6,9(21),10,12,14,16,18-decaene Trifluoroacetate (1:1)

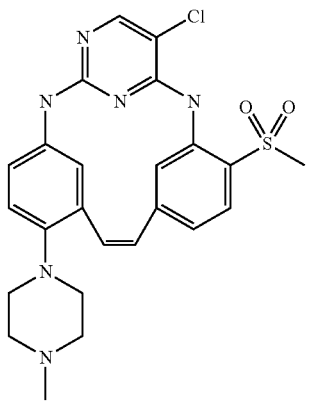 [SMILES: CN1CCN(c2ccc3cc2/C=C\c2ccc(S(C)(=O)=O)c(c2)Nc2nc(ncc2Cl)N3)CC1]

Example 18a (5-Bromo-2-methanesulfonyl-phenyl)-(2,5-dichloro-pyrimidin-4-yl)-amine

[5-Bromo-2-methanesulfonyl)-phenyl]-(2,5-dichloro-pyrimidin-4-yl)-amine was prepared in a similar manner as [5-Bromo-2-(propane-2-sulfonyl)-phenyl]-(2,5-dichloro-pyrimidin-4-yl)-amine (prepared according to Example 11a) after substituting 5-bromo-2-methanesulfonyl-phenylamine for 5-Bromo-2(propane-2-sulfonyl)-phenylamine. (5-Bromo-2-methanesulfonyl-phenyl)-(2,5-dichloro-pyrimidin-4-yl)-amine was isolated in 98% yield as a yellow solid. LC: 97%; LC/MS: M+H=397.9.

Example 18b

N(4)-(5-Bromo-2-methanesulfonyl-phenyl)-5-chloro-N(2)-[4-(4-methyl-piperazin-1-yl)-3-vinyl-phenyl]-pyrimidine-2,4-diamine N(4)-(5-Bromo-2-methanesulfonyl-phenyl)-5-chloro-N(2)-[4-(4-methyl-piperazin-1-yl)-3-vinyl-phenyl]-pyrimidine-2,4-diamine was prepared in a similar manner as N(4)-[5-Bromo-2-(propane-2-sulfonyl)-phenyl]-5-chloro-N(2)-[4-(4-methyl-piperazin-1-yl)-3-vinyl-phenyl]-pyrimidine-2,4-diamine (prepared according to Example 11c) after substituting (5-Bromo-2-methanesulfonyl-phenyl)-(2,5-dichloro-pyrimidin-4-yl)-amine for [5-Bromo-2-(propane-2-sulfonyl)-phenyl]-(2,5-dichloro-pyrimidin-4-yl)-amine N(4)-(5-Bromo-2-methanesulfonyl-phenyl)-5-chloro-N(2)-[4-(4-methyl-piperazin-1-yl)-3-vinyl-phenyl]-pyrimidine-2,4-diamine LC: 92%; LC/MS: M+H=579.0.

Example 18c (14Z)-6-Chloro-10-(methanesulfonyl)-17-(4-methyl-piperazin-1-yl)-2,4,8,22-tetraazatetracyclo[14.3.1.1$^{3,7}$.1$^{9,13}$]docosa-1(20),3(22),4,6,9(21),10,12,14,16,18-decaene Trifluoroacetate (1:1)

(14Z)-6-Chloro-10-(methanesulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene was prepared in a similar manner as (14Z)-6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene (prepared according to Example 11d) after substituting N(4)-[5-Bromo-2-(propane-2-sulfonyl)-phenyl]-5-chloro-N(2)-[4-(4-methyl-piperazin-1-yl)-3-vinyl-phenyl]-pyrimidine-2,4-diamine for N(4)-[5-Bromo-2-(propane-2-sulfonyl)-phenyl]-5-chloro-N(2)-[4-(4-methyl-piperazin-1-yl)-3-vinyl-phenyl]-pyrimidine-2,4-diamine. (14Z)-6-Chloro-10-(methanesulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene was isolated as a TFA salt, yellow lyophylate in 20% yield. LC: 100%; LC/MS: M+H=497.1.

Example 19

6-Chloro-10-(methanesulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene

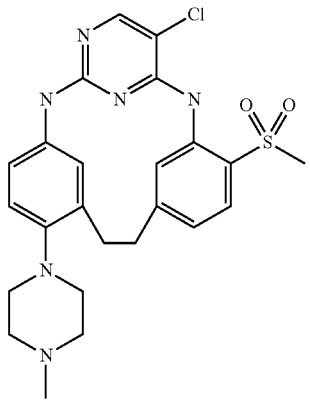 [SMILES: CN1CCN(c2ccc3cc2CCc2ccc(S(C)(=O)=O)c(c2)Nc2nc(ncc2Cl)N3)CC1]

6-Chloro-10-(methanesulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene (prepared according to Example 12) after substituting (14Z)-6-Chloro-10-(methanesulfonyl)-17-(4-methyl-piperazin-1-yl)-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(propane-2-sulfonyl)-17-(4-methylpiperazin-1-yl)-2,4,8,22-tetraazatetracyclo[14.3.1.1$^{3,7}$.1$^{9,13}$]

docosa-1(20),3(22),4,6,9(21),10,12,14,16,18-decaene. The desired product 6-Chloro-10-(methanesulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene was isolated in 20% yield as a yellow tinted solid, mp>250° C. LC: 97%; LC/MS: M+H=499.1; $^1$H NMR (DMSO-d6) δ 9.41 (s, 1H), 9.08 (s, 1H), 8.35 (s, 1H), 8.24 (s, 1H), 7.98-7.97 (d, 1H), 7.77-7.75 (d, 1H), 7.27-7.25 (d, 1H), 7.03-7.01 (d, 1H), 6.93-6.90 (m, 1H), 3.21 (s, 3H), 3.08-2.99 (m, 4H), 2.80-2.78 (m, 4H), 2.50 (bm, 4H+DMSO), 2.25 (s, 3H).

Example 20

(14Z)-6-Chloro-10-methoxy-17-(morpholin-4-yl)-2,4,8,22-tetraazatetracyclo[14.3.1.1$^{3,7}$.1$^{9,13}$]docosa-1(20),3(22),4,6,9(21),10,12,14,16,18-decaene

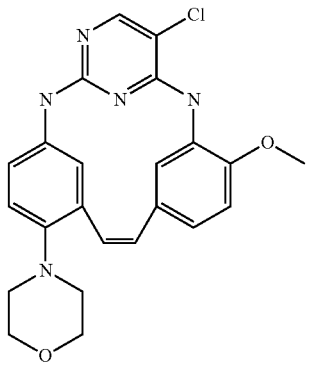 [SMILES: COc1ccc2cc1Nc1nc(ncc1Cl)Nc1ccc(N3CCOCC3)c(c1)/C=C\2]

Example 20a

N(2)-[3-Bromo-4-morpholin-4-yl-phenyl]-5-chloro-N(4)-(2-methoxy-5-vinyl-phenyl)-pyrimidine-2,4-diamine N(2)-[3-Bromo-4-morpholin-4-yl-phenyl]-5-chloro-N(4)-(2-methoxy-5-vinyl-phenyl)-pyrimidine-2,4-diamine was prepared in a similar manner as N(2)-[3-Bromo-4-(4-methyl-piperazin-1-yl)-phenyl]-5-chloro-N(4)-(2-methoxy-5-vinyl-phenyl)-pyrimidine-2,4-diamine (prepared according to Example 13d) after substituting 3-Bromo-4-morpholin-4-yl-phenylamine for 3-Bromo-4-(4-methyl-piperazin-1-yl)-phenylamine and after altering the solvent system from 2-methoxy-ethanol to a 1:1 mixture of tert-butyl alcohol:1,2-dimethoxyethane (120 mL of solvent for a mmol reaction). The reaction mixture was warmed for 6 days at 85° C., followed by the standard workup using EtOAc for the extractive workup. Some desired N(2)-[3-Bromo-4-morpholin-4-yl-phenyl]-5-chloro-N(4)-(2-methoxy-5-vinyl-phenyl)-pyrimidine-2,4-diamine crystalized relatively pure from EtOAc on concentrating the filtrate, the remainder was purified via normal phase chromatography to yield the desired product N(2)-[3-Bromo-4-morpholin-4-yl-phenyl]-5-chloro-N(4)-(2-methoxy-5-vinyl-phenyl)-pyrimidine-2,4-diamine in 55% overall yield as a yellow tinted solid, mp 186-190° C. LC: 100%; LC/MS: M+H=518.0; $^1$H NMR (DMSO-d6) δ 9.36 (s, 1H), 8.23 (s, 1H), 8.16 (s, 1H), 7.95 (s, 1H), 7.8 (s, 1H), 7.58-7.57 (m, 1H), 7.33-7.32 (m, 1H), 7.13-7.11 (d, 1H), 6.96-6.94 (d, 1H), 6.7-6.6 (m, 1H), 5.67-5.62 (d, 1H), 5.13-5.10 (d, 1H), 3.85 (s, 3H), 3.74-3.71 (m, 4H), 2.88-2.85 (m, 4H).

Example 20b (14Z)-6-Chloro-10-methoxy-17-(morpholin-4-yl)-2,4,8,22-tetraazatetracyclo[14.3.1.1$^{3,7}$.1$^{9,13}$]docosa-1(20),3(22),4,6,9(21),10,12,14,16,18-decaene (14Z)-6-Chloro-10-methoxy-17-(morpholin-4-yl)-2,4,8,22-tetraazatetracyclo[14.3.1.1$^{3,7}$.1$^{9,13}$]docosa-1(20),3(22),4,6,9(21),10,12,14,16,18-decaene was prepared in a similar manner as was Methyl (14Z)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene-10-carboxylate (prepared according to Example 16c) after substituting N(2)-[3-Bromo-4-morpholin-4-yl-phenyl]-5-chloro-N(4)-(2-methoxy-5-vinyl-phenyl)-pyrimidine-2,4-diamine for 4-Bromo-2-(5-chloro-2-[4-(4-methyl-piperazin-1-yl)-3-vinyl-phenylamino]-pyrimidin-4-ylamino)-benzoic acid methyl ester. The desired product (14Z)-6-Chloro-10-methoxy-17-(morpholin-4-yl)-2,4,8,22-tetraazatetracyclo[14.3.1.1$^{3,7}$.1$^{9,13}$]docosa-1(20),3(22),4,6,9(21),10,12,14,16,18-decaene was isolated in 53% yield as a gray solid, LC: 87%, LC/MS: M+H=436.2.

Example 21

6-Chloro-10-methoxy-17-(morpholin-4-yl)-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

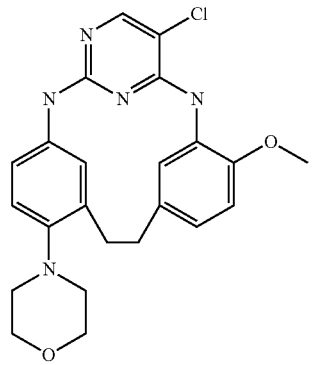 [SMILES: COc1ccc2cc1Nc1nc(ncc1Cl)Nc1ccc(N3CCOCC3)c(c1)CC2]

6-Chloro-10-methoxy-17-(morpholin-4-yl)-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene (prepared according to Example 12) after substituting (14Z)-6-Chloro-10-methoxy-17-(morpholin-4-yl)-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene. The desired product 6-Chloro-10-methoxy-17-(morpholin-4-yl)-2,4,8,22-tetraazatetracyclo[14.3.1.1$^{3,7}$.1$^{9,13}$]docosa-1(20),3(22),4,6,9(21),10,12,16,18-nonaene was isolated in 19% yield as a TFA salt, white lyophylate. LC: 99%; LC/MS: M+H=438.22; $^1$H NMR (DMSO-d6) δ

9.38 (bs, 1H), 8.20 (bs, 1H), 8.16 (s, 1H), 7.93 (s, 1H), 7.87-7.86 (d, 1H), 7.05-6.90 (m, 4H), 3.84 (s, 3H), 3.76-3.74 (m, 4H), 3.5 (bs, H2O), 2.96-2.89 (M, 4H), 2.80-2.78 (m, 4H).

Example 22

(14Z)-6-Chloro-17-[2-(pyrrolidin-1-yl)ethoxy]-2,4,8, 22-tetraazatetracyclo[14.3.1.1$^{3,7}$.1$^{9,13}$]docosa-1(20), 3(22),4,6,9(21),10,12,14,16,18-decaene

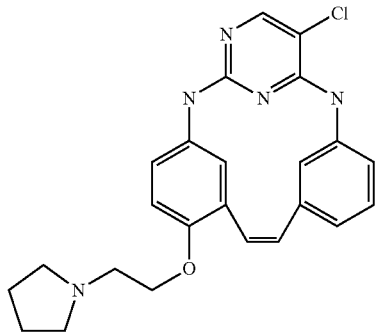 [SMILES: Clc1cnc2nc1Nc1cccc(c1)/C=C\c1cc(ccc1OCCN1CCCC1)N2]

Example 22a

1-[3-(2-bromo-4-nitro-phenoxy)-propyl]-pyrrolidine

A mixture of 2-Bromo-1-fluoro-4-nitro-benzene (1.10 g, 5.0 mmol), N-β-hydroxyethylpyrrolidine (6.0 mL, 52 mmol), and K$_2$CO$_3$ (1.38 g, 10 mmol) was warmed to 100° C. for 24 h. The mixture was cooled to rt and diluted with water. The resulting solid was filtered, rinsed with water, and air dried to yield 1.32 g (84%) of 1-[3-(2-bromo-4-nitrophenoxy)-propyl]-pyrrolidine as a copper colored solid. LC: 93%; $^1$H NMR (DMSO-d6) δ 8.43-8.42 (d, 1H), 8.28-8.25 (m, 1H), 7.36-7.34 (d, 1H), 4.36-4.31 (t, 2H), 2.88-2.86 (t, 2H), 2.58-2.55 (m, 4H), 1.70-1.67 (m, 4H).

Example 22b

3-Bromo-4-(2-pyrrolidin-1-yl-ethoxy)-phenylamine

1-[3-(2-bromo-4-nitro-phenoxy)-propyl]-pyrrolidine (0.74 g, 2.3 mmol) was combined with RaNi (120 mg) in ethanol (EtOH) (50 mL) and the mixture was warmed to reflux. Hydrazine hydrate (1.0 mL, 2 mmol) was added dropwise to the refluxing solution and the elevated temperature was maintained for 1 h. After cooling, the reaction mixture was filtered, and the filtrate concentrated under reduced pressure to yield 0.58 g (87%) of 3-Bromo-4-(2-pyrrolidin-1-yl-ethoxy)-phenylamine as a brown oil, which was used without further manipulation. LC/MS: M+H=285.30.

Example 22c

N(2)-[3-Bromo-4-(2-pyrrolidin-1-yl-ethoxy)-phenyl]-5-chloro-N(4)-(3-vinyl-phenyl)-pyrimidine-2,4-diamine N(2)-[3-Bromo-4-(2-pyrrolidin-1-yl-ethoxy)-phenyl]-5-chloro-N(4)-(3-vinyl-phenyl)-pyrimidine-2,4-diamine was prepared in a similar manner as N(2)-[3-Bromo-4-(4-methyl-piperain-1-yl)-phenyl]-5-chloro-N(4)-(3-vinyl-phenyl)-pyrimidine-2,4-diamine (prepared according to Example 2a) after substituting 3-Bromo-4-(2-pyrrolidin-1-yl-ethoxy)-phenylamine for 3-Bromo-4-(4-methyl-piperazin-1-yl)-phenylamine. The desired product N(2)-[3-Bromo-4-(2-pyrrolidin-1-yl-ethoxy)-phenyl]-5-chloro-N(4)-(3-vinyl-phenyl)-pyrimidine-2,4-diamine was isolated in 52% as white solid, M+H=515.4

Example 22d (14Z)-6-Chloro-17-[2-(pyrrolidin-1-yl)ethoxy]-2,4,8, 22-tetraazatetracyclo[14.3.1.1$^{3,7}$.1$^{9,13}$]docosa-1(20), 3(22),4,6,9(21),10,12,14,16,18-decaene (14Z)-6-Chloro-17-[2-(pyrrolidin-1-yl)ethoxy]-2,4,8,22-tetraazatetracyclo[14.3.1.1$^{3,7}$.1$^{9,13}$]docosa-1(20),3(22),4,6,9(21),10,12,14,16,18-decaene was prepared in a similar manner as Methyl (14Z)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene-10-carboxylate (prepared according to Example 16c) after substituting N(2)-[3-Bromo-4-(2-pyrrolidin-1-yl-ethoxy)-phenyl]-5-chloro-N(4)-(3-vinyl-phenyl)-pyrimidine-2,4-diamine for 4-Bromo-2-(5-chloro-2-[4-(4-methyl-piperazin-1-yl)-3-vinyl-phenylamino]-pyrimidin-4-ylamino)-benzoic acid methyl ester. The desired product (14Z)-6-Chloro-17-[2-(pyrrolidin-1-yl)ethoxy]-2,4,8,22-tetraazatetracyclo[14.3.1.1$^{3,7}$.1$^{9,13}$]docosa-1(20),3(22),4,6,9(21),10,12,14,16,18-decaene was isolated in 62% yield as an copper colored solid. LC: 100%; LC/MS: M+H=434.1; $^1$H NMR (DMSO-d6) δ 9.7 (bs, 1H), 9.24 (s, 1H), 9.11 (s, 1H), 8.63 (s, 1H), 8.51 (d, 1H), 8.12 (s, 1H), 7.29-7.25 (t, 1H), 7.21-7.19 (d, 1H), 7.04-6.99 (m, 2H), 6.96-6.94 (d, 1H), 6.89-6.86 (d, 1H), 6.73-6.70 (d, 1H), 4.28-4.26 (m, 2H), 3.64-3.56 (bm, 2H+water), 3.18 (m, 2H), 2.07 (bm, 2H), 1.91-1.89 (m, 2H).

Example 23

6-Chloro-17-[2-(pyrrolidin-1-yl)ethoxy]-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

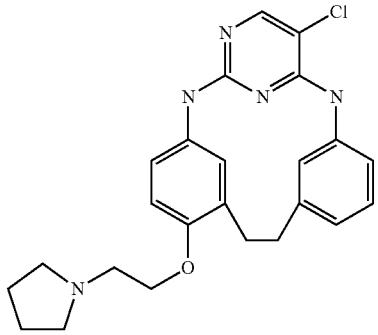 [SMILES: Clc1cnc2nc1Nc1cccc(c1)CCc1cc(ccc1OCCN1CCCC1)N2]

6-Chloro-17-[2-(pyrrolidin-1-yl)ethoxy]-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene (prepared according to Example 12) after substituting (14Z)-6-Chloro-17-[2-(pyrrolidin-1-yl)ethoxy]-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene. The workup varied slightly in that after the addition of water no solid precipitated, so the aqueous solution was partitioned between saturated aqueous NaHCO$_3$ and EtOAc. The organic phase was dried over Na$_2$SO$_4$, filtered, and concentrated under reduced pressure. The residue was purified via preparative HPLC. The desired product 6-Chloro-17-[2-(pyrrolidin-1-yl)ethoxy]-2,4,8,22-tetraazatetracyclo[14.3.1.1$^{3,7}$.1$^{9,13}$]docosa-1(20),3(22),4,6,9(21),10,12,16,18-nonaene was isolated as a TFA salt, white lyophylate in 40% yield. LC: 100%; LC/MS: M+H=436.1; $^1$H NMR (DMSO-d6) δ 9.7 (bs, 1H), 9.16 (s, 1H), 9.05 (s, 1H), 8.09 (s, 1H), 7.82 (s, 1H), 7.80 (s, 1H), 7.23-7.19 (t, 1H), 7.07-7.05 (d, 1H), 6.97-6.95 (d, 1H), 6.88 (m, 2H), 4.25-4.23 (m, 2H), 3.64 (bs, 2H+H$_2$O), 3.20 (m, 2H), 2.91 (s, 4H), 2.08 (m, 2H), 1.91 (m, 2H).

Example 24

(14Z)-6-Chloro-17-(morpholin-4-yl)-2,4,8,22-tetraazatetracyclo[14.3.1.1$^{3,7}$.1$^{9,13}$]docosa-1(20),3(22),4,6,9(21),10,12,14,16,18-decaene

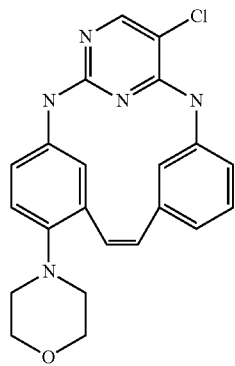 [SMILES: Clc1cnc2nc1Nc1cccc(c1)CCc1cc(ccc1N1CCOCC1)N2]

Example 24a

N(2)-(3-Bromo-4-morpholin-4-yl-phenyl)-5-chloro-N(4)-3-vinyl-phenyl)-pyrimidine-2,4-diamine (2,5-Dichloro-pyrimidin-4-yl)-3-vinyl-phenyl)-amine (270 mg, 1.0 mmol), 3-bromo-4-morpholin-4-yl-phenylamine (260 mg, 1.0 mmol), and 4.0 M HCl in dioxane (280 μL, 1.10 mmol) were combined in 2-methoxy-ethanol (11 mL) and warmed to 110° C. for 16 hours. The resulting solution was concentrated under reduced pressure and the residue was partitioned between ethyl acetate and saturated aqueous NaHCO$_3$. The organic phase was dried over Na$_2$SO$_4$, filtered, and concentrated under reduced pressure. The residue was triturated with CH$_3$CN, filtered, and rinsed with a small amount of CH$_3$CN to yield N(2)-(3-Bromo-4-morpholin-4-yl-phenyl)-5-chloro-N(4)-3-vinyl-phenyl)-pyrimidine-2,4-diamine in 71% as white solid, mp 142-144° C. LC: 91%; LC/MS: M+H=406.1; $^1$H NMR (DMSO-d6) δ 9.37 (s, 1H), 8.86 (s, 1H), 8.16 (s, 1H), 7.85 (s, 1H), 7.70 (s, 1H), 7.63-7.60 (m, 2H), 7.38-7.34 (t, 1H), 7.28-7.26 (d, 1H), 6.99-6.96 (d, 1H), 6.76-6.68 (m, 1H), 5.81-5.77 (d, 1H), 5.27-5.24 (d, 1H), 3.73-3.71 (m, 4H), 2.88-2.86 (m, 4H).

Example 24b (14Z)-6-Chloro-17-(morpholin-4-yl)-2,4,8,22-tetraazatetracyclo[14.3.1.1$^{3,7}$.1$^{9,13}$]docosa-1(20),3(22),4,6,9(21),10,12,14,16,18-decaene Palladium acetate (Pd(OAc)$_2$) (35 mg, 0.16 mmol), tri-o-tolylphosphine (220 mg, 0.71 mmol), and N(2)-(3-Bromo-4-morpholin-4-yl-phenyl)-5-chloro-N(4)-3-vinyl-phenyl)-pyrimidine-2,4-diamine (150 mg, 0.31 mmol) were combined with CH$_3$CN (4 mL) and triethylamine (Et$_3$N) (300 μL, 2 mmol). The mixture was treated under microwave irradiation at 120° C. for 30 minutes. After cooling, the resulting solid was filtered and rinsed with ice cold CH$_3$CN. After the CH$_3$CN trituration, the sample was also triturated with ethyl ether (Et$_2$O). The desired product (14Z)-6-Chloro-17-(morpholin-4-yl)-2,4,8,22-tetraazatetracyclo[14.3.1.1$^{3,7}$.1$^{9,13}$]docosa-1(20),3(22),4,6,9(21),10,12,14,16,18-decaene was isolated in 43% yield as an off white solid, mp 267-270° C. LC: 95%; LC/MS: M+H=406.1; $^1$H NMR (DMSO-d6) δ 9.18 (s, 1H), 9.03 (s, 1H), 8.65 (s, 1H), 8.44-8.43 (d, 1H), 8.10 (s, 1H), 7.27-7.23 (t, 1H), 7.18-7.16 (d, 1H), 7.01-6.97 (m, 2H), 6.95-6.93 (d, 1H), 6.85-6.82 (d, 1H), 6.72-6.68 (d, 1H), 3.76-3.75 (m, 4H), 2.84 (m, 4H).

Example 25

6-Chloro-17-(morpholin-4-yl)-2,4,8,22-tetraazatetracyclo[14.3.1.1$^{3,7}$.1$^{9,13}$]docosa-1(20),3(22),4,6,9(21),10,12,16,18-nonaene

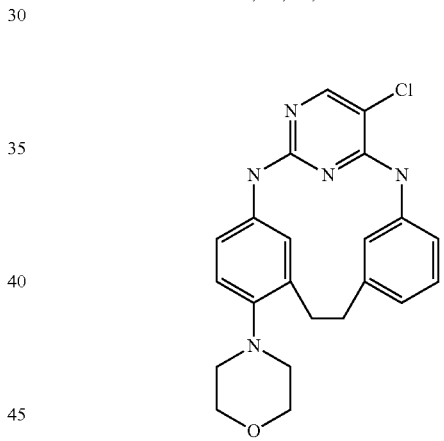

At rt dipotassium azodicarboxylate (784 mg, 4.0 mmol) was added to a solution of (14Z)-6-Chloro-17-(morpholin-4-yl)-2,4,8,22-tetraazatetracyclo[14.3.1.1$^{3,7}$.1$^{9,13}$]docosa-1(20),3(22),4,6,9(21),10,12,14,16,18-decaene (70 mg, 0.172 mmol) in pyridine (10 mL). The resulting mixture was treated with acetic acid (AcOH) (0.56 mL, 9.8 mmol). After 3 days the reaction mixture was treated with additional portions of dipotassium azodicarboxylate (330 mg, 1.7 mmol) and AcOH (0.28 mL, 4.9 mmol) and warmed to 35° C. for two days (LC supported reaction >95% complete). The mixture was then combined with water and the resulting solid was collected. This solid was dissolved in DMSO and purified via preparative HPLC to yield 28 mg (31%) of desired 6-Chloro-17-(morpholin-4-yl)-2,4,8,22-tetraazatetracyclo[14.3.1.1$^{3,7}$.1$^{9,13}$]docosa-1(20),3(22),4,6,9(21),10,12,16,18-nonaene as a white lyophylate. LC: 100%; LC/MS: M+H=408.2; $^1$H NMR (DMSO-d6) δ 9.47 (bs, 2H), 8.16 (s, 1H), 7.95-7.94 (d, 1H), 7.80 (s, 1H), 7.25-7.21 (t, 1H), 7.05-7.00 (m, 3H), 6.91-6.88 (m, 1H), 3.76-3.74 (m, 4H), 3.02-2.96 (m, 4H), 2.78-2.77 (m, 4H).

Example 26

(14R,15S)-6-chloro-2,4,8,22-tetraazatetracyclo[14.3.1.1$^{3,7}$.1$^{9,13}$]docosa-1(20),3(22),4,6,9(21),10,12,16,18-nonaene-14,15-diol

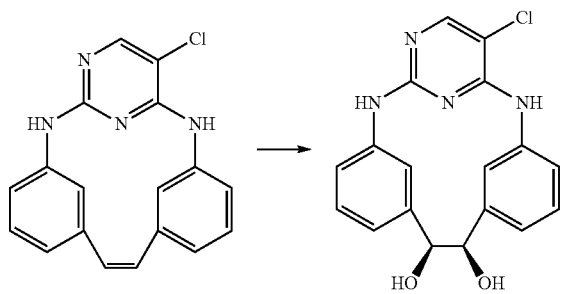 [SMILES: Clc1cnc2nc1Nc1cccc(c1)/C=C\c1cccc(c1)N2 ; O[C@@H]1c2cccc(c2)Nc2nc(ncc2Cl)Nc2cccc(c2)[C@@H]1O]

4.8 M N-Methylmorpholine N-oxide in water (300 μL, 1 mmol) was added to a solution of (14Z)-6-Chloro-2,4,8,22-tetraazatetracyclo[14.3.1.1$^{3,7}$.1$^{9,13}$]docosa-1(20),3(22),4,6,9(21),10,12,14,16,18-decaene (110 mg, 0.34 mmol) in THF (15 mL) and then a solution of potassium osmate, dihydrate (25 mg, 0.068 mmol) in water (1 mL) was added and the mixture was warmed to 55° C. After 1.5 h, added acetone (5 mL) and additional water (1 mL), then heating was continued an additional 2 hours. The reaction mixture was concentrated under reduced pressure, the residue dissolved in 1000 uL of DMSO, filtered and purified via preparative reverse phase HPLC. The front running material was lyophilized to yield 6 mg (5%) of desired product (14R,15S)-6-chloro-2,4,8,22-tetraazatetracyclo[14.3.1.1$^{3,7}$.1$^{9,13}$]docosa-1(20),3(22),4,6,9(21),10,12,16,18-nonaene-14,15-diol as a white lyophylate. LC: 98%; LC/MS: M+H=355.1; NMR (DMSO-d6) δ 8.12 (s, 1H), 7.79 (s, 1H), 7.73 (s, 1H), 7.29-7.08 (m, 5H), 6.99-6.97 (d, 1H), 4.80 (s, 1H), 4.5 (s, 1H).

Example 27

(14R,15S)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene-14,15-diol

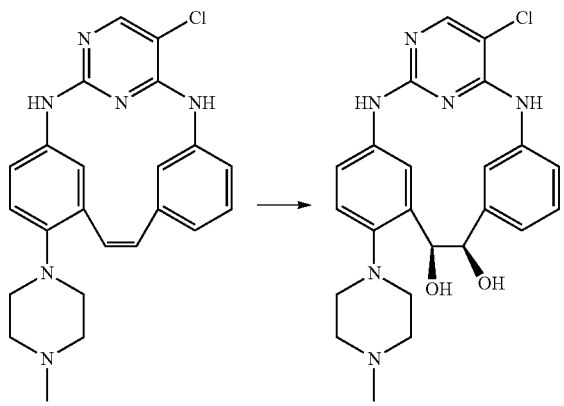 [SMILES: CN1CCN(c2ccc3cc2/C=C\c2cccc(c2)Nc2nc(ncc2Cl)N3)CC1 ; CN1CCN(c2ccc3cc2[C@H](O)[C@H](O)c2cccc(c2)Nc2nc(ncc2Cl)N3)CC1]

A room temperature solution of (14Z)-6-Chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene (65 mg, 0.16 mmol) in pyridine (3 mL) was treated with a 0.2 M aqueous solution of osmium tetraoxide (1.04 mL, 0.163 mmol). After 4.5 h the mixture was treated with a 0.5 M aqueous solution of sodium sulfite (1 mL, 0.50 mmol), which was stirred for 5 minutes. The mixture was extracted twice with CHCl$_3$. The organic phases were combined, dried over Na$_2$SO$_4$, filtered, and concentrated under reduced pressure. The residue was purified via preparative reverse phase HPLC to yield 4 mg (6%) of desired (14R,15S)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene-14,15-diol as a brown lyophylate. LC: 100%; LC/MS: M+H=453.1; NMR (CDCl$_3$/MeOH-d4) δ 8.06 (s, 1H), 7.99-7.98 (d, 1H), 7.82 (bs, 1H), 7.46-7.44 (d, 1H), 7.38-7.34 (m, 1H), 7.22-7.20 (d, 1H), 7.12-7.11 (d, 1H), 7.04-7.02 (m, 1H), 5.6 (s, 1H), 4.85 (2H+H$_2$0), 3.60-3.43 (m, 6H), 3.13-3.10 (m, 2H), 3.01 (s, 3H).

Example 28

6-Chloro-10-(2-methanesulfonyl-methyl-amino)-17-(piperidin-4-yl)-19-methoxy-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

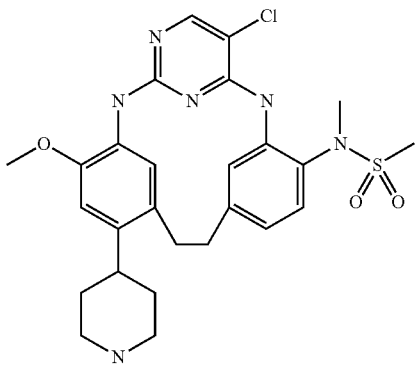

Under an inert atmosphere at rt 6-chloro-10-[2-methanesulfonyl-methyl-amino]-19-methoxy-17-(1-methyl-piperidin-4-yl)-2,4,8,22-tetraazatetracyclo[14.3.1.1$^{3,7}$.1$^{9,13}$]docosa-1(20),3(22),4,6,9(21),10,12,16,18-nonaene (8 mg, 0.014 mmol) in CHCl$_3$ (3 mL) was treated with N,N-diisopropylethylamine (32 μL, 0.19 mmol) followed by α-chloroethyl chloroformate (18 μL, 0.17 mmol). The resulting mixture was warmed to 60° C. for 1 hour, and then concentrated under reduced pressure. The resulting residue was treated with methanol (5 mL) and warmed to 50° C. for 1 hour. The reaction mixture was again concentrated under reduced pressure; the residue was dissolved in DMSO and purified by preparative HPLC yielding the desired 6-Chloro-10-(2-methanesulfonyl-methyl-amino)-17-(piperidin-4-yl)-19-methoxy-2,4,8,22-tetraazatetracyclo[14.3.1.1$^{3,7}$.1$^{9,13}$]docosa-1(20),3(22),4,6,9(21),10,12,16,18-nonaene as a TFA salt, white lyophylate (58%). LC: 97%; LC/MS: M+H=543.1; $^1$H NMR (DMSO-d6) δ 8.59-8.56 (bd, 1H, exchangeable), 8.28-8.24 (bm, 3H, exchangeable), 8.17 (s, 1H), 8.11 (s, 1H), 7.70 (s, 1H), 7.48-7.46 (d, 1H, J=8.36 Hz), 7.08-7.06 (d, 1H, J=8.25 Hz), 6.71 (s, 1H), 3.79 (s, 3H), 3.40-3.38 (d, 2H), 3.17 (s, 3H), 3.12-2.94 (m, 9H), 1.92-1.80 (m, 4H).

Example 29

N-[(20S)-6-chloro-24-methoxy-20-(morpholin-4-yl)-2,4,8,27-tetraazapentacyclo[14.8.1.1$^{3,7}$.1$^{9,13}$.0$^{17,23}$]heptacosa-1(25),3(27),4,6,9(26),10,12,16,23-nonaen-10-yl]N-methylmethanesulfonamide

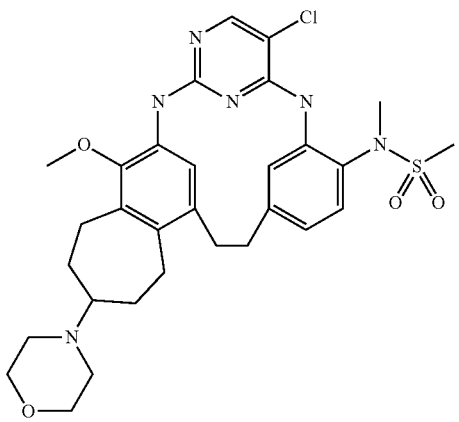 [SMILES: COc1c2cc(c3c1CCC(N1CCOCC1)CC3)CCc1ccc(N(C)S(C)(=O)=O)c(c1)Nc1nc(ncc1Cl)N2]

Example 29a

N-{2-[2-(4-Bromo-1-methoxy-7-morpholin-4-yl-6,7,8,9-tetrahydro-5H-benzocyclohepten-2-ylamino)-5-chloro-pyrimidin-4-ylamino]-4-vinyl-phenyl}-N-methylsulfonamide N-{2-[2-(4-Bromo-1-methoxy-7-morpholin-4-yl-6,7,8,9-tetrahydro-5H-benzocyclohepten-2-ylamino)-5-chloro-pyrimidin-4-ylamino]-4-vinyl-phenyl}-N-methylsulfonamide was prepared in a similar manner as N-(2-{2-[5-Bromo-2-methoxy-4-(4-methyl-piperazin-1-yl)-phenylamino]-5-chloro-pyrimidin-4-ylamino}-4-vinyl-phenyl)-N-methyl-methanesulfonamide (prepared as in Example 4i) after substituting 4-Bromo-1-methoxy-7-morpholin-4-yl-6,7,8,9-tetrahydro-5H-benzocyclohepten-2-ylamine for 5-Bromo-2-methoxy-4-(4-methyl-piperazin-1-yl)-phenylamine. The crude reaction mixture was concentrated under reduced pressure and the residue purified via preparative HPLC yielding N-{2-[2-(4-Bromo-1-methoxy-7-morpholin-4-yl-6,7,8,9-tetrahydro-5H-benzocyclohepten-2-ylamino)-5-chloro-pyrimidin-4-ylamino]-4-vinyl-phenyl}-N-methylsulfonamide as a TFA salt white lyophylate in 30% yield, which was used for the subsequent reaction without further manipulation. LC: 94%; LC/MS: M+H=693.0.

Example 29b

N-[(14Z,20S)-6-chloro-24-methoxy-20-(morpholin-4-yl)-2,4,8,27-tetraazapentacyclo[14.8.1.1$^{3,7}$.1$^{9,13}$.0$^{17,23}$]heptacosa-1(25),3(27),4,6,9(26),10,12,14,16,23-decaen-10-yl]N-methylmethanesulfonamide N-[(14Z,20S)-6-chloro-24-methoxy-20-(morpholin-4-yl)-2,4,8,27-tetraazapentacyclo[14.8.1.1$^{3,7}$.1$^{9,13}$.0$^{17,23}$]heptacosa-1(25),3(27),4,6,9(26),10,12,14,16,23-decaen-10-yl]N-methylmethanesulfonamide was prepared in a similar manner as Methyl (14Z)-6-chloro-17-(4-methylpiperazin-1-yl)-2,4,8,22-tetraazatetracyclo[14.3.1.1$^{3,7}$.1$^{9,13}$]docosa-1(20),3(22),4,6,9(21),10,12,14,16,18-decaene-10-carboxylate (prepared as in Example 16c) after substituting N-{2-[2-(4-Bromo-1-methoxy-7-morpholin-4-yl-6,7,8,9-tetrahydro-5H-benzocyclohepten-2-ylamino)-5-chloro-pyrimidin-4-ylamino]-4-vinyl-phenyl}-N-methylsulfonamide for 4-Bromo-2-(5-chloro-2-[4-(4-methyl-piperazin-1-yl)-3-vinyl-phenylamino]-pyrimidin-4-ylamino)-benzoic acid methyl ester. The desired product N-[(14Z,20S)-6-chloro-24-methoxy-20-(morpholin-4-yl)-2,4,8,27-tetraazapentacyclo[14.8.1.1$^{3,7}$.1$^{9,13}$.0$^{17,23}$]heptacosa-1(25),3(27),4,6,9(26),10,12,14,16,23-decaen-10-yl]N-methylmethanesulfonamide was isolated in 68% yield as a black tinted solid. LC: 96%; LC/MS: M+H=611.1.

Example 29c

N-[(20S)-6-chloro-24-methoxy-20-(morpholin-4-yl)-2,4,8,27-tetraazapentacyclo[14.8.1.1$^{3,7}$.1$^{9,13}$.0$^{17,23}$]heptacosa-1(25),3(27),4,6,9(26),10,12,16,23-nonaen-10-yl]N-methylmethanesulfonamide N-[(20S)-6-chloro-24-methoxy-20-(morpholin-4-yl)-2,4,8,27-tetraazapentacyclo[14.8.1.1$^{3,7}$.1$^{9,13}$.0$^{17,23}$]heptacosa-1(25),3(27),4,6,9(26),10,12,16,23-nonaen-10-yl]N-methylmethanesulfonamide was prepared in a similar manner as 6-Chloro-10-(propane-2-sulfonyl)-17-(4-methylpiperazin-1-yl)-2,4,8,22-tetraazatetracyclo[14.3.1.1$^{3,7}$.1$^{9,13}$]docosa-1(20),3(22),4,6,9(21),10,12,16,18-nonaene (prepared as in Example 12) after substituting N-[(14Z,20S)-6-chloro-24-methoxy-20-(morpholin-4-yl)-2,4,8,27-tetraazapentacyclo[14.8.1.1$^{3,7}$.1$^{9,13}$.0$^{17,23}$]heptacosa-1(25),3(27),4,6,9(26),10,12,14,16,23-decaen-10-yl]N-methylmethanesulfonamide for (14Z)-6-Chloro-10-(propane-2-sulfonyl)-17-(4-methyl-piperazin-1-yl)-2,4,8,22-tetraazatetracyclo[14.3.1.1$^{3,7}$.1$^{9,13}$]docosa-1(20),3(22),4,6,9(21),10,12,14,16,18-decaene. The workup varied slightly in that after the addition of water no solid precipitated, so the aqueous solution was partitioned between saturated aqueous NaHCO$_3$ and EtOAc. The organic phase was dried over Na$_2$SO$_4$, filtered, and concentrated under reduced pressure. The residue was purified via preparative HPLC. The desired product N-[(20S)-6-chloro-24-methoxy-20-(morpholin-4-yl)-2,4,8,27-tetraazapentacyclo[14.8.1.1$^{3,7}$.1$^{9,13}$.0$^{17,23}$]heptacosa-1(25),3(27),4,6,9(26),10,12,16,23-nonaen-10-yl]N-methylmethanesulfonamide was isolated as a TFA salt, white lyophylate in 41% yield. LC: 97%; LC/MS: M+H=613.1; $^1$H NMR (DMSO-d6) δ 9.51 (bm, 1H, exchangeable), 8.62 (s, 1H, exchangeable), 8.27 (s, 1H, exchangeable), 8.24 (s, 1H), 8.21 (s, 1H), 7.58 (s, 1H), 7.48-7.46 (d, 1H), 7.06-7.04 (d, 1H), 3.98-3.95 (d, 2H), 3.72-3.66 (m, 2H), 3.59 (s, 3H), 3.50-2.94 (bm, 17H+water), 2.58-2.37 (4H+DMSO), 1.44-1.39 (m, 2H).

Example 30

6-Trifluoromethyl-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

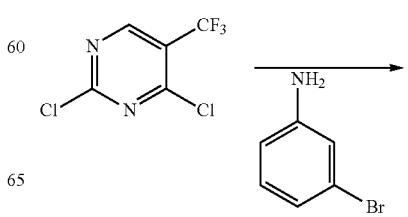

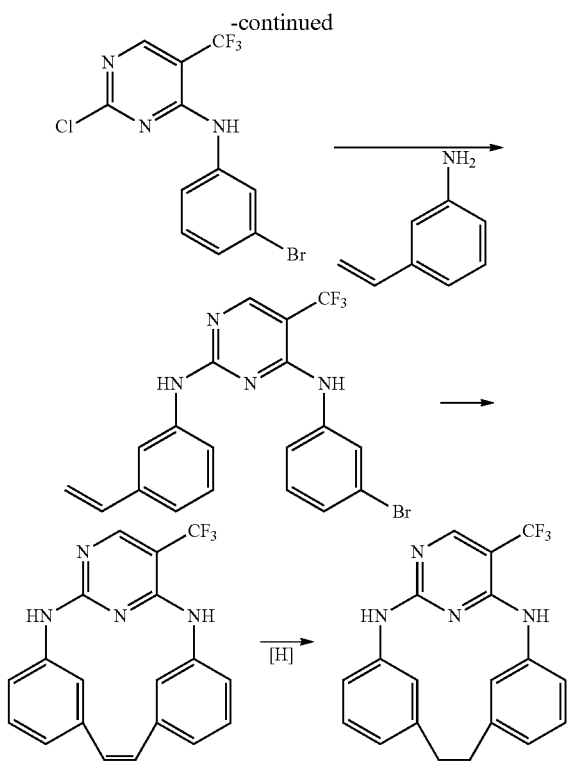

Example 30a (3-Bromo-phenyl)-2-chloro-5-trifluoromethyl-pyrimidin-4-yl)-amine (3-Bromo-phenyl)-2-chloro-5-trifluoromethyl-pyrimidin-4-yl)-amine was prepared in a similar manner as (2,5-Dichloro-pyrimidin-4-yl)-(2-methoxy-5-vinyl-phenyl)-amine (prepared as in Example 13c) after substituting 2,4-dichloro-5-trifluoromethylpyrimidine for 2,4,5-trichloropyrimidine and 3-bromoaniline for 2-methoxy-5-vinyl-phenylamine The crude mixture was concentrated under reduced pressure and partitioned between organic and saturated aqueous NaHCO₃. The organic phase was dried under Na₂SO₄, filtered, and concentrated. The crude (3-Bromo-phenyl)-2-chloro-5-trifluoromethyl-pyrimidin-4-yl)-amine was purified by normal phase chromatography (ethyl acetate/hexane), after which it was used for the subsequent reaction without further manipulation.

Example 30b

N(4)-(3-Bromo-phenyl)-5-trifluoromethyl-N(2)-(3-vinyl-phenyl)-pyrimidine-2,4-diamine N(4)-(3-Bromo-phenyl)-5-trifluoromethyl-N(2)-(3-vinyl-phenyl)-pyrimidine-2,4-diamine was prepared in a similar manner as N-(2-{2-[5-Bromo-2-methoxy-4-(4-methyl-piperazin-1-yl)-phenylamino]-5-chloro-pyrimidin-4-ylamino}-4-vinyl-phenyl)-N-methyl-methanesulfonamide (prepared as in Example 4i) after substituting (3-Bromo-phenyl)-2-chloro-5-trifluoromethyl-pyrimidin-4-yl)-amine for N-[2-(2,5-Dichloro-pyrimidin-4-ylamino)-4-vinyl-phenyl]-N-methyl-methanesulfonamide, 3-vinyl-phenylamine for 5-Bromo-2-methoxy-4-(4-methyl-piperazin-1-yl)-phenylamine, and 4M HCl in dioxane for methanesulfonic acid.

The crude N(4)-(3-Bromo-phenyl)-5-trifluoromethyl-N(2)-(3-vinyl-phenyl)-pyrimidine-2,4-diamine was purified via preparative reverse phase HPLC, then free based by partitioning between CHCl₃ and saturated aqueous NaHCO₃. The organic phase was dried over Na₂SO₄, filtered, and concentrated to give N(4)-(3-Bromo-phenyl)-5-trifluoromethyl-N(2)-(3-vinyl-phenyl)-pyrimidine-2,4-diamine, which was used for the subsequent step without further manipulation.

Example 30c (14Z)-6-Trifluoromethyl-2,4,8,22-tetraazatetracyclo[14.3.1.1$^{3,7}$.1$^{9,13}$]docosa-1(20),3(22),4,6,9(21),10,12,14,16,18-decaene (14Z)-6-Trifluoromethyl-2,4,8,22-tetraazatetracyclo[14.3.1.1$^{3,7}$.1$^{9,13}$]docosa-1(20),3(22),4,6,9(21),10,12,14,16,18-decaene was prepared in a similar manner as (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene (prepared as in Example 4j) after substituting N(4)-(3-Bromo-phenyl)-5-trifluoromethyl-N(2)-(3-vinyl-phenyl)-pyrimidine-2,4-diamine for N-(2-{2-[5-Bromo-2-methoxy-4-(4-methyl-piperazin-1-yl)-phenylamino]-5-chloro-pyrimidin-4-ylamino}-4-vinyl-phenyl)-N-methyl-methanesulfonamide. The workup varied in that (14Z)-6-Trifluoromethyl-2,4,8,22-tetraazatetracyclo[14.3.1.1$^{3,7}$.1$^{9,13}$]docosa-1(20),3(22),4,6,9(21),10,12,14,16,18-decaene was purified chromatographically rather than via crystallization. MP:167-169° C., LC: 95%; LC/MS: M+H=355.1.

Example 30d

6-Trifluoromethyl-2,4,8,22-tetraazatetracyclo[14.3.1.1$^{3,7}$.1$^{9,13}$]docosa-1(20),3(22),4,6,9(21),10,12,16,18-nonaene Trifluoroacetate (1:1)

6-Trifluoromethyl-2,4,8,22-tetraazatetracyclo[14.3.1.1$^{3,7}$.1$^{9,13}$]docosa-1(20),3(22),4,6,9(21),10,12,16,18-nonaene was prepared in a similar manner as 6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,16,18-nonaene (prepared as in Example 5) after substituting (14Z)-6-Trifluoromethyl-2,4,8,22-tetraazatetracyclo[14.3.1.1$^{3,7}$.1$^{9,13}$]docosa-1(20),3(22),4,6,9(21),10,12,14,16,18-decaene for (14Z)-6-Chloro-10-(2-methanesulfonyl-methyl-amino)-17-(4-methylpiperazin-1-yl)-19-methoxy-2,4,8,22-tetraazatetracyclo[14.3.1.1$^{3,7}$.1$^{9,13}$]docosa-1(20),3(22),4,6,9(21),10,12,14,16,18-decaene. The desired 6-Trifluoromethyl-2,4,8,22-tetraazatetracyclo[14.3.1.1$^{3,7}$.1$^{9,13}$]docosa-1(20),3(22),4,6,9(21),10,12,16,18-nonaene was isolated as a white lyophylate. LC: 100%, LC/MS: M+H=357.1.

VI. Biology

ALK Kinase Assay

Example compounds were tested for their ability to inhibit the kinase activity of baculovirus-expressed ALK using a modification of the ELISA protocol reported for trkA in Angeles, T. S. et al., *Anal. Biochem.* 1996, 236, 49-55, which is incorporated herein by reference in its entirety. Phosphorylation of the substrate, phospholipase C-gamma (PLC-γ) generated as a fusion protein with glutathione S-transferase (GST) as reported in Rotin, D. et al., *EMBO J.* 1992, 11, 559-567, which is incorporated herein by reference in its entirety, was detected with a europium-labeled anti-phosphotyrosine antibody and measured by time-resolved fluorescence (TRF). Briefly, each 96-well plate was coated with 100 μL/well of 10 μg/mL substrate (GST-PLC-γ) in Tris-buffered saline (TBS). The assay mixture (total volume=100 μL/well) consisting of 20 mM HEPES, pH 7.2, 1 μM ATP ($K_m$ level), 5 mM MnCl$_2$, 0.1% BSA, 2.5% DMSO, and various concentrations of test compound was then added to the assay plate. The reaction was initiated by adding enzyme (30 ng/mL ALK) and was allowed to proceed at 37° C. for 15 minutes. Detection of the phosphorylated product was performed by adding 100 μL/well of Eu—N1 labeled PT66 antibody (Perkin Elmer #AD0041). Incubation at 37° C. then proceeded for 1 hour, followed by addition of 100 μL enhancement solution (Wallac #1244-105). The plate was gently agitated and after thirty minutes, the fluorescence of the resulting solution was measured using the PerkinElmer EnVision™ 2102 (or 2104) multilabel plate reader.

Data analysis was performed using ActivityBase (IDBS, Guilford, UK). IC$_{50}$ values were calculated by plotting percent inhibition versus log$_{10}$ of the concentration of compound and fitting to the nonlinear regression sigmoidal dose-response (variable slope) equation in XLFit (IDBS, Guilford, UK).

JAK2 Kinase Assay

Compounds were tested for their ability to inhibit the kinase activity of baculovirus-expressed JAK2 using the TRF detection system. IC$_{50}$ runs were conducted in 96-well Costar high binding plates (Corning Costar #3922, Corning, N.Y.). The plates were coated first with 100 μL/well of 10 μg/mL Neutravidin (Pierce #31000, Rockford, Ill.) in TBS at 37° C. for 2 hours, followed by 100 μL/well of 1 μg/mL 15-mer peptide substrate (biotinyl-amino-hexanoyl-EQEDEPEGDYFEWLE-amide, Infinity Biotech Research and Resource, Aston, Pa.) at 37° C. for another hour. The JAK2 assay mixture (total volume=100 μL/well) consisting of 20 mM HEPES, pH 7.2, 0.2 μM ATP, 1 mM MnCl$_2$, 0.1% BSA, and test compound (diluted in DMSO; 2.5% DMSO final in assay) was then added to the assay plate. Enzyme (15 ng/ml JAK2) was added and the reaction was allowed to proceed at room temperature for 20 minutes. Detection of the phosphorylated product was performed by adding 100 μL/well of Eu—N1 labeled PY100 antibody (PerkinElmer Life Sciences #AD0041, Boston, Mass.). Incubation at the room temperature then proceeded for 1 hour, followed by addition of 100 μl enhancement solution (PerkinElmer Life Sciences #1244-105, Boston, Mass.). The plate was gently agitated and after thirty minutes, the fluorescence of the resulting solution was measured using the PerkinElmer EnVision™ 2102 (or 2104) multi-label plate reader.

Data analysis was performed using ActivityBase (IDBS, Guilford, UK). IC$_{50}$ values were calculated by plotting percent inhibition versus log$_{10}$ of the concentration of compound and fitting to the nonlinear regression sigmoidal dose-response (variable slope) equation in XLFit (IDBS, Guilford, UK).

FAK Enzyme Assay

Example compounds were tested for their ability to inhibit the kinase activity of baculovirus-expressed recombinant human FAK using the TRF detection system as described above for JAK2. IC$_{50}$ runs were performed in 96-well Costar high binding plates (#3922). The plates were coated first with 100 μL/well of 10 μg/mL neutravidin in TBS at 37° C. for 2 h, followed by 100 μL/well of 1 μg/mL 15-mer peptide substrate (biotinyl-amino-hexanoyl-EQEDEPEGDY-FEWLE-amide) at 37° C. for another hour. The FAK assay mixture (total volume=100 μL/well) consisting of 20 mM HEPES, pH 7.2, 10 μM ATP, 5 mM MgCl$_2$, 0.5 mM DTT, 0.1% BSA, and test compound (diluted in DMSO; 2.5% DMSO final in assay) was then added to the assay plate. Enzyme (10 ng/mL FAK, Invitrogen #PV3832) was added and the reaction was allowed to proceed at room temperature for 30 minutes. Detection of the phosphorylated product was performed by adding 100 μL/well of Eu—N1 labeled PY100 antibody (diluted 1:75000 in antibody dilution buffer). Samples were incubated at room temperature for 1 hour, followed by addition of 100 μL enhancement solution. Plates were agitated for 10 minutes and fluorescence of the resulting solution measured using the PerkinElmer EnVision™ 2102 (or 2104) multi-label plate reader.

Data analysis was performed using ActivityBase (IDBS, Guilford, UK). IC$_{50}$ values were calculated by plotting percent inhibition versus log$_{10}$ of the concentration of compound and fitting to the nonlinear regression sigmoidal dose-response (variable slope) equation in XLFit (IDBS, Guilford, UK).

Insulin Receptor Kinase Assay

Example compounds were tested for their ability to inhibit the kinase activity of baculovirus-expressed human insulin receptor cytoplasmic domain (βIR$_{CD}$) using the TRF assay as described above for ALK. Phosphorylation of the substrate, recombinant GST-PLC-γ, was detected with a europium-labeled anti-phosphotyrosine antibody and measured by TRF. Each 96-well plate (Greiner#655074) was coated with 100 μL/well of 20 μg/mL substrate solution in TBS. The IR assay mixture (total volume=100 μL/well) consisting of 20 mM HEPES (pH 7.2), 20 μM ATP, 5 mM MnCl$_2$, 0.1% BSA, and test compound (diluted in DMSO; 2.5% DMSO final in assay) was added to the assay plates. Enzyme (20 ng/mL βIR$_{CD}$) was added and the reaction was allowed to proceed at room temperature for 20 minutes. Detection of the phosphorylated product was performed by adding 100 μL/well of Eu—N1 labeled PY100 antibody (PerkinElmer#AD0160; diluted 1:10,000 in TBS-T containing 0.25% BSA). Incubation at 37° C. for 1 hour was followed by addition of 50 μL enhancement solution (Wallace#1244-105). Plates were agitated for 10 minutes and the fluorescence was measured using the PerkinElmer EnVision™ 2102 or 2104 multi-label plate reader.

Data analysis was performed using ActivityBase (IDBS, Guilford, UK). IC$_{50}$ values were calculated by plotting percent inhibition versus log$_{10}$ of the concentration of compound and fitting to the nonlinear regression sigmoidal dose-response (variable slope) equation in XLFit (IDBS, Guilford, UK).

Results

Biological data for Example compounds is presented in the following Table 1. Unless otherwise specified in Table 1, IC$_{50}$ nanomolar value ranges designated as A, B, C, D or E, indicate the following ranges:

IC$_{50}$<10 nM A;

IC$_{50}$ 10 nM to 100 nM B;

IC$_{50}$ 101 nM to 1,000 nM C;

IC$_{50}$ 1,001 nM to 10,000 nM D; and

IC$_{50}$>10,000 nM E.

"NT" denotes not tested.

Unless otherwise specified, all values are an average of two or more determinations.

TABLE 1

ALK, JAK2, FAK, Insulin Receptor Kinase Inhibition

| Example No. | FAK IC$_{50}$ (nM) | ALK IC$_{50}$ (nM) | JAK2 IC$_{50}$ (nM) | IR IC$_{50}$ (nM) |
|---|---|---|---|---|
| 1 | E | E | C | NT |
| 24 | E | >3000 | A | E |
| 25 | E | E | A | E |
| 2 | C | C | A | D |
| 3 | C | B | A | C |
| 4 | >3000 | C | A | D |
| 26 | >1000 | D | A | >3000 |
| 21 | E | E | A | E |
| 20 | NT | NT | NT | NT |
| 14 | B | A | A | C |
| 13 | C | C | B | >3000 |
| 15 | C | A | B | C |
| 22 | C | C | A | D |
| 23 | B | C | A | C |
| 30 | D | >3000 | C | NT |
| 18 | B | C | B | NT |
| 16 | C | C | B | NT |
| 27 | D | C | B | NT |
| 19 | B | B | B | C |
| 17 | A | B | A | C |
| 11 | B | B | A | D |
| 12 | A | A | A | B |
| 9 | A | B | A | >2000 |
| 10 | A | A | A | C |
| 29 | B | B | C | >3000 |
| 4 | A | A | C | >2000 |
| 5 | A | A | B | B |
| 6 | A | A | C | B |
| 7 | A | B | D | >2000 |
| 8 | A | A | C | C |
| 28 | A | A | B | C |

What is claimed is:

1. A compound of Formula I

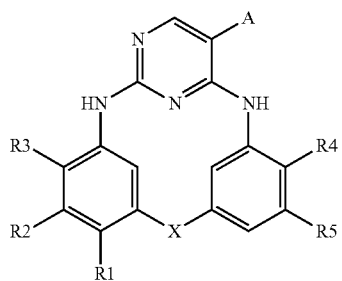

Formula I wherein:

A is H, cyano, F, Cl, Br, CH$_3$ or CF$_3$;

R1 is H, heterocyclyl, heteroaryl, carbocyclyl, aryl, C$_{1-6}$alkyl, C$_{1-6}$alkoxy, carbocyclyloxy, or C$_{1-6}$alkylamino, where, when R1 is a nitrogen containing heterocyclyl, the nitrogen may be substituted with C$_{1-6}$alkyl, hydroxy (C$_{2-3}$)alkyl, dihydroxy (C$_3$)alkyl, C$_{1-6}$alkoxy(C$_{2-3}$)alkyl, aminocarbonyl(C$_{1-3}$)alkyl, N-(C$_{1-6}$)alkylaminocarbonyl(C$_{1-3}$)alkyl, N,N-di-(C$_{1-6}$)alkylaminocarbonyl(C$_{1-3}$)alkyl, where the (C$_{1-6}$)alkyl groups of N,N-di-(C$_{1-6}$)alkylaminocarbonyl(C$_{1-3}$)alkyl may be the same or different, (C$_{1-6}$alkyl)sulfonyl-(C$_{2-3}$)alkyl, (C$_{1-6}$ alkyl)sulfonyl, amino(C$_{2-3}$)alkylcarbonyl, N-(C$_{1-6}$alkyl)amino(C$_{2-3}$)alkylcarbonyl, N,N-(di-C$_{1-6}$alkyl)amino(C$_{2-3}$)alkylcarbonyl, where the alkyl groups of N,N-(di-C$_{1-6}$alkyl)amino(C$_{2-3}$)alkylcarbonyl may be the same or different, heteroaryl or heterocyclyl, and where, when R1 is heterocyclyl, heteroaryl, carbocyclyl, or aryl, such heterocyclyl, heteroaryl, carbocyclyl, or aryl may be unsubstituted, or substituted with one or two substituents independently selected from the group consisting of C$_{1-6}$alkyl, hydroxyl, hydroxy(C$_{1-3}$)alkyl, C$_{1-6}$alkoxy, C$_{1-6}$alkoxy(C$_{1-3}$)alkyl, aminocarbonyl-(C$_{1-3}$)alkyl, N-(C$_{1-6}$)alkylaminocarbonyl(C$_{1-3}$)alkyl, N,N-di-(C$_{1-6}$)alkylaminocarbonyl(C$_{1-3}$)alkyl, where the (C$_{1-6}$)alkyl groups of N,N-di-(C$_{1-6}$)alkylaminocarbonyl(C$_{1-3}$)alkyl may be the same or different, (C$_{1-6}$alkyl)sulfonyl(C$_{1-3}$)alkyl, amino, (C$_{1-6}$)alkylamino, di-(C$_{1-6}$)alkylamino, where the alkyl groups of di-(C$_{1-6}$)alkylamino may be the same or different, (C$_{1-6}$)alkylsulfonyl, fluorine, carboxy, amino(C$_{1-3}$) alkylcarbonyl, N-(C$_{1-6}$alkyl)amino(C$_{1-3}$)alkylcarbonyl, N,N-(di-C$_{1-6}$alkyl)amino(C$_{1-3}$)alkylcarbonyl, where the alkyl groups of N,N-(di-C$_{1-6}$alkyl)amino(C$_{1-3}$) alkylcarbonyl may be the same or different, and heterocyclyl, and where, when R1 is C$_{1-6}$alkyl, C$_{1-6}$alkoxy, or C$_{1-6}$alkylamino, the alkyl groups of such C$_{1-6}$alkyl, C$_{1-6}$alkoxy, or C$_{1-6}$alkylamino may be unsubstituted, or substituted with one, two or three substituents independently selected from the group consisting of heterocyclyl, heteroaryl, hydroxyl, amino, (C$_{1-6}$)alkylamino, di-(C$_{1-6}$)alkylamino, where the alkyl groups of di-(C$_{1-6}$) alkylamino may be the same or different, carboxy, aminocarbonyl, N-(C$_{1-6}$)alkylaminocarbonyl, N,N-di-(C$_{1-6}$)alkylaminocarbonyl, where the alkyl groups of N,N-di-(C$_{1-6}$)alkylaminocarbonyl may be the same or different, aminosulfonyl, and C$_{1-6}$alkylsulfonyl;

R2 is H, heterocyclyl, heteroaryl, carbocyclyl, aryl, C$_{1-6}$alkyl, C$_{1-6}$alkoxy, or C$_{1-6}$alkylamino, where, when R2 is a nitrogen containing heterocyclyl, the nitrogen may be substituted with H, C$_{1-6}$alkyl, hydroxy (C$_{2-3}$)alkyl, dihydroxy (C$_3$)alkyl, C$_{1-6}$alkoxy(C$_{2-3}$) alkyl, aminocarbonyl(C$_{1-3}$)alkyl, N-(C$_{1-6}$)alkylaminocarbonyl(C$_{1-3}$)alkyl, N,N-di-(C$_{1-6}$) alkylaminocarbonyl(C$_{1-3}$)alkyl, where the (C$_{1-6}$)alkyl groups of N,N-di-(C$_{1-6}$)alkylaminocarbonyl(C$_{1-3}$)alkyl may be the same or different, (C$_{1-6}$alkyl)sulfonyl-(C$_{2-3}$)alkyl, (C$_{1-6}$ alkyl)sulfonyl, amino(C$_{2-3}$)alkylcarbonyl, N-(C$_{1-6}$alkyl)amino(C$_{2-3}$)alkylcarbonyl, N,N-(di-C$_{1-6}$alkyl)amino(C$_{2-3}$)alkylcarbonyl, where the alkyl groups of N,N-(di-C$_{1-6}$alkyl)amino(C$_{2-3}$)alkylcarbonyl may be the same or different, heteroaryl or heterocyclyl, and where, when R2 is heterocyclyl, heteroaryl, carbocyclyl, or aryl, such heterocyclyl, heteroaryl, carbocyclyl, or aryl may be unsubstituted, or substituted with one or two substituents independently selected from the group consisting of C$_{1-6}$alkyl, hydroxyl, hydroxy(C$_{1-3}$)alkyl, C$_{1-6}$alkoxy, C$_{1-6}$alkoxy(C$_{1-3}$)alkyl, aminocarbonyl-(C$_{1-3}$)alkyl, N-(C$_{1-6}$)alkylaminocarbonyl(C$_{1-3}$)alkyl, N,N-di-(C$_{1-6}$)alkylaminocarbonyl(C$_{1-3}$)alkyl, where the (C$_{1-6}$)alkyl groups of N,N-di-(C$_{1-6}$)alkylaminocarbonyl(C$_{1-3}$)alkyl may be the same or different, (C$_{1-6}$alkyl)sulfonyl(C$_{1-3}$)alkyl, amino, (C$_{1-6}$)alkylamino, di-(C$_{1-6}$)alkylamino, where the alkyl groups of di-(C$_{1-6}$)alkylamino may be the same or different, (C$_{1-6}$)alkylsulfonyl, fluoro, carboxy, amino(C$_{1-3}$)alkylcarbonyl, N-(C$_{1-6}$alkyl)amino(C$_{1-3}$)alkylcarbonyl, N,N-(di-C$_{1-6}$alkyl)amino(C$_{1-3}$)alkylcarbonyl, where the alkyl groups of N,N-(di-C$_{1-6}$alkyl)amino(C$_{1-3}$) alkylcarbonyl may be the same or different, and heterocyclyl, and where, when R2 is $C_{1-6}$alkyl, $C_{1-6}$alkoxy, or $C_{1-6}$alkylamino, the alkyl groups of such $C_{1-6}$alkyl, $C_{1-6}$alkoxy, or $C_{1-6}$alkylamino may be unsubstituted, or substituted with one, two or three substituents independently selected from the group consisting of heterocyclyl, heteroaryl, hydroxyl, amino, $(C_{1-6})$alkylamino, di-$(C_{1-6})$alkylamino, where the alkyl groups of di-$(C_{1-6})$alkylamino may be the same or different, carboxy, aminocarbonyl, N-$(C_{1-6})$alkylaminocarbonyl, N,N-di-$(C_{1-6})$alkylaminocarbonyl, where the alkyl groups of N,N-di-$(C_{1-6})$alkylaminocarbonyl may be the same or different, aminosulfonyl, and $C_{1-6}$alkylsulfonyl; or R1 and R2, together with the phenyl ring to which they are attached, form a five- to eight-membered monocarbocyclic or monoheterocyclic ring, where the ring so formed by R1 and R2, may be unsubstituted, or substituted with one to three substituents independently selected from the group consisting of $C_{1-6}$alkyl, amino$(C_{1-3})$alkyl, N-$(C_{1-6}$alkyl)amino$(C_{1-3})$alkyl, N,N-di-$(C_{1-6}$alkyl)amino$(C_{1-3})$alkyl, where the alkyl groups of N,N-di-$(C_{1-6}$alkyl)amino$(C_{1-3})$alkyl may be the same or different, alkoxy$(C_{1-6})$alkyl, hydroxyl, hydroxy-$(C_{1-6})$alkyl, $(C_{1-6}$alkyl)sulfonyl$(C_{1-3})$alkyl, heterocyclyl, amino, $(C_{1-6})$alkylamino, di-$(C_{1-6})$alkylamino, where the alkyl groups of di-$(C_{1-6})$alkylamino may be the same or different, carboxy, aminocarbonyl, N-$(C_{1-6})$alkylaminocarbonyl, N,N-di-$(C_{1-6})$alkylaminocarbonyl, where the alkyl groups of N,N-di-$(C_{1-6})$alkylaminocarbonyl may be the same or different, aminocarbonyl$(C_{1-3})$alkyl N-$(C_{1-6})$alkylaminocarbonyl$(C_{1-3})$alkyl, N,N-di-$(C_{1-6})$alkylaminocarbonyl$(C_{1-3})$alkyl, where the $(C_{1-6})$alkyl groups of N,N-di-$(C_{1-6})$alkylaminocarbonyl$(C_{1-3})$alkyl may be the same or different, and aminosulfonyl;

R3 is H, $C_{1-6}$alkoxy, or Cl;

where at least one of R1 and R3 is other than H;

R4 and R5, independently, are H, $C_{1-6}$alkoxy, aminocarbonyl, N-$(C_{1-6}$alkyl)aminocarbonyl, N,N-di-$(C_{1-6}$alkyl)aminocarbonyl, where the alkyl groups of N,N-di-$(C_{1-6}$alkyl)aminocarbonyl may be the same or different, $(C_{1-6}$alkyl)sulfonyl, aminosulfonyl, N-$(C_{1-6}$alkyl)aminosulfonyl, N,N-di-$(C_{1-6}$alkyl)aminosulfonyl, where the alkyl groups of N,N-di-$(C_{1-6}$alkyl)aminosulfonyl may be the same or different, N-[$(C_{1-6}$alkyl)sulfonyl]amino, N-[$(C_{1-6}$alkyl)sulfonyl]-N-$(C_{1-6}$alkyl)amino, where the alkyl groups of N-[$(C_{1-6}$alkyl)sulfonyl]-N-$(C_{1-6}$alkyl)amino may be the same or different, $(C_{1-6}$alkyl)$_2$phosphinyl, where the alkyl groups of $(C_{1-6}$alkyl)$_2$phosphinyl may be the same or different, or heteroaryl, where, when R4 or R5 is heteroaryl, such heteroaryl may be unsubstituted, or substituted with one or two substituents independently selected from the group consisting of $C_{1-6}$alkyl, hydroxyl, hydroxy$(C_{1-3})$alkyl, $C_{1-6}$alkoxy, $C_{1-6}$alkoxy$(C_{1-3})$alkyl, aminocarbonyl$(C_{1-3})$alkyl, N-$(C_{1-6})$alkylaminocarbonyl$(C_{1-3})$alkyl, N,N-di-$(C_{1-6})$alkylaminocarbonyl$(C_{1-3})$alkyl, where the $(C_{1-6})$alkyl groups of N,N-di-$(C_{1-6})$alkylaminocarbonyl$(C_{1-3})$alkyl may be the same or different, $(C_{1-6}$alkyl)sulfonyl$(C_{1-3})$alkyl, amino, $(C_{1-6})$alkylamino, di-$(C_{1-6})$alkylamino, where the alkyl groups of di-$(C_{1-6})$alkylamino may be the same or different, $(C_{1-6}$alkyl)sulfonyl, fluorine, carboxy, aminocarbonyl, N-$(C_{1-6})$alkylaminocarbonyl, and N,N-di-$(C_{1-6})$alkylaminocarbonyl, where the alkyl groups of N,N-di-$(C_{1-6})$alkylaminocarbonyl may be the same or different, and where, when R4 or R5 is N-$(C_{1-6}$alkyl)aminocarbonyl or $C_{1-6}$alkoxy, the alkyl groups of such N-$(C_{1-6}$alkyl)aminocarbonyl or $C_{1-6}$alkoxy may be unsubstituted, or substituted by one, two or three substituents indepently selected from the group consisting of heterocyclyl, hydroxyl, amino, $(C_{1-6})$alkylamino, di-$(C_{1-6})$alkylamino, where the alkyl groups of di-$(C_{1-6})$alkylamino may be the same or different, cyano, carboxy, aminocarbonyl, N-$(C_{1-6}$alkyl)aminocarbonyl, N,N-di-$(C_{1-6}$alkyl)aminocarbonyl, where the alkyl groups of N,N-di-$(C_{1-6}$alkyl)aminocarbonyl may be the same or different, or R4 and R5, together with the phenyl ring to which the are attached, form a five- to eight-membered monoheterocyclic ring, where the ring so-formed by R4 and R5 may be unsubstituted, or substituted with one or two substituents independently selected from the group consisting of $C_{1-6}$alkyl, amino$(C_{1-3})$alkyl, N-$(C_{1-6}$alkyl)amino$(C_{1-3})$alkyl, N,N-di-$(C_{1-6}$alkyl)amino$(C_{1-3})$alkyl, where the alkyl groups of N,N-di-$(C_{1-6}$alkyl)amino$(C_{1-3})$alkyl may be the same or different, alkoxy$(C_{1-6})$alkyl, hydroxyl, hydroxy$(C_{1-6})$alkyl, $(C_{1-6}$alkyl)sulfonyl, $(C_{1-6}$alkyl)sulfonyl$(C_{1-3})$alkyl, heterocyclyl, amino, $(C_{1-6})$alkylamino, di-$(C_{1-6})$alkylamino, where the alkyl groups of di-$(C_{1-6})$alkylamino may be the same or different, carboxy, aminocarbonyl, N-$(C_{1-6}$alkyl)aminocarbonyl, N,N-di-$(C_{1-6}$alkyl)aminocarbonyl, where the alkyl groups of N,N-di-$(C_{1-6}$alkyl)aminocarbonyl may be the same or different, aminocarbonyl$(C_{1-3})$alkyl, N-$(C_{1-6}$alkyl)aminocarbonyl$(C_{1-3})$alkyl, N,N-di-$(C_{1-6}$alkyl)aminocarbonyl$(C_{1-3})$alkyl, where the $(C_{1-6}$alkyl) groups of N,N-di-$(C_{1-6}$alkyl)aminocarbonyl$(C_{1-3})$alkyl may be the same or different, and aminosulfonyl; and —X— is —CH=CH—, —CH$_2$CH$_2$—, —NH—CO—, —CONH— or —(CH(OH))$_2$—; or a pharmaceutically acceptable salt thereof.

2. A compound according to claim 1 wherein A is Cl, CH$_3$ or CF$_3$.

3. A compound according to claim 2 wherein A is Cl.

4. A compound according to claim 1 wherein R1 is $C_{1-6}$alkylamino, $C_{1-6}$alkoxy where $C_{1-6}$alkoxy is substituted by heterocyclyl, heterocyclyl, or R1 and R2, together with the phenyl ring to which they are attached, form a five- to eight-membered monocarbocyclic ring.

5. A compound according to claim 4 wherein R1 is $C_{1-6}$alkoxy where $C_{1-6}$alkoxy is substituted by heterocyclyl, or heterocyclyl.

6. A compound according to claim 5 wherein R1 is heterocyclyl.

7. A compound according to claim 1 wherein R2 is H, or R1 and R2, together with the phenyl ring to which they are attached, form a five- to eight-membered monocarbocyclic ring.

8. A compound according to claim 7 wherein R2 is H.

9. A compound according to claim 1 wherein R3 is $C_{1-6}$alkoxy or H.

10. A compound according to claim 1 wherein R4 is H, $C_{1-6}$alkoxy, N-$(C_{1-6}$alkyl)aminocarbonyl, $(C_{1-6}$alkyl)sulfonyl, N-[$(C_{1-6}$alkyl)sulfonyl]-N-$(C_{1-6}$alkyl)amino, where the alkyl groups of N-[$(C_{1-6}$alkyl)sulfonyl]-N-$(C_{1-6}$alkyl)amino may be the same or different, or heteroaryl.

11. A compound according to claim 10 wherein R4 is H, $C_{1-6}$alkoxy, N-$(C_{1-6}$alkyl)aminocarbonyl, $(C_{1-6}$alkyl)sulfonyl, or N-[$(C_{1-6}$alkyl)sulfonyl]-N-$(C_{1-6}$alkyl)amino, where the alkyl groups of N-[$(C_{1-6}$alkyl)sulfonyl]-N-$(C_{1-6}$alkyl)amino may be the same or different.

12. A compound according to claim 1 wherein R5 is H, N-($C_{1-6}$alkyl)aminosulfonyl, or N,N-di-($C_{1-6}$alkyl)aminosulfonyl, where the alkyl groups of N,N-di-($C_{1-6}$alkyl)aminosulfonyl may be the same or different.

13. A compound according to claim 1 wherein:
A is Cl, $CH_3$ or $CF_3$;
R1 is $C_{1-6}$alkylamino, $C_{1-6}$alkoxy where $C_{1-6}$alkoxy is substituted by heterocyclyl, heterocyclyl, or R1 and R2, together with the phenyl ring to which they are attached, form a five- to eight-membered monocarbocyclic ring;
R2 is H, or R1 and R2, together with the phenyl ring to which they are attached, form a five- to eight-membered monocarbocyclic ring;
R3 is $C_{1-6}$alkoxy or H;
R4 is H, $C_{1-6}$alkoxy, N-($C_{1-6}$alkyl)aminocarbonyl, ($C_{1-6}$alkyl)sulfonyl, N-[($C_{1-6}$alkyl)sulfonyl]-N-($C_{1-6}$alkyl)amino, where the alkyl groups of N-[($C_{1-6}$alkyl)sulfonyl]-N-($C_{1-6}$alkyl)amino may be the same or different, or heteroaryl; and
R5 is H, N-($C_{1-6}$alkyl)aminosulfonyl or N,N-di-($C_{1-6}$alkyl)aminosulfonyl, where the alkyl groups of N,N-di-($C_{1-6}$alkyl)aminosulfonyl may be the same or different.

14. A compound according to claim 1 which is:
(14Z)-6-Chloro-17-(4-methylpiperazin-1-yl)-2,4,8,22-tetraazatetracyclo[14.3.1.$1^{3,7}.1^{9,13}$]docosa-1(20),3(22),4,6,9(21),10,12,14,16,18-decaene;
6-Chloro-17-(4-methylpiperazin-1-yl)-2,4,8,22-tetraazatetracyclo[14.3.1.$1^{3,7}.1^{9,13}$]docosa-1(20),3(22),4,6,9(21),10,12,16,18-nonaene;
(14Z)-6-Chloro-10-(2-methanesulfonyl-methyl-amino)-17-(4-methylpiperazin-1-yl)-19-methoxy-2,4,8,22-tetraazatetracyclo[14.3.1.$1^{3,7}.1^{9,13}$]docosa-1(20),3(22),4,6,9(21),10,12,14,16,18-decaene;
6-Chloro-10-(2-methanesulfonyl-methyl-amino)-17-(4-methylpiperazin-1-yl)-19-methoxy-2,4,8,22-tetraazatetracyclo[14.3.1.$1^{3,7}.1^{9,13}$]docosa-1(20),3(22),4,6,9(21),10,12,16,18-nonaene;
6-Chloro-10-(propane-2-sulfonyl)-17-(4-methylpiperazin-1-yl)-19-methoxy-2,4,8,22-tetraazatetracyclo[14.3.1.$1^{3,7}.1^{9,13}$]docosa-1(20),3(22),4,6,9(21),10,12,16,18-nonaene;
(14Z)-6-Chloro-10-(2-methanesulfonyl-methyl-amino)-17-(1-methyl-piperidin-4-yl)-19-methoxy-2,4,8,22-tetraazatetracyclo[14.3.1.$1^{3,7}.1^{9,13}$]docosa-1(20),3(22),4,6,9(21),10,12,14,16,18-decaene;
6-Chloro-10-(2-methanesulfonyl-methyl-amino)-17-(1-methyl-piperidin-4-yl)-19-methoxy-2,4,8,22-tetraazatetracyclo[14.3.1.$1^{3,7}.1^{9,13}$]docosa-1(20),3(22),4,6,9(21),10,12,16,18-nonaene;
(14Z)-6-Chloro-10-(2-methanesulfonyl-methyl-amino)-17-(4-methylpiperazin-1-yl)-2,4,8,22-tetraazatetracyclo[14.3.1.$1^{3,7}.1^{9,13}$]docosa-1(20),3(22),4,6,9(21),10,12,14,16,18-decaene;
6-Chloro-10-(2-methanesulfonyl-methyl-amino)-17-(4-methylpiperazin-1-yl)-2,4,8,22-tetraazatetracyclo[14.3.1.$1^{3,7}.1^{9,13}$]docosa-1(20),3(22),4,6,9(21),10,12,16,18-nonaene;
(14Z)-6-Chloro-10-(propane-2-sulfonyl)-17-(4-methylpiperazin-1-yl)-2,4,8,22-tetraazatetracyclo[14.3.1.$1^{3,7}.1^{9,13}$]docosa-1(20),3(22),4,6,9(21),10,12,14,16,18-decaene;
6-Chloro-10-(propane-2-sulfonyl)-17-(4-methylpiperazin-1-yl)-2,4,8,22-tetraazatetracyclo[14.3.1.$1^{3,7}.1^{9,13}$]docosa-1(20),3(22),4,6,9(21),10,12,16,18-nonaene;
(14Z)-6-Chloro-10-methoxy-17-(4-methylpiperazin-1-yl)-2,4,8,22-tetraazatetracyclo[14.3.1.$1^{3,7}.1^{9,13}$]docosa-1(20),3(22),4,6,9(21),10,12,14,16,18-decaene;
6-Chloro-10-methoxy-17-(4-methylpiperazin-1-yl)-2,4,8,22-tetraazatetracyclo[14.3.1.$1^{3,7}.1^{9,13}$]docosa-1(20),3(22),4,6,9(21),10,12,16,18-nonaene;
6-Chloro-17-(4-methylpiperazin-1-yl)-19-methoxy-2,4,8,22-tetraazatetracyclo[14.3.1.$1^{3,7}.1^{9,13}$]docosa-1(20),3(22),4,6,9(21),10,12,16,18-nonaene;
(14Z)-6-Chloro-10-(N-methylcarboxamido)-17-(4-methylpiperazin-1-yl)-2,4,8,22-tetraazatetracyclo[14.3.1.$1^{3,7}.1^{9,13}$]docosa-1(20),3(22),4,6,9(21),10,12,14,16,18-decaene;
6-Chloro-10-(N-methylcarboxamido)-17-(4-methylpiperazin-1-yl)-2,4,8,22-tetraazatetracyclo[14.3.1.$1^{3,7}.1^{9,13}$]docosa-1(20),3(22), 4,6,9(21),10,12,16,18-nonaene;
(14Z)-6-Chloro-10-(methanesulfonyl)-17-(4-methylpiperazin-1-yl)-2,4,8,22-tetraazatetracyclo[14.3.1.$1^{3,7}.1^{9,13}$]docosa-1(20),3(22),4,6,9(21),10,12,14,16,18-decaene;
6-Chloro-10-(methanesulfonyl)-17-(4-methylpiperazin-1-yl)-2,4,8,22-tetraazatetracyclo[14.3.1.$1^{3,7}.1^{9,13}$]docosa-1(20),3(22),4,6,9(21),10,12,16,18-nonaene;
(14Z)-6-Chloro-10-methoxy-17-(morpholin-4-yl)-2,4,8,22-tetraazatetracyclo[14.3.1.$1^{3,7}.1^{9,13}$]docosa-1(20),3(22),4,6,9(21),10,12,14,16,18-decaene;
6-Chloro-10-methoxy-17-(morpholin-4-yl)-2,4,8,22-tetraazatetracyclo[14.3.1.$1^{3,7}.1^{9,13}$]docosa-1(20),3(22),4,6,9(21),10,12,16,18-nonaene;
(14Z)-6-Chloro-17-[2-(pyrrolidin-1-yl)ethoxy]-2,4,8,22-tetraazatetracyclo[14.3.1.$1^{3,7}.1^{9,13}$]docosa-1(20),3(22),4,6,9(21),10,12,14,16,18-decaene;
6-Chloro-17-[2-(pyrrolidin-1-yl)ethoxy]-2,4,8,22-tetraazatetracyclo[14.3.1.$1^{3,7}.1^{9,13}$]docosa-1(20),3(22),4,6,9(21),10,12,16,18-nonaene;
(14Z)-6-Chloro-17-(morpholin-4-yl)-2,4,8,22-tetraazatetracyclo[14.3.1.$1^{3,7}.1^{9,13}$]docosa-1(20),3(22),4,6,9(21),10,12,14,16,18-decaene;
6-Chloro-17-(morpholin-4-yl)-2,4,8,22-tetraazatetracyclo[14.3.1.$1^{3,7}.1^{9,13}$]docosa-1(20),3(22),4,6,9(21),10,12,16,18-nonaene;
(14R,15S)-6-chloro-17-(4-methylpiperazin-1-yl)-2,4,8,22-tetraazatetracyclo[14.3.1.$1^{3,7}.1^{9,13}$]docosa-1(20),3(22),4,6,9(21),10,12,16,18-nonaene-14,15-diol;
6-Chloro-10-(2-methanesulfonyl-methyl-amino)-17-(piperidin-4-yl)-19-methoxy-2,4,8,22-tetraazatetracyclo[14.3.1.$1^{3,7}.1^{9,13}$]docosa-1(20),3(22),4,6,9(21),10,12,16,18-nonaene; or
N-[(20S)-6-chloro-24-methoxy-20-(morpholin-4-yl)-2,4,8,27-tetraazapentacyclo[14.8.1.$1^{3,7}.1^{9,13}.0^{17,23}$]heptacosa-1(25),3(27),4,6,9(26),10,12,16,23-nonaen-10-yl] N-methylmethanesulfonamide; or
a pharmaceutically acceptable salt thereof.

15. A compound which is:
6,13,19-Triaza-4-chloro-7,$14^{1,3}$-dibenzena-$1^{2,4}$-pyrimidinacyclodocosaph-12-one;
(14R,15S)-6-chloro-2,4,8,22-tetraazatetracyclo[14.3.1.$1^{3,7}.1^{9,13}$]docosa-1(20),3(22),4,6,9(21),10,12,16,18-nonaene-14,15-diol; or
6-Trifluoromethyl-2,4,8,22-tetraazatetracyclo[14.3.1.$1^{3,7}.1^{9,13}$]docosa-1(20),3(22),4,6,9(21),10,12,16,18-nonaene; or
or a pharmaceutically acceptable salt thereof.

16. A compound according to claim 1 or claim 15 for use in treating a subject suffering from an ALK-, FAK- or JAK2-mediated disorder or condition.

17. A compound according to claim 16, wherein the ALK-, FAK- or JAK2-mediated disorder or condition is cancer.

18. A compound according to claim 16, wherein the ALK-, FAK- or JAK2-mediated disorder or condition is selected from colon cancer, breast cancer, renal cancer, lung cancer, hemangioma, squamous cell myeloid leukemia, melanoma, glioblastoma, and astrocytoma.

19. A compound according to claim 1 or claim 15 for use in treating a subject suffering from a proliferative disorder.

20. A compound according to claim 19 wherein the proliferative disorder is cancer.

21. A compound according to claim 20 wherein the proliferative disorder is selected from colon cancer, breast cancer, renal cancer, lung cancer, hemangioma, squamous cell myeloid leukemia, melanoma, glioblastoma, and astrocytoma.

22. A pharmaceutical composition comprising a compound according to claim 1 or claim 15 and a pharmaceutically acceptable carrier, diluent or excipient therefore.

* * * * *